United States Patent
Arslanian et al.

(10) Patent No.: US 6,589,968 B2
(45) Date of Patent: *Jul. 8, 2003

(54) EPOTHILONE COMPOUNDS AND METHODS FOR MAKING AND USING THE SAME

(75) Inventors: Robert L. Arslanian, Pacifica, CA (US); John R. Carney, San Bruno, CA (US); Brian Metcalf, Moraga, CA (US)

(73) Assignee: Kosan Biosciences, Inc., Hayward, CA (US)

(*) Notice: Subject to any disclaimer, the term of this patent is extended or adjusted under 35 U.S.C. 154(b) by 127 days.

This patent is subject to a terminal disclaimer.

(21) Appl. No.: 09/825,876

(22) Filed: Apr. 3, 2001

(65) Prior Publication Data

US 2002/0156110 A1 Oct. 24, 2002

Related U.S. Application Data

(60) Provisional application No. 60/269,020, filed on Feb. 13, 2001.

(51) Int. Cl.[7] ................ C07D 277/20; A61K 31/426
(52) U.S. Cl. ........................ 514/365; 548/204
(58) Field of Search ............................ 548/204; 514/365

(56) References Cited

U.S. PATENT DOCUMENTS

| | | | |
|---|---|---|---|
| 5,415,869 A | 5/1995 | Straubinger et al. | 424/450 |
| 5,424,073 A | 6/1995 | Rahman et al. | 424/450 |
| 5,510,118 A | 4/1996 | Bosch et al. | 424/489 |
| 5,534,270 A | 7/1996 | De Castro | 424/490 |
| 5,662,883 A | 9/1997 | Bagchi et al. | 424/9.4 |
| 5,683,715 A | 11/1997 | Boni et al. | 424/450 |
| 6,120,847 A | 9/2000 | Yang et al. | 427/335 |
| 6,156,373 A | 12/2000 | Zhong et al. | 427/2.28 |
| 6,359,140 B1 * | 3/2002 | Hoefle | 548/204 |

FOREIGN PATENT DOCUMENTS

| | | |
|---|---|---|
| WO | WO 93/10121 | 5/1993 |
| WO | WO 97/19086 | 5/1997 |
| WO | WO 98/22461 | 5/1998 |
| WO | WO 98/30205 | 7/1998 |
| WO | WO 99/07692 | 2/1999 |
| WO | WO 99/39694 | 8/1999 |
| WO | WO 99/42602 | 8/1999 |
| WO | WO 99/43653 | 9/1999 |
| WO | WO 99/65913 | 12/1999 |
| WO | WO 00/00485 | 1/2000 |
| WO | WO 00/31247 | 6/2000 |
| WO | WO 00/39276 | 7/2000 |
| WO | WO 00/50423 | * 8/2000 |
| WO | WO 00/71163 | 11/2000 |
| WO | WO 01/10412 | 2/2001 |

OTHER PUBLICATIONS

Gerth et al., The Journal of Antibiotics (1996) 49:560–563.
Giannokakou et al., Int. J. Cancer (1998) 75:57–63.
Giannakakou et al., J. Biol. Chem. (1997) 271:17118–17125.
Hofle et al., Angew. Chem. Int. Ed. Engl. (1996) 35(13/14):1567–1569.
Skehan et al., J. Natl. Cancer Inst. (1990) 82:1107–1112.
Tang et al., Science (2000) 287:640–641.
U.S. application Ser. No. 10/115,198 Ashley et al. Apr. 2, 2002.

* cited by examiner

Primary Examiner—Joseph K. McKane
Assistant Examiner—Golam M M Shameem
(74) Attorney, Agent, or Firm—Carolyn A. Favorito; David Lentini; Kevin Kaster

(57) ABSTRACT

This present invention relates to compounds of formula (I)

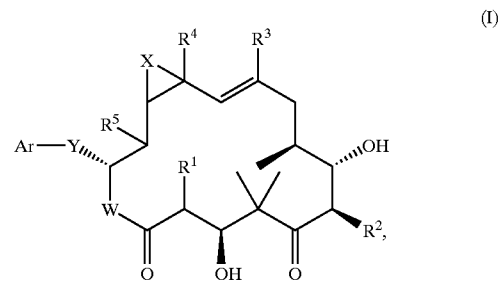

and to pharmaceutically acceptable salts and solvates thereof, wherein $R^1$, $R^2$, $R^3$, $R^4$, $R^5$, W, X, Y, and Ar are as defined herein. Compounds of formula (I) are useful in the treatment of diseases or conditions characterized by cellular hyperproliferation. This invention also relates to means for the preparation of compounds of formula (I); formulations containing compounds of formula (I); and methods for the use of said compounds and formulations in the treatment of a disease or condition characterized by cellular hyperproliferation, including cancer.

8 Claims, No Drawings

EPOTHILONE COMPOUNDS AND METHODS FOR MAKING AND USING THE SAME

This application claims priority under 35 U.S.C. § 120 from U.S. utility patent application Ser. Nos. 09/825,856 filed on Apr. 3, 2001 and 09/825,876 filed on Apr. 3, 2001, which claims benefit of priority from U.S. provisional application Ser. No. 60/269,020 filed on Feb. 13, 2001. The contents of these applications are relied on and incorporated herein in their entirety by reference.

TECHNICAL FIELD

The invention relates to epothilone compounds that are useful for the treatment of cancer and other conditions characterized by undesireable cellular proliferation. More particularly, the invention relates to 10,11-dehydroepothilones.

BACKGROUND ART

Epothilone A (R=H) and Epothilone B (R=CH$_3$) are produced by *Sorangium cellulosum* strain So ce 90, the structures of which are shown below, and were the first of several epothilones to be isolated, synthesized, and characterized. Höfle et al., 1996, *Angew. Chem. Int. Ed. Engl.* 35(13/14): 1567–1569.

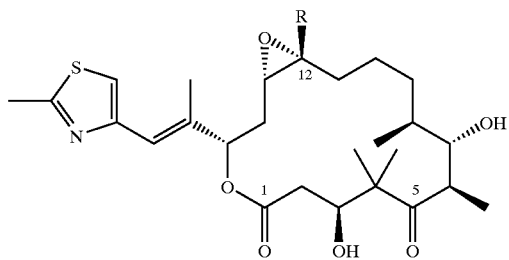

Epothilone A and epothilone B possess many of the advantageous properties of paclitaxel (Taxol®, Bristol-Myers Squibb). As a result, there is significant interest in these and structurally related compounds as potential chemotherapeutic agents. The desoxy counterparts of epothilones A and B are known as epothilone C(R=H) and epothilone D(R=CH$_3$), and exhibit similar anti-tumor activity but with less cytotoxicity. The structures of epothilones C and D are shown below.

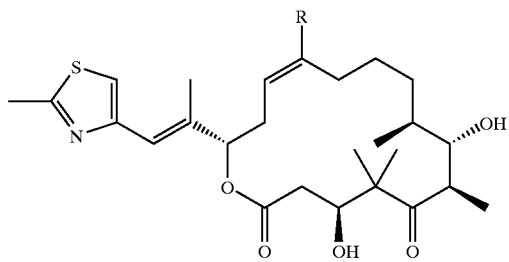

Although other naturally occurring epothilones have been described, these compounds are produced in exceedingly small amounts. PCT publication WO 99/65913 describes 39 naturally occurring epothilones obtained from *Sorangium cellulosum* So ce 90 of which epothilones A, B, C, and D together account for approximately 98.9% of the total epothilones produced. The 35 other naturally occurring epothilone compounds together account for the remaining 1.1% and include epothilone C$_6$ (which may also be referred to as 10,11-dehydroepothilone C) and whose structure is shown below

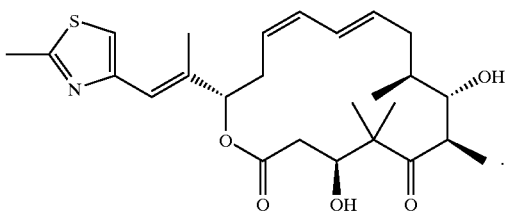

The naturally occurring epothilones can be modified through semisynthesis. PCT publication WO 99/27890 describes conversion of epothilones A and B into their lactam analogs. PCT publication WO 99/54318 describes conversion of epothilones C and D into their 12,13-cyclopropane analogs.

Additional epothilone analogs may be produced through de novo synthesis. PCT publications WO 99/07692 and WO 00/00485 describe a synthetic route wherein the methyl group at C-6 is replaced by other aliphatic groups and unsaturation may be introduced at the 10,11-position. PCT publication WO 99/02514 describes total synthesis of lactam analogs of epothilones.

Due to the increasing interest in epothilones as anti-cancer agents, novel derivatives of these compounds are needed and desired to more fully develop their therapeutic potential. The present invention fulfils this need.

DISCLOSURE OF THE INVENTION

This invention relates to epothilone compounds that are useful for the treatment of cancer and other conditions characterized by undesireable cellular proliferation. More particularly, the invention relates to 10,11-dehydroepothilones.

In one aspect, the present invention provides a compound of the formula

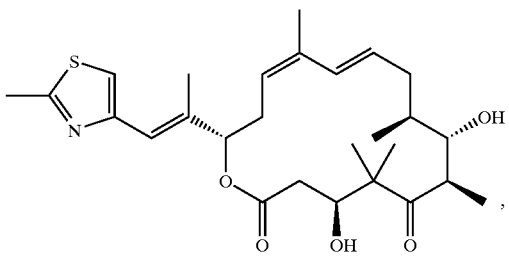

known herein as 10,11-dehydroepothilone D.

In another aspect, the present invention provides compounds of the formula (I)

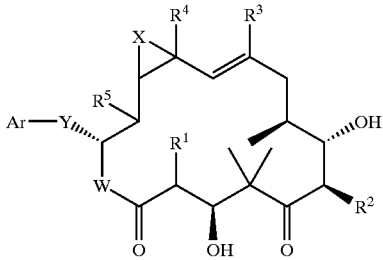

(I)

wherein:

$R^1$, $R^2$, and $R^3$, are each independently H, $C_1$–$C_5$ alkyl, $C_2$–$C_5$ alkenyl, $C_2$–$C_5$ alkynyl, aryl or alkylaryl;

$R^4$ is H, $C_1$–$C_5$ alkyl, $C_1$–$C_5$ hydroxyalkyl, $C_1$–$C_5$ haloalkyl, aryl, —C(=O)$R^6$, —C(=O)O$R^6$, or —N$R^6R^7$ where $R^6$ and $R^7$ are each independently hydrogen, $C_1$–$C_5$ aliphatic, aryl or alkylaryl;

$R^5$ is H, $C_1$–$C_5$ alkyl, $C_1$–$C_5$ alkoxy, $C_2$–$C_5$ alkenyl, $C_2$–$C_5$ alkynyl, aryl or alkylaryl;

W is O, N$R^8$ where $R^8$ is hydrogen, $C_1$–$C_5$ alkyl, $C_2$–$C_5$ alkenyl, $C_2$–$C_5$ alkynyl, aryl or alkylaryl;

X is O, $CH_2$ or a carbon-carbon bond;

Y is absent or a $C_1$–$C_5$ alkyl, $C_2$–$C_5$ alkenyl, or $C_2$–$C_5$ alkynyl; and Ar is aryl; provided that when W is O at least one of $R^1$, $R^3$, or $R^5$ is other than H.

In one embodiment, the present invention provides compounds of the formula (II)

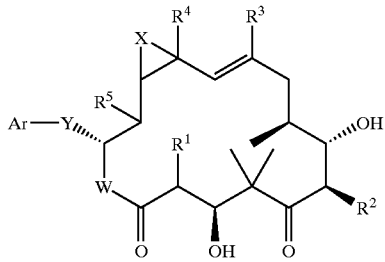

(II)

wherein:

$R^1$, $R^2$, and $R^3$, are each independently H, $C_1$–$C_5$ alkyl, $C_2$–$C_5$ alkenyl, $C_2$–$C_5$ alkynyl, aryl or alkylaryl;

$R^4$ is H, $C_1$–$C_5$ alkyl, $C_1$–$C_5$ hydroxyalkyl, $C_1$–$C_5$ haloalkyl, aryl, —C(=O)$R^6$, —C(=O)O$R^6$, or —N$R^6R^7$ where $R^6$ and $R^7$ are each independently hydrogen, $C_1$–$C_5$ aliphatic, aryl or alkylaryl;

$R^5$ is H, $C_1$–$C_5$ alkyl, $C_1$–$C_5$ alkoxy, $C_2$–$C_5$ alkenyl, $C_2$–$C_5$ alkynyl, aryl or alkylaryl;

W is N$R^8$ where $R^8$ is hydrogen, $C_1$–$C_5$ alkyl, $C_2$–$C_5$ alkenyl, $C_2$–$C_5$ alkynyl, aryl or alkylaryl;

X is O, $CH_2$ or a carbon-carbon bond;

Y is absent or a $C_1$–$C_5$ alkyl, $C_2$–$C_5$ alkenyl, or $C_2$–$C_5$ alkynyl; and Ar is aryl.

In one embodiment of the invention, compounds of formula (III) are provided

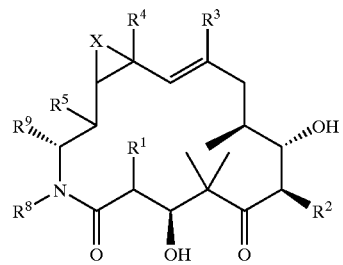

(III)

wherein:

$R^1$, $R^2$, and $R^3$, are each independently H, $C_1$–$C_5$ alkyl, $C_2$–$C_5$ alkenyl, $C_2$–$C_5$ alkynyl, aryl or alkylaryl;

$R^4$ is H, $C_1$–$C_5$ alkyl, $C_1$–$C_5$ hydroxyalkyl, $C_1$–$C_5$ haloalkyl, aryl, —C(=O)$R^6$, —C(=O)O$R^6$, or —N$R^6R^7$ where $R^6$ and $R^7$ are each independently hydrogen, $C_1$–$C_5$ aliphatic, aryl or alkylaryl;

$R^5$ is H, $C_1$–$C_5$ alkyl, $C_1$–$C_5$ alkoxy, $C_2$–$C_5$ alkenyl, or $C_2$–$C_5$ alkynyl;

$R^8$ is H, $C_1$–$C_5$ alkyl, $C_2$–$C_5$ alkenyl, $C_2$–$C_5$ alkynyl, aryl or alkylaryl;

X is O, $CH_2$ or a carbon-carbon bond; and $R^9$ is selected from the group consisting of

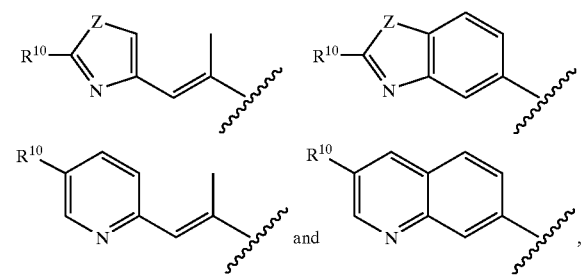

where Z is O or S, and $R^{10}$ is H, $C_1$–$C_5$ alkyl, $C_1$–$C_5$ hydroxyalkyl, $C_1$–$C_5$ fluoroalkyl, or $C_1$–$C_5$ aminoalkyl.

In another embodiment of the invention, compounds of formula (III) are provided wherein:

$R^1$, $R^2$, and $R^3$ are each independently H, $C_1$–$C_5$ alkyl, $C_2$–$C_5$ alkenyl, $C_2$–$C_5$ alkynyl, or alkylaryl;

$R^4$ is H, $C_1$–$C_5$ alkyl, $C_1$–$C_5$ hydroxyalkyl, or $C_1$–$C_5$ haloalkyl;

$R^5$ is H, $C_1$–$C_5$ alkyl, or $C_1$–$C_5$ alkoxy;

$R^8$ is hydrogen or $C_1$–$C_5$ alkyl;

X is O, $CH_2$ or a carbon-carbon bond; and $R^9$ is selected from the group consisting of

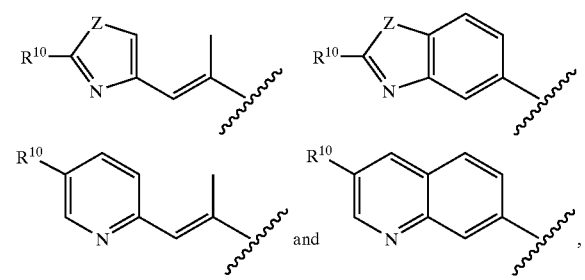

where Z is O or S, and $R^{10}$ is H, methyl, hydroxymethyl, fluoromethyl, or aminomethyl.

In one embodiment of the invention, compounds of formula (III) are provided wherein:
$R^1$ and $R^3$ are methyl;
$R^2$ is H;
$R^4$ is H, methyl, ethyl, fluoromethyl, or hydroxymethyl;
$R^5$ is H, methyl, ethyl, or methoxy;
R8 is hydrogen or methyl;
X is O, $CH_2$ or a carbon-carbon bond; and
$R^9$ is selected from the group consisting of

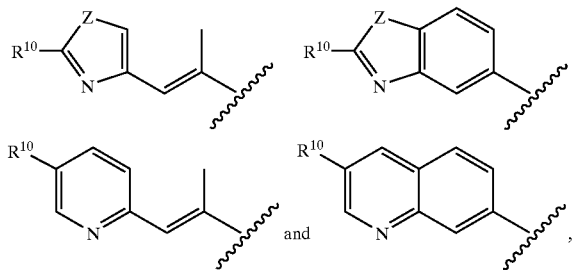

where Z is O or S, and $R^{10}$ is H, methyl, hydroxymethyl, fluoromethyl, or aminomethyl.

In another embodiment of the invention, compounds of formula (IV) are provided

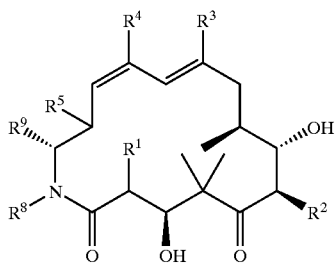

(IV)

wherein:
$R^1$, $R^2$, and $R^3$ are each independently hydrogen, $C_1$–$C_5$ alkyl, $C_2$–$C_5$ alkenyl, $C_2$–$C_5$ alkynyl, or alkylaryl;
$R^4$ is H, $C_1$–$C_5$ alkyl, $C_1$–$C_5$ hydroxyalkyl, or $C_1$–$C_5$ haloalkyl;
$R^5$ is H, $C_1$–$C_5$ alkyl, $C_1$–$C_5$ alkoxy, $C_2$–$C_5$ alkenyl, or $C_2$–$C_5$ alkynyl;
$R^8$ is hydrogen or $C_1$–$C_5$ alkyl;
X is O, $CH_2$ or a carbon-carbon bond; and
$R^9$ is selected from the group consisting of

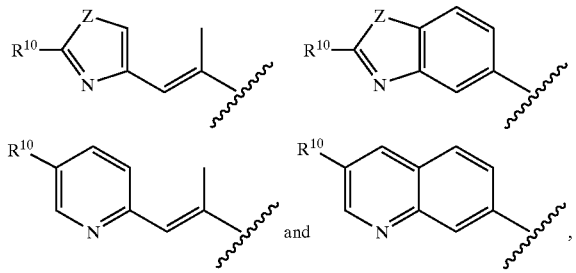

where Z is O or S, and $R^{10}$ is H, methyl, hydroxymethyl, fluoromethyl, or aminomethyl.

In another embodiment of the invention, compounds of formula (IV) are provided wherein:
$R^1$ and $R^3$ are H;
R2 is methyl;
$R^4$ is H, $C_1$–$C_5$ alkyl, $C_1$–$C_5$ hydroxyalkyl, or $C_1$–$C_5$ haloalkyl;
$R^5$ is H, $C_1$–$C_5$ alkyl, or $C_1$–$C_5$ alkoxy;
$R^8$ is hydrogen or $C_1$–$C_5$ alkyl;
X is O, $CH_2$ or a carbon-carbon bond; and
$R^9$ is selected from the group consisting of

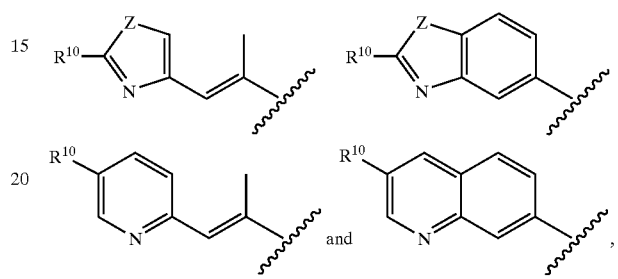

where Z is O or S, and $R^{10}$ is H, methyl, hydroxymethyl, fluoromethyl, or aminomethyl.

In another embodiment of the invention, compounds of formula (IV) are provided wherein:
$R^1$ and $R^3$ are H;
R2 is methyl;
$R^4$ is H, methyl, ethyl, fluoromethyl, or hydroxymethyl;
$R^5$ is H, methyl, ethyl, or methoxy;
$R^8$ is hydrogen or methyl;
X is O, $CH_2$ or a carbon-carbon bond; and
$R^9$ is selected from the group consisting of

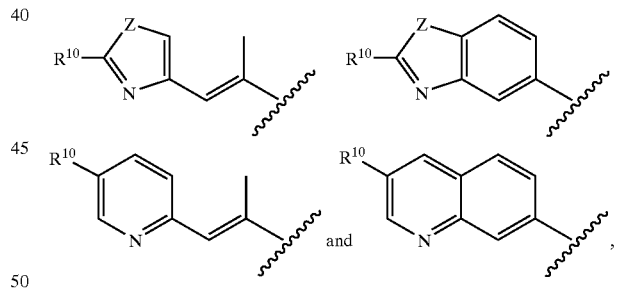

where Z is O or S, and $R^{10}$ is H, methyl, hydroxymethyl, fluoromethyl, or aminomethyl.

In another embodiment of the invention, compounds of the formulas

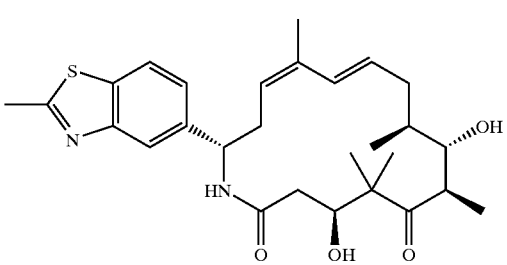

-continued

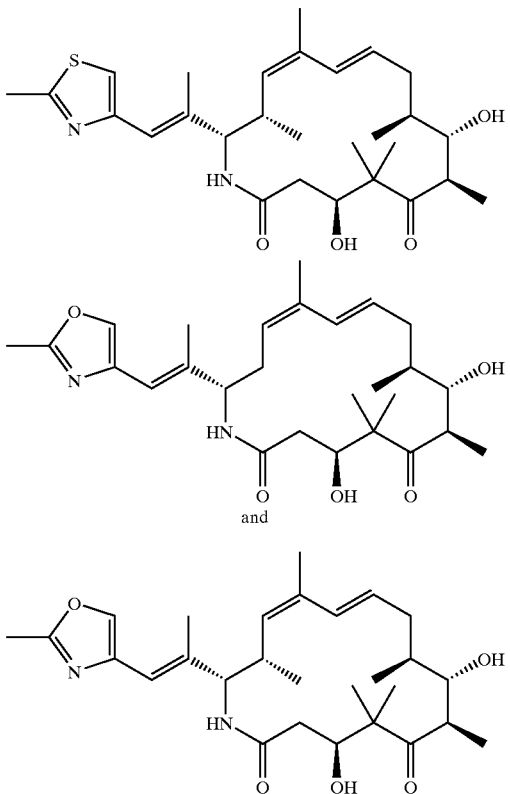

and

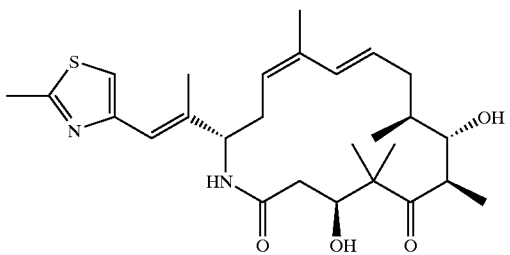

are provided.

In another embodiment of the invention, the compound having the formula

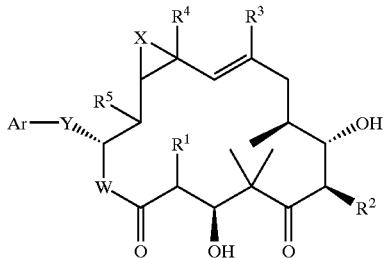

is provided.

In one embodiment, the present invention provides compounds of the formula (V)

(V)

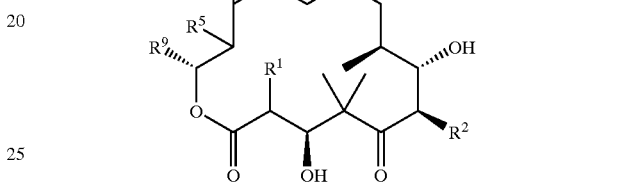

wherein:

$R^1$, $R^2$, and $R^3$, are each independently H, $C_1$–$C_5$ alkyl, $C_2$–$C_5$ alkenyl, $C_2$–$C_5$ alkynyl, aryl or alkylaryl;

$R^4$ is H, $C_1$–$C_5$ alkyl, $C_1$–$C_5$ hydroxyalkyl, $C_1$–$C_5$ haloalkyl, aryl, —C(=O)$R^6$, —C(=O)O$R^6$, or $N^6R^7$ where $R^6$ and $R^7$ are each independently hydrogen, $C_1$–$C_5$ aliphatic, aryl or alkylaryl;

$R^5$ is $C_1$–$C_5$ alkyl, $C_1$–$C_5$ alkoxy, $C_2$–$C_5$ alkenyl, $C_2$–$C_5$ alkynyl, aryl or alkylaryl;

W is O;

X is O, $CH_2$ or a carbon-carbon bond;

Y is absent or a $C_1$–$C_5$ alkyl, $C_2$–$C_5$ alkenyl, or $C_2$–$C_5$ alkynyl; and Ar is aryl.

In one embodiment of the invention, compounds of formula (VI) are provided (VI)

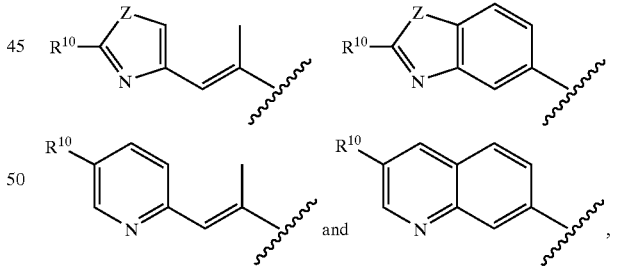

wherein:

$R^1$, $R_2$, and $R^3$, are each independently H, $C_1$–$C_5$ alkyl, $C_2$–$C_5$ alkenyl, $C_2$–$C_5$ alkynyl, aryl or alkylaryl;

$R^4$ is H, $C_1$–$C_5$ alkyl, $C_1$–$C_5$ hydroxyalkyl, $C_1$–$C_5$ haloalkyl, aryl, —C(=O)$R^6$, —C(=O)O$R_6$, or —NR6$R^7$ where $R^6$ and $R^7$ are each independently hydrogen, $C_1$–$C_5$ aliphatic, aryl or alkylaryl;

$R^5$ is $C_1$–$C_5$ alkyl, $C_1$–$C_5$ alkoxy, $C_2$–$C_5$ alkenyl, or $C_2$–$C_5$ alkynyl;

$R^8$ is H, $C_1$–$C_5$ alkyl, $C_2$–$C_5$ alkenyl, $C_2$–$C_5$ alkynyl, aryl or alkylaryl;

X is O, $CH_2$ or a carbon-carbon bond; and $R^9$ is selected from the group consisting of where Z is O or S, and $R^{10}$ is H, $C_1$–$C_5$ alkyl, $C_1$–$C_5$ hydroxyalkyl, $C_1$–$C_5$ fluoroalkyl, or $C_1$–$C_5$ aminoalkyl.

In another embodiment of the invention, compounds of formula (VI) are provided wherein:

$R^1$, $R^2$, and $R^3$ are each independently H, $C_1$–$C_5$ alkyl, $C_2$–$C_5$ alkenyl, $C_2$–$C_5$ alkynyl, or alkylaryl;

$R^4$ is H, $C_1$–$C_5$ alkyl, $C_1$–$C_5$ hydroxyalkyl, or $C_1$–$C_5$ haloalkyl;

$R^5$ is $C_1$–$C_5$ alkyl, or $C_1$–$C_5$ alkoxy;

$R^8$ is hydrogen or $C_1$–$C_5$ alkyl;

X is O, $CH_2$ or a carbon-carbon bond; and

R⁹ is selected from the group consisting of where Z is O or S, and $R^{10}$ is H, methyl, hydroxymethyl, fluoromethyl, or aminomethyl.

In one embodiment of the invention, compounds of formula (VI) are provided wherein:
$R^1$ and $R^3$ are methyl;
$R^2$ is H;
$R^4$ is H, methyl, ethyl, fluoromethyl, or hydroxymethyl;
$R^5$ is methyl, ethyl, or methoxy;
$R^8$ is hydrogen or methyl;
X is O, $CH_2$ or a carbon-carbon bond; and
$R^9$ is selected from the group consisting of where Z is O or S, and $R^{10}$ is H, methyl, hydroxymethyl, fluoromethyl, or aminomethyl.

In another embodiment of the invention, compounds of formula (VII) are provided $$\text{(VII)}$$

wherein:
$R^1$, $R^2$, and $R^3$ are each independently hydrogen, $C_1$–$C_5$ alkyl, $C_2$–$C_5$ alkenyl, $C_2$–$C_5$ alkynyl, or alkylaryl;
$R^4$ is H, $C_1$–$C_5$ alkyl, $C_1$–$C_5$ hydroxyalkyl, or $C_1$–$C_5$ haloalkyl;
$R^5$ is $C_1$–$C_5$ alkyl, $C_1$–$C_5$ alkoxy, $C_2$–$C_5$ alkenyl, or $C_2$–$C_5$ alkynyl;
$R^8$ is hydrogen or $C_1$–$C_5$ alkyl;
X is O, $CH_2$ or a carbon–carbon bond; and R⁹ is selected from the group consisting of where Z is O or S, and $R^{10}$ is H, methyl, hydroxymethyl, fluoromethyl, or aminomethyl.

In another embodiment of the invention, compounds of formula (VII) are provided wherein:
$R^1$ and $R^3$ are H;
$R^2$ is methyl;
$R^4$ is H, $C_1$–$C_5$ alkyl, $C_1$–$C_5$ hydroxyalkyl, or $C_1$–$C_5$ haloalkyl;
$R^5$ is $C_1$–$C_5$ alkyl, or $C_1$–$C_5$ alkoxy;
$R^8$ is hydrogen or $C_1$–$C_5$ alkyl;
X is O, $CH_2$ or a carbon-carbon bond; and
$R^9$ is selected from the group consisting of where Z is O or S, and $R^{10}$ is H, methyl, hydroxymethyl, fluoromethyl, or aminomethyl.

In another embodiment of the invention, compounds of formula (VII) are provided wherein:
$R^1$ and $R^3$ are H;
$R^2$ is methyl;
$R^4$ is H, methyl, ethyl, fluoromethyl, or hydroxymethyl;
$R^5$ is methyl, ethyl, or methoxy;
$R^8$ is hydrogen or methyl;
X is O, $CH_2$ or a carbon-carbon bond; and
$R^9$ is selected from the group consisting of where Z is O or S, and $R^{10}$ is H, methyl, hydroxymethyl, fluoromethyl, or aminomethyl.

In another embodiment of the invention, compounds of the formulas

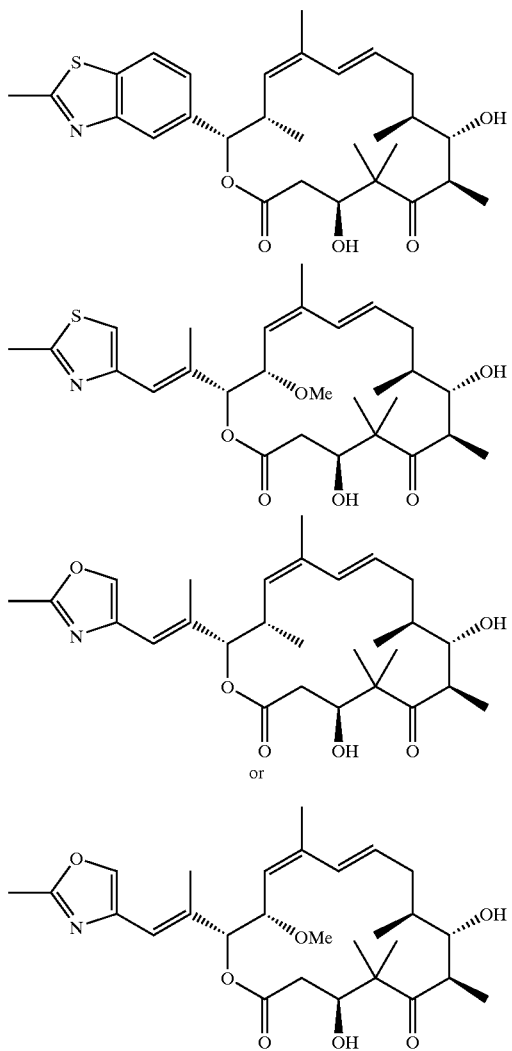

are provided.

In another embodiment of the invention, the compound having the formula

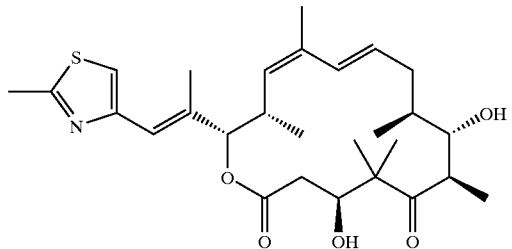

is provided.

In another aspect of the present invention, methods for preparing the inventive compounds are provided. In one embodiment, certain of the inventive compounds are prepared by total synthesis. In another embodiment, certain of the inventive compounds are prepared by fermentation of genetically engineered organisms. In another embodiment, certain of the inventive compounds are prepared by chemical transformations performed on compounds prepared by fermentation of genetically engineered organisms. In another embodiment, certain of the inventive compounds are prepared by microbial transformations performed on compounds prepared by fermentation of genetically engineered organisms.

In another aspect of the invention, formulations comprising one or more of the inventive compounds are provided. In one embodiment, the inventive compound or compounds constitute the active principle of the formulation. In another embodiment, the inventive compounds are combined with other active compounds, such as cytotoxic agents and synergists.

In another aspect of the present invention, methods for treating a disease or condition with the inventive compounds are provided. In one embodiment, the inventive compounds are used for treating a disease or condition characterized by cellular hyperproliferation in a subject. In one embodiment, the disease is cancer, including but not limited to cancers of the head and neck, liver or biliary tree, intestine, ovary, lung, central nervous system, lymphatic system, or sarcomas. In another embodiment, the condition is psoriasis, multiple sclerosis, rheumatoid arthritis, or atherosclerosis. In another embodiment, the condition is stenosis or restenosis.

Statements regarding the scope of the present invention and definitions of terms used herein are listed below. The definitions apply to the terms as they are used throughout this specification, unless otherwise limited in specific instances, either individually or as part of a larger group.

Unless stereochemistry is specifically indicated, all stereoisomers of the inventive compounds are included within the scope of the invention, as pure compounds as well as mixtures thereof.

Some of the crystalline forms for the compounds may exist as polymorphs and as such are included in the present invention. In addition, some of the compounds may form solvates with water (i.e., hydrates) or common organic solvents, and such solvates are also encompassed within the scope of this invention.

Protected forms of the inventive compounds are included within the scope of the present invention. A variety of protecting groups are disclosed, for example, in T. H. Greene and P. G. M. Wuts, Protective Groups in Organic Synthesis, Third Edition, John Wiley & Sons, New York (1999), which is incorporated herein by reference in its entirety. For example, a hydroxy protected form of the inventive compounds are those where at least one of the hydroxyl groups is protected by a hydroxy protecting group. Illustrative hydroxy protecting groups include but not limited to tetrahydropyranyl; benzyl; methylthiomethyl; ethylthiomethyl; pivaloyl; phenylsulfonyl; triphenylmethyl; trisubstituted silyl such as trimethyl silyl, triethylsilyl, tributylsilyl, triisopropylsilyl, t-butyldimethylsilyl, tri-t-butylsilyl, methyldiphenylsilyl, ethyldiphenylsilyl, t-butyldiphenylsilyl and the like; acyl and aroyl such as acetyl, pivaloylbenzoyl, 4-methoxybenzoyl, 4-nitrobenzoyl and aliphatic acylaryl and the like. Keto groups in the inventive compounds may similarly be protected.

The present invention includes within its scope prodrugs of the compounds shown herein. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to a subject in need thereof. Conventional procedures for the selection and preparation of suitable prodrug derivatives are described, for example, in "Design of Prodrugs", H. Bundgaard ed., Elsevier, 1985.

The term "subject" as used herein, refers to an animal, preferably a mammal, that has been the object of treatment, observation or experiment, and most preferably refers to a human whom has been the object of treatment and/or observation.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The term "composition" is intended to encompass a product comprising the specified ingredients in the specified amounts, as well as any product that results, directly or indirectly, from combinations of the specified ingredients in the specified amounts.

The term "pharmaceutically acceptable salt" is a salt of an inventive compound. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound of the invention carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include but are not limited to: acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxyethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like.

The term "pharmaceutically acceptable carrier" is a medium that is used to prepare a desired dosage form of the inventive compound. A pharmaceutically acceptable carrier includes solvents, diluents, or other liquid vehicle; dispersion or suspension aids; surface active agents; isotonic agents; thickening or emulsifying agents, preservatives; solid binders; lubricants and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe, ed. (Amer. Pharmaceutical Assoc. 2000), both of which are incorporated herein by reference in their entireties, disclose various carriers used in formulating pharmaceutical compositions and known techniques for the preparation thereof.

As used herein, the term "aliphatic" refers to saturated and unsaturated straight chained, branched chain, cyclic, or polycyclic hydrocarbons that may be optionally substituted at one or more positions. Illustrative examples of aliphatic groups include alkyl, alkenyl, alkynyl, cycloalkyl, cycloalkenyl, and cycloalkynyl moieties. The term "alkyl" refers to straight or branched chain saturated hydrocarbon substituent. "Alkenyl" refers to a straight or branched chain hydrocarbon substituent with at least one carbon-carbon double bond. "Alkynyl" refers to a straight or branched chain hydrocarbon substituent with at least one carbon-carbon triple bound.

The term "aryl" refers to monocyclic or polycyclic groups having at least one aromatic ring structure that optionally include one or more heteroatoms and preferably include three to fourteen carbon atoms. Aryl substituents may optionally be substituted at one or more positions. Illustrative examples of aryl groups include but are not limited to: furanyl, imidazolyl, indanyl, indenyl, indolyl, isooxazolyl, isoquinolinyl, naphthyl, oxazolyl, oxadiazolyl, phenyl, pyrazinyl, pyridyl, pyrimidinyl, pyrrolyl, pyrazolyl, quinolyl, quinoxalyl, tetrahydronaphthyl, tetrazolyl, thiazolyl, thienyl, benzothiazolyl, and the like.

The aliphatic (i.e., alkyl, alkenyl, etc.) and aryl moieties may be optionally substituted with one or more substituents, preferably from one to five substituents, more preferably from one to three substituents, and most preferably from one to two substituents. The definition of any substituent or variable at a particular location in a molecule is independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein. Examples of suitable substituents include but are not limited to: alkyl, alkenyl, alkynyl, aryl, halo; trifluoromethyl; trifluoromethoxy; hydroxy; alkoxy; cycloalkoxy; heterocyclooxy; oxo; alkanoyl (—C(=O)-alkyl which is also referred to as "acyl")); aryloxy; alkanoyloxy; amino; alkylamino; arylamino; aralkylamino; cycloalkylamino; heterocycloamino; disubstituted amines in which the two amino substituents are selected from alkyl, aryl, or aralkyl; alkanoylamino; aroylamino; aralkanoylamino; substituted alkanoylamino; substituted arylamino; substituted aralkanoylamino; thiol; alkylthio; arylthio; aralkylthio; cycloalkylthio; heterocyclothio; alkylthiono; arylthiono; aralkylthiono; alkylsulfonyl; arylsulfonyl; aralkylsulfonyl; sulfonamido (e.g., $SO_2NH_2$); substituted sulfonamido; nitro; cyano; carboxy; carbamyl (e.g., $CONH_2$); substituted carbamyl (e.g., —C(=O)NRR' where R and R' are each independently hydrogen, alkyl, aryl, aralkyl and the like); alkoxycarbonyl, aryl, substituted aryl, guanidino, and heterocyclo such as indoyl, imidazolyl, furyl, thienyl, thiazolyl, pyrrolidyl, pyridyl, pyrimidyl and the like. Where applicable, the substituent may be further substituted such as with, alkyl, alkoxy, aryl, aralkyl, halogen, hydroxy and the like.

The terms "alkylaryl" or "arylalkyl" refer to an aryl group with an aliphatic substituent that is bonded to the compound through the aliphatic group. An illustrative example of an alkylaryl or arylalkyl group is benzyl, a phenyl with a methyl group that is bonded to the compound through the methyl group (—$CH_2$Ph where Ph is phenyl).

The term "alkoxy" refers to —OR wherein O is oxygen and R is an aliphatic group.

The term "aminoalkyl" refers to —$RNH_2$ where R is an aliphatic moiety.

The terms "halogen," "halo", or "halide" refer to fluorine, chlorine, bromine and iodine.

The term "haloalkyl" refers to —RX where R is an aliphatic moiety and X is one or more halogens.

The term "hydroxyalkyl" refers to —ROH where R is an aliphatic moiety.

The term "oxo" refers to a carbonyl oxygen (=O).

In addition to the explicit substitutions at the above-described groups, the inventive compounds may include other substitutions where applicable. For example, the lactone or lactam backbone or backbone substituents may be additionally substituted (e.g., by replacing one of the hydrogens or by derivatizing a non-hydrogen group) with one or more substituents such as $C_1$–$C_5$ aliphatic, $C_1$–$C_5$ alkoxy, aryl, or a functional group. Illustrative examples of suitable functional groups include but are not limited to: acetal, alcohol, aldehyde, amide, amine, boronate, carbamate, carboalkoxy, carbonate, carbodiimide, carboxylic acid, cyanohydrin, disulfide, enamine, ester, ether, halogen, hydrazide, hydrazone, imide, imido, imine, isocyanate, ketal, ketone, nitro, oxime, phosphine, phosphonate, phosphonic acid, quaternary ammonium, sulfenyl, sulfide, sulfone, sulfonic acid, thiol, and the like.

The term "purified," as used in reference to a compound of the present invention, means that the compound is in a preparation in which the compound forms a major component of the composition, such as constituting about 50%, about 60%, about 70%, about 80%, about 90%, about 95% or more by weight of the components in the composition.

MODES OF CARRYING OUT THE INVENTION

In one aspect of the present invention, a novel compound, whose structure is shown below,

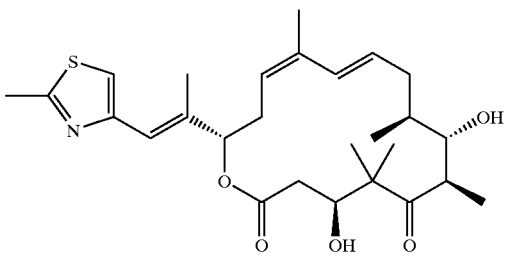

is provided. This compound is referred to herein as 10,11-dehydroepothilone D. 10,11-dehydroepothilone D was first identified during the purification of epothilone D produced by the recombinant strain of *Myxococcus xanthus*, K111-40-1. This strain expresses the epothilone polyketide synthase but not an active epoK gene product and so produces primarily epothilone D and epothilone C. Strain K111-40-1 (PTA-2712) was deposited in the American Type Culture Collection ("ATCC"), 10801 University Blvd., Manassas, VA, 20110-2209 USA on Nov. 21, 2000.

Example 1 describes a fermentation protocol for strain K111-40-1. Example 2 describes the purification protocol for epothilone D that led to the identification of 10,11-dehydroepothilone D, originally designated as "Epo490". Example 3 describes the purification of Epo490 from an enriched epothilone D crystallization side stream that led to its identification as 10,11-dehydroepothilone D. Example 4 describes the purification of 10,11-dehydroepothilone D from a fermentation of strain K111-40-1. Example 5 describes cell-based assays demonstrating the biological activity of 10,11-dehydroepothilone D.

10,11-dehydroepothilone D may also be isolated from other host cells that make epothilone compounds. For example, *M. xanthus* strain K111-72-4.4 expresses the epothilone polyketide synthase and contains an epoK gene with an inactivating in frame deletion. Strain K111-72-4.4 (PTA-2713) was deposited in the ATCC on Nov. 21, 2000. In Example 6, the construction of an *M. xanthus* strain that makes 10,11-dehydroepothilone D is described. The protocol involves inactivation of the enoyl reductase ("ER") of extender module five in the epoD gene in a strain in which the epoK gene has already been inactivated or deleted. In another example, *M. xanthus* strains that express the epothilone polyketide synthase (e.g. K111-40-1 or K111-72-4.4) may be mutated using radiation and/or chemical mutagens and screened for strains in which the ER domain of extender module five has been inactivated. These *M. xanthus* strains also may be fermented using conditions similar to those described by Example 1.

It also may be possible to isolate 10,11-dehydroepothilone D from *Sorangium cellulosum* strain So ce90 from which epothilones were first extracted or from naturally occurring or recombinant mutated versions of such strains. Deposits of *S. cellulosum* strain So ce90 exist at the German Collection of Microorganisms as DSM 6773 (PCT publication WO 93/10121) and DSM 11999 (PCT publication WO 99/42602), a mutated version of DSM 6773 which allegedly displays increased production of epothilones A and B over the wild type strain. Fermentation conditions for Sorangium can be based on the protocols described in PCT Patent Publication Nos. WO 93/10121, WO 97/19086, WO 98/22461, and WO 99/42602 and a publication by Gerth et al., 1996, *The Journal of Antibiotics*, 49: 560–563, each of which is incorporated herein by reference. Sorangium strains may be mutated as described above for *M. xanthus* to generate a srtain that produces 10,11-dehydroepothilone D or analogs thereof.

10,11-dehydoepothilone D may also be made using de novo chemical synthesis, for example, from two fragments designated as Fragment A and Fragment B. Methods for making 10,11-dehydroepothilone D and related compounds are another aspect of the present invention Example 7 describes the synthesis of Fragment A. Examples 8 and 9 describe the synthesis of Fragments B1 and B2 respectively. Fragments A and B1 can be joined together in a Heck coupling reaction, the product of which is then cyclized to form 10,11-dehydroepothilone D. Alternatively, Fragments A and B2 can be joined together in a Suzuki coupling reaction, the product of which is then cyclized to form 10,11-dehydroepothilone D. Both the Heck and Suzuki coupling routes to 10,11-dehydroepothilone D are described in Example 10.

In another aspect of the present invention, 21-hydroxy-10,11-dehydroepothilone D, whose structure is shown below,

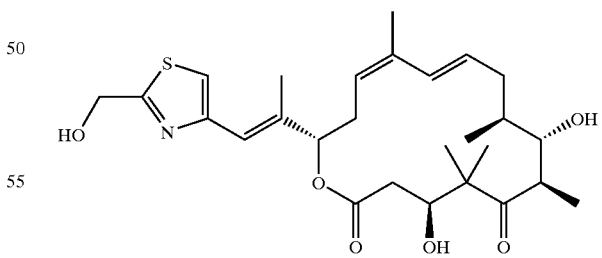

is provided. This compound can be made using a microbially-derived hydroxylase to hydroxylate the terminal methyl group of the thiazole moiety of 10,11-dehydroepothilone D. Exemplary protocols for effecting such a transformation are described by PCT Publication No. WO 00/39276, which is incorporated herein in its entirety by reference, and by Example 11. Microbial bioconversion may also be used to generate other hydroxylated analogs of 10,11-dehydroepothilone D.

21-Hydroxy-10,11-dehydroepothilone D may also be made using de novo chemical synthesis. Example 12 describes the synthesis of a 21-hydroxy version of Fragment A, designated as Fragment A2. As described in Example 13, 21-hydroxy-10,11-dehydroepothilone D may also be synthesized using the Heck coupling or Suzuki coupling routes by joining Fragment A2 with Fragment B1 or by joining Fragment A2 with B2 respectively.

In another aspect of the present invention, compounds of the formula

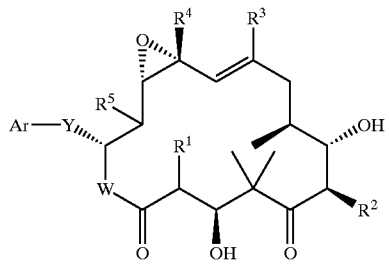

are provided. In one embodiment, these compounds may be prepared by contacting the 10,11-dehydroepothilone D analog with cells that produce the EpoK enzyme or another epoxidase, or with an epoxidase enzyme directly (i.e. in a cell free system). A general method for using EpoK for epoxidation is described by PCT Publication No. WO/31247 and by Tang et al., Science 287:640–641 (2000), each of which is incorporated herein by reference. Example 31 describes the application of this method for the epoxidation of 10,11-dehydroepothilone D into 10,11-dehydroepothilone B.

Alternatively, chemical epoxidation methods may be used to form epoxy versions of the compounds of the present invention. PCT Publication No. WO 99/43653, incorporated herein by reference, describes the use of 1,1-dimethyldioxirane in $CH_2Cl_2$ at $-50°$ C. for the selective conversion of the 12,13-alkene of epothilones C and D to the 12,13-epoxide.

Synthetic Methods

General principles of organic chemistry including functional moieties and reactivity and common protocols are described by for example in Advanced Organic Chemistry 3rd Ed. by Jerry March (1985) which is incorporated herein by reference in its entirety. In addition, it will be appreciated by one of ordinary skill in the art that the synthetic methods described herein may use a variety of protecting groups whether or not they are explicitly described. A "protecting group" as used herein means a moiety used to block functional moiety such as oxygen, sulfur, or nitrogen so that a reaction can be carried out selectively at another reactive site in a multifunctional compound. General principles including specific functional groups and their uses are described for example in T. H. Greene and P. G. M. Wuts, Protective Groups in Organic Synthesis, 3rd edition, John Wiley & Sons, New York (1999).

In one aspect of the present invention, two fragments are coupled together and subsequently cyclized to form 16 membered macrocycles of the present invention. In one embodiment, fragments A and B are joined together under Heck coupling conditions (a palladium catalyst such as (diphenylphosphineferrocenyl)dichloropalladium or tris (dibenzylidenacetone)-dipalladium; a base such as cesium carbonate or triethylamine; and triphenylarsine or triphenylphosphine). In another embodiment, fragments A and B' (an alkyne form of fragment B) are joined together under Suzuki coupling reaction conditions. Fragment B' is treated with a borane such as catechol borane or 9-borabicyclo[3.3.1]nonane, and then fragments B' and A, a palladium catalyst such as (diphenylphosphineferrocenyl)-dichloropalladium, a base such as cesium carbonate, and triphenylarsine are reacted together. Both methods are illustrated schematically by Scheme 1 where Ar, W, Y, $R^1$, $R^2$, $R^3$, $R^4$, $R^5$ are as described previously and Z is a protected hydroxy group or a protected amino group that is capable of becoming W upon deprotection and cyclization.

SCHEME 1

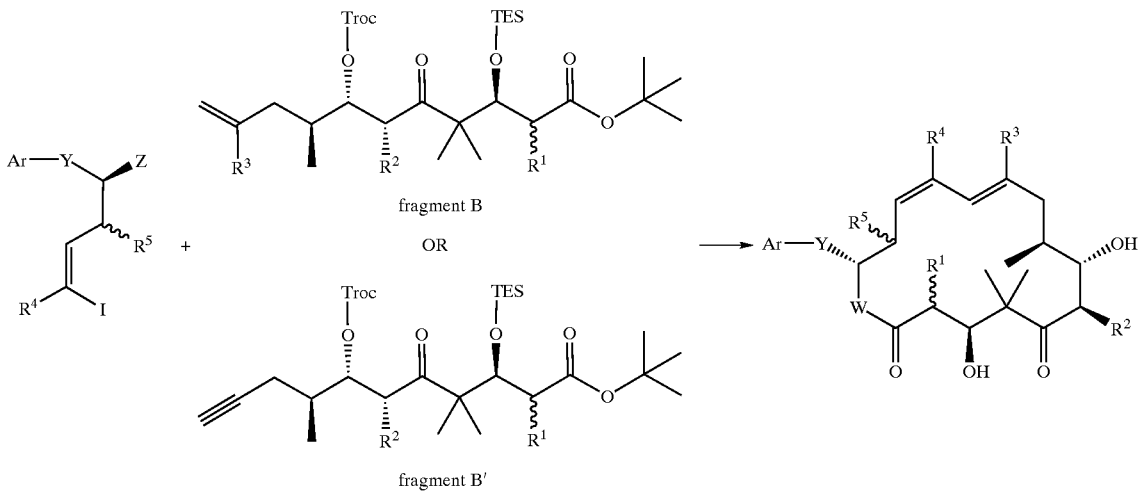

These routes are described in more detail in Example 10.

Fragment A is made using a number of methods. Scheme 2A illustrates one embodiment where $R^5$ is hydrogen, Z is a protected hydroxy group, and Ar-Y and $R^4$ are as described previously.

SCHEME 2A

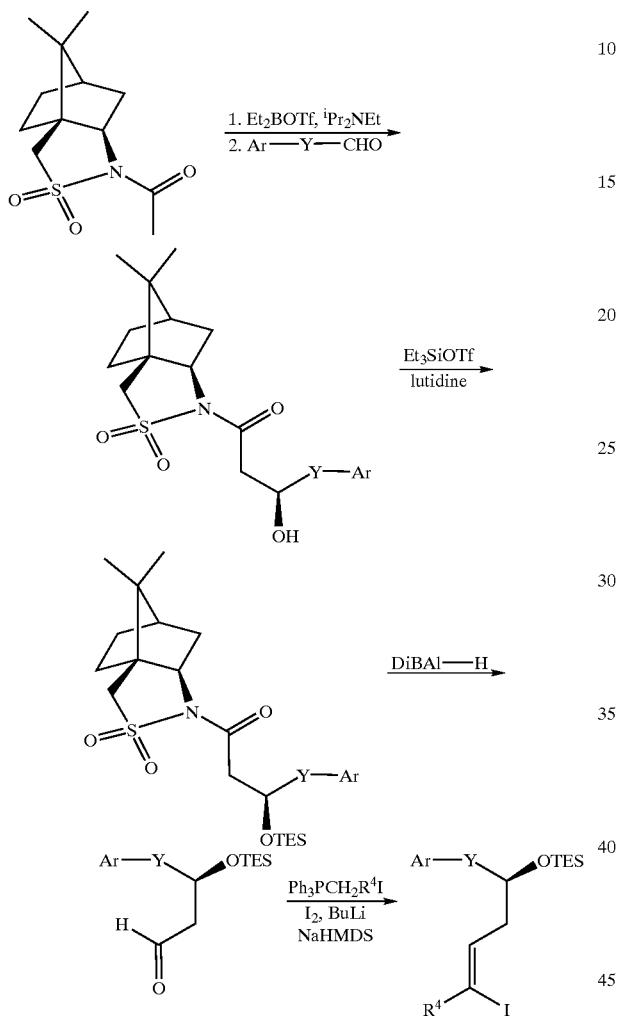

Briefly, (2R)-N-acetyl-2,10-camphorsultam is treated with a dialkylboron triflate such as diethylborontriflate and a base such as diisopropylethylamine and then reacted with Ar-Y-CHO in an Oppolzer aldol condensation. The resulting alcohol is protected by reacting the compound with triethylsilyl triflate and lutidine, and then reduced with diisobutylaluminum hydride to form the aldehyde. Fragment A is formed by extending the aldehyde in a Wittig reaction by treating the aldehyde with an iodinated ylid formed by reacting a phosphonium salt such as iodoethyltriphenylphosphonium iodide with a strong base such as sodium hexamethyldisilazide (NaHMDS). Iodoethyltriphenylphosphonium iodide is prepared in situ by treating ethyltriphenylphosphonium iodide sequentially with n-butyllithium and iodine. This embodiment is exemplified below in Examples 14 and 15.

Scheme 2B illustrates another embodiment where Ar-Y, $R^4$ and $R^5$ are as described previously. This method is preferred where $R^5$ is a non-hydrogen moiety.

SCHEME 2B

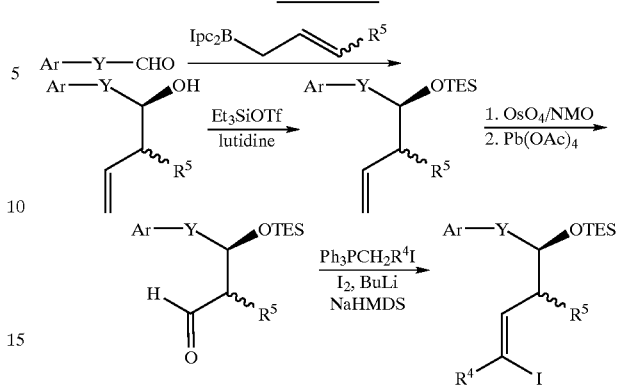

Aldehyde Ar-Y-CHO is treated with diisopinocampheyl-allylborane in a Brown asymmetric allylation. The resulting alcohol is protected with triethylsilyl triflate and lutidine and the alkene is oxidized to an aldehyde. The aldehyde is extended as in Scheme 2A in a Wittig reaction with an iodinated ylid. The appropriate stereochemistry of the $R^5$ group is achieved by selecting the chirality of the diisopinocampheyl-allylborane. Thus, use of (+)-diisopinocampheyl-trans-crotylborane results in formation of the Fragment A wherein $R^5$ is a methyl group having the (S)-configuration (Scheme 2C).

SCHEME 2C

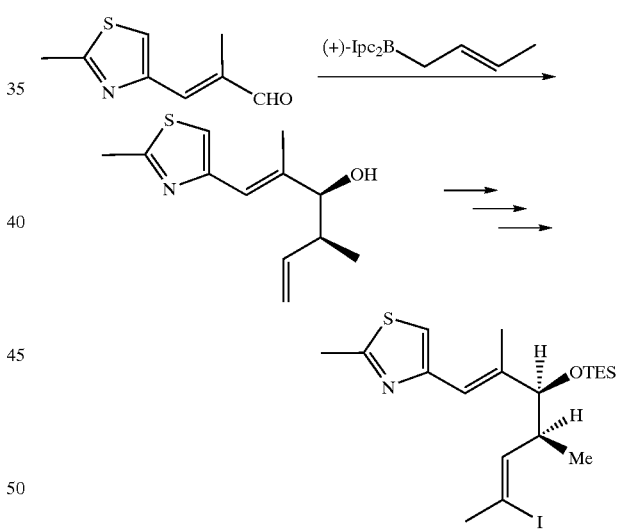

This embodiment is exemplified below in Example 17.

Scheme 3 illustrates another embodiment where Z is a protected amino group and Ar-Y, $R^4$ and $R^5$ are as described previously.

SCHEME 3

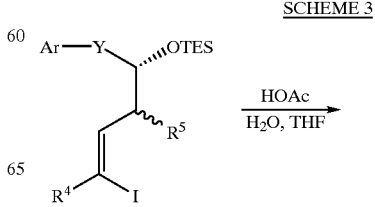

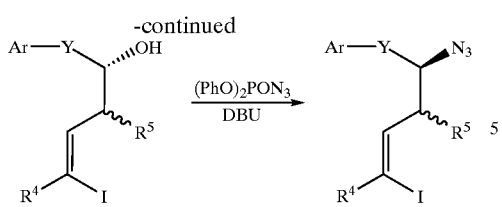

Briefly, the hydroxy protected form of fragment A of the opposite configuration as that described in Schemes 2A and 2B is deprotected and treated with diphenylphosphoryl azide and diazabicycloundecene to form the azido-version of fragment A. This embodiment is exemplified below in Examples 18 and 19.

Fragment B where $R^1$ is hydrogen is prepared as described by Scheme 4A.

SCHEME 4A

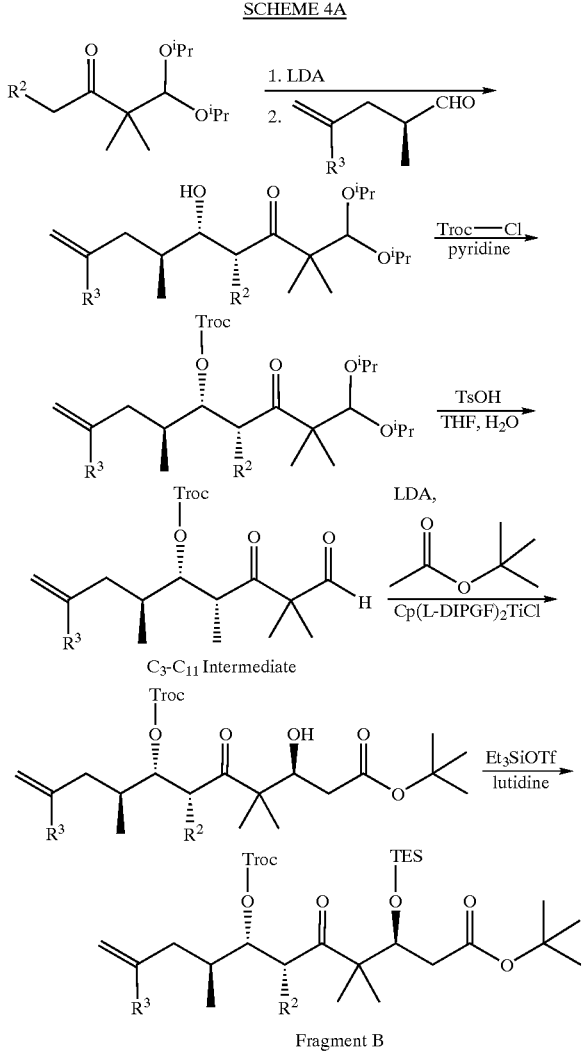

Fragment B

A 1,1-diisopropoxy-2,2-dimethyl-3-alkanone is extended in an aldol condensation reaction. The resulting hydroxyl group is protected with trichloroethoxycarbonyl chloride, and the acetal protecting group is removed to yield a $C_3$–$C_{11}$ Intermediate of fragment B. This intermediate aldehyde is extended in another aldol reaction and protected to yield fragment B. This embodiment is exemplified below in Example 8.

Fragment B' (where $R^3$ is hydrogen) and where $R^1$ is hydrogen is prepared as described by Scheme 4B.

SCHEME 4B

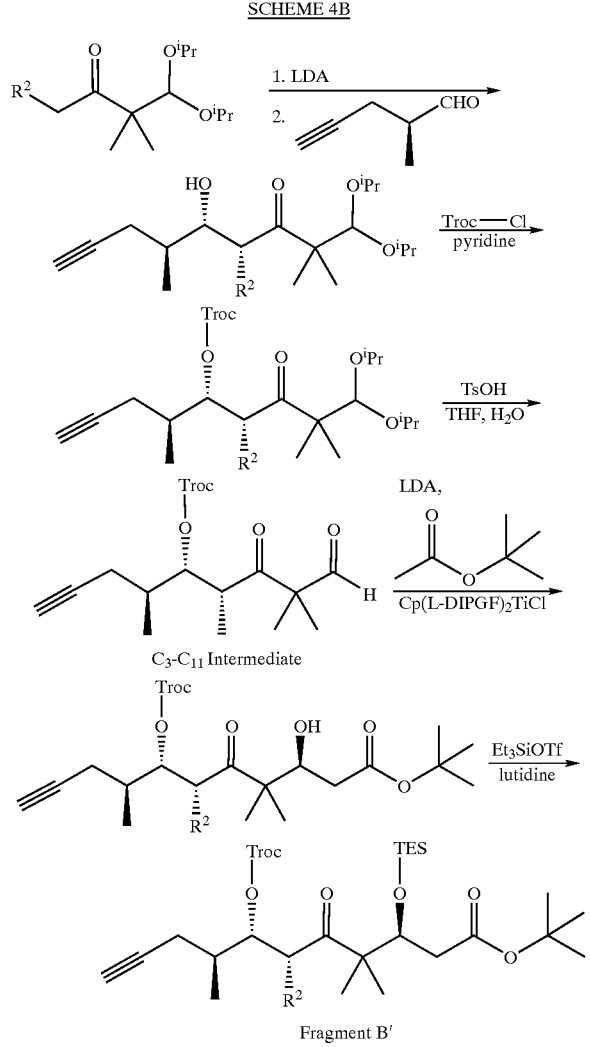

Fragment B'

The method is similar to that described by Scheme 4A except that the first aldol reaction is performed using the alkynal

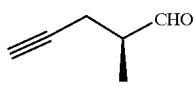

instead of the alkenal

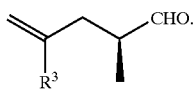

This embodiment is exemplified below in Example 9.

Fragments B and B' where $R^1$ is a non-hydrogen is prepared as described by Scheme 5.

SCHEME 5

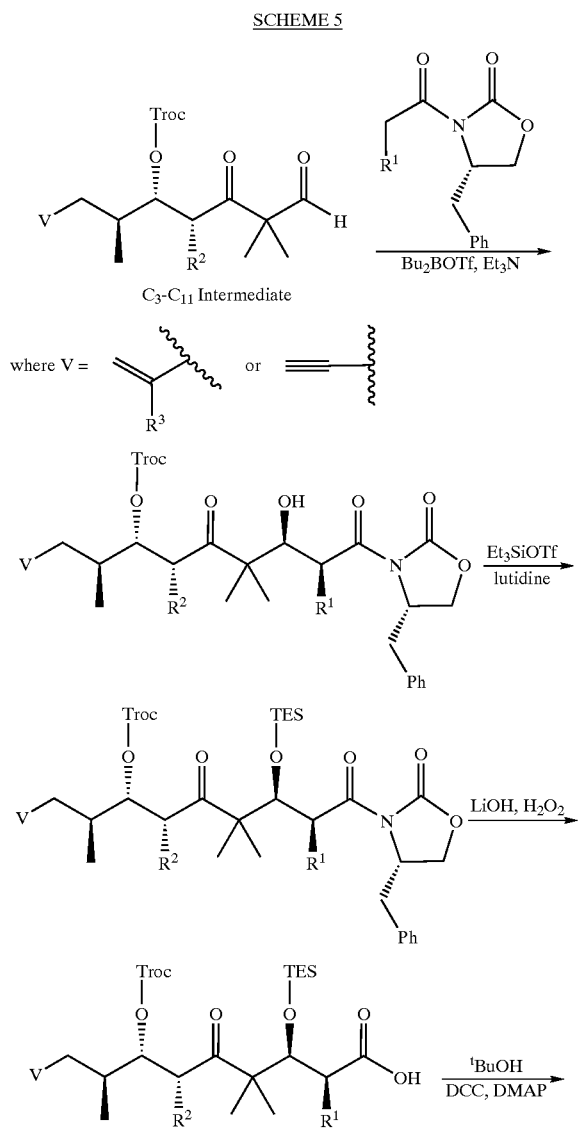

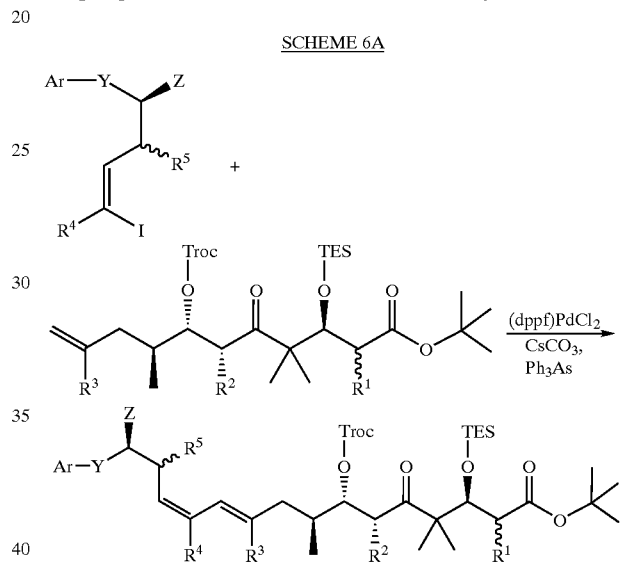

The alkene and alkyne versions of the $C_3$–$C_{11}$ Intermediate are prepared as described by Schemes 4A and 4B respectively. The $C_3$–$C_{11}$ Intermediate is treated with N-propionyl-benzyloxazolidinone in an Evans aldol reaction. The resulting alcohol is protected with the silyl group and then the benzyloxazolidinone is hydrolyzed. Esterification with with tert-butanol yields fragment B. This embodiment is exemplified below in Example 21.

Fragments A and B can be joined together in a Heck coupling reaction to form a diene as shown by Scheme 6A.

SCHEME 6A

Alternatively, Fragments A and B' can be joined together in a Suzuki coupling reaction to form the same diene as shown by Scheme 6B.

SCHEME 6B

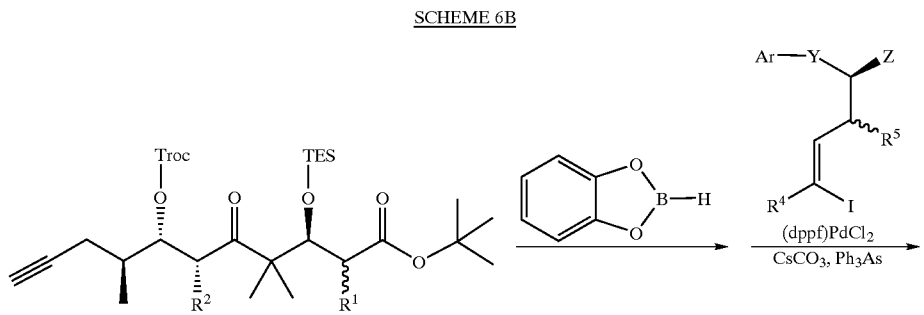

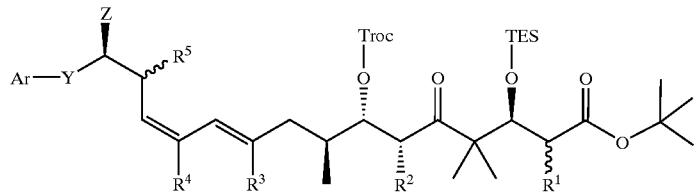

Compounds of the present invention that are cyclic lactones are made from the coupling of fragment A (where Z is a protected hydroxyl group) and fragment B (or B') as illustrated by Scheme 7A.

SCHEME 7A

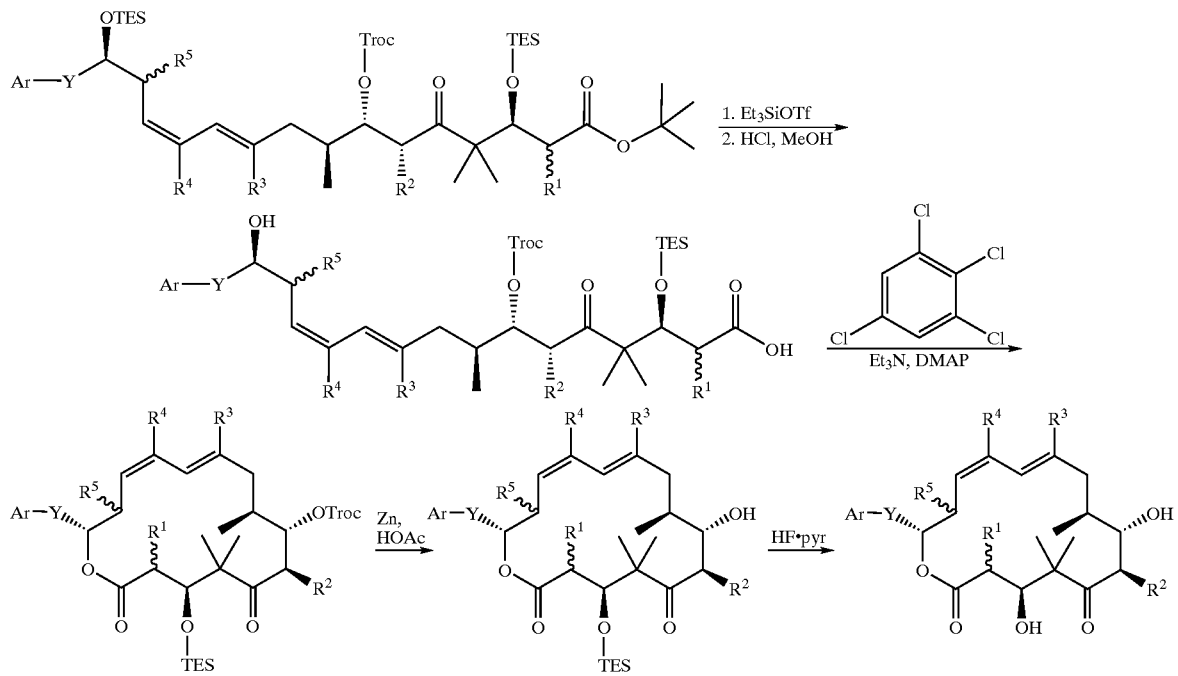

The diene product of either the Heck coupling of fragments A and B or the Suzuki coupling of fragments A and B' is subjected to an ester exchange and then partially deprotected. The resulting product is lactonized and deprotected to yield compounds corresponding to formula I where W is O. This embodiment is exemplified below in Example 10.

Compounds of the present invention that are cyclic lactams are made from the coupling of fragment A (where Z is a protected amino group such as $N_3$) and fragment B (or B') as illustrated by Schemes 7B and 7C.

SCHEME 7B

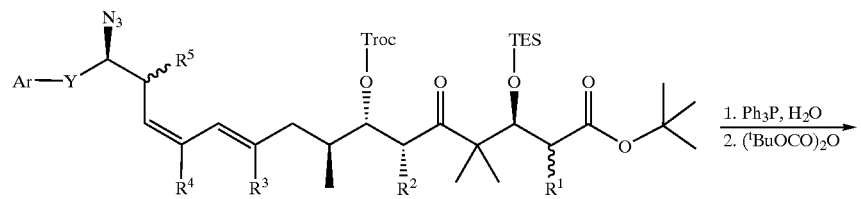

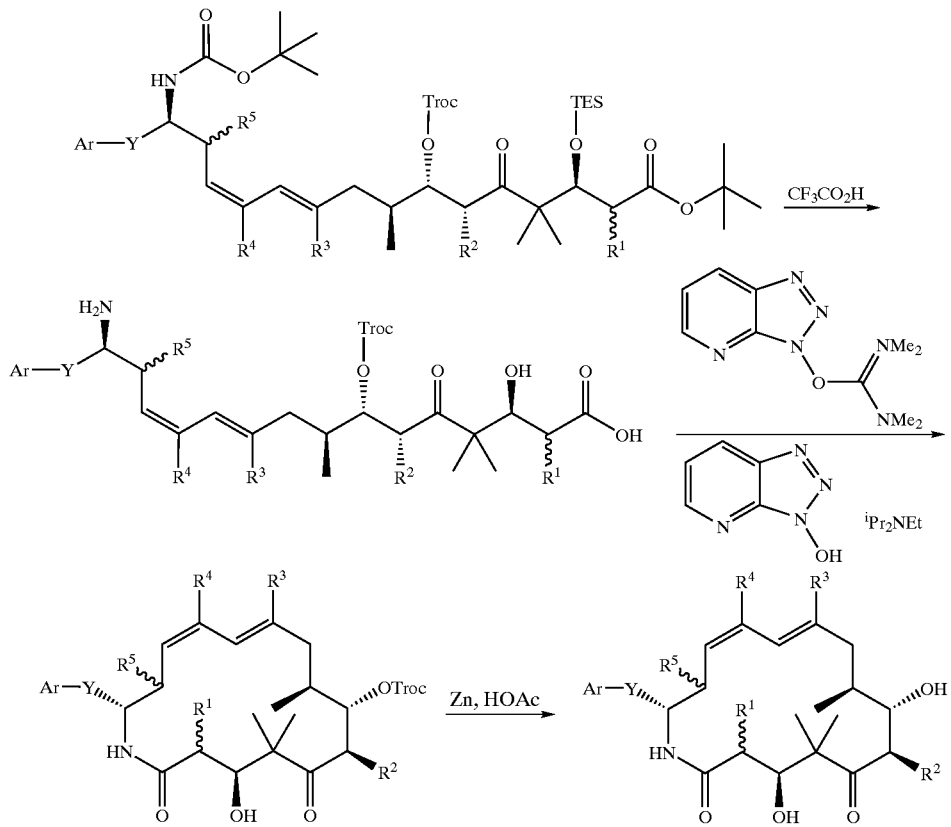

The diene product of either the Heck coupling of fragments A and B or the Suzuki coupling of fragments A and B' is subjected to a Staudinger reduction and the resulting amine is protected. The resulting product is treated with trifluoroacetic acid and then cyclized to form the cyclic lactam. Deprotection of the Troc protecting group yields compounds corresponding to formula I where W is NH. This embodiment is exemplified below in Examples 28 and 29.

Methods for making N-alkyl lactam derivatives are described by Scheme 7C.

SCHEME 7C

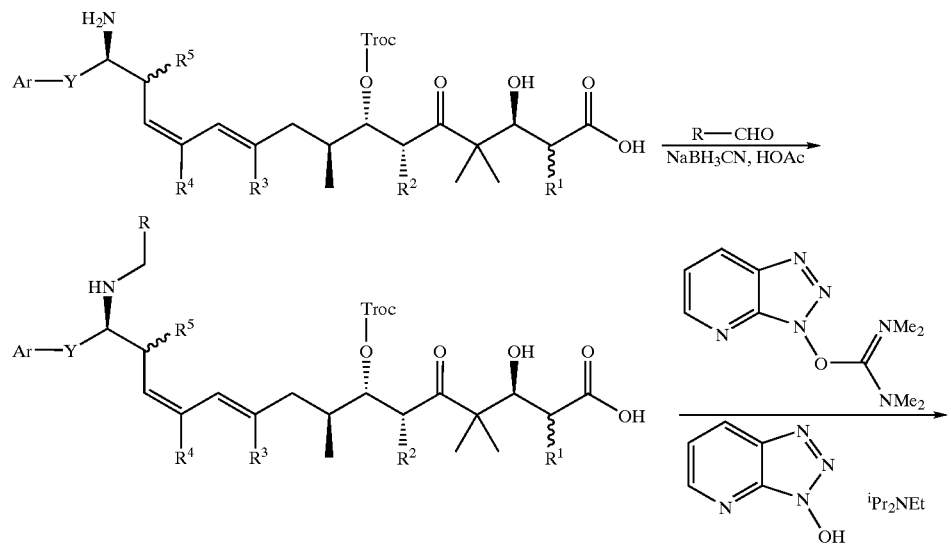

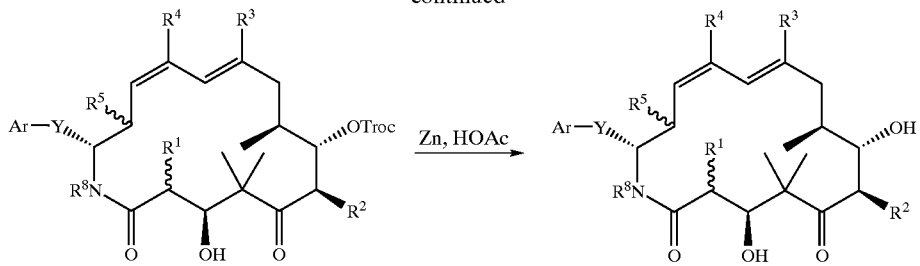

The amino-carboxyacid is made as described by Scheme 7B and then subjected to reductive amination. The resulting product is then cyclized and deprotected to yield compounds corresponding to formula I where W is $NR^8$. This embodiment wherein $R^8$ is methyl is exemplified below in Example 30.

In another aspect of the present invention, the inventive compounds are made from modified versions of fragments A and B (designated as A" and B") using Stille coupling.

SCHEME 8

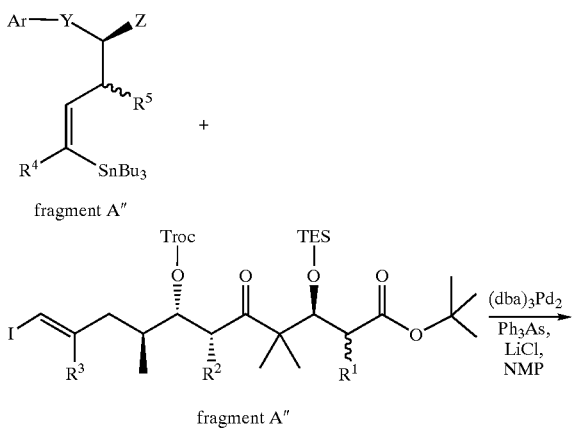

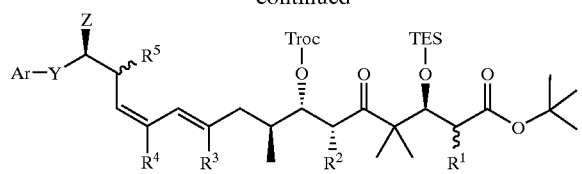

As shown by Scheme 8, the Stille coupling reaction of fragments A" and B" makes the same intermediate as that produced from the previously described Heck coupling or Suzuki coupling reactions. This intermediate can be cyclized under conditions similar to that described by Schemes 7A, 7B, and 7C to make the compounds of the present invention.

Fragment A" can be made as described by Scheme 9 by stannylation of fragment A.

SCHEME 9

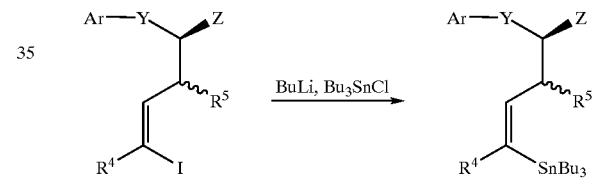

Fragment B" where $R^3$ is hydrogen is made by can be made starting with fragment B'.

SCHEME 10A

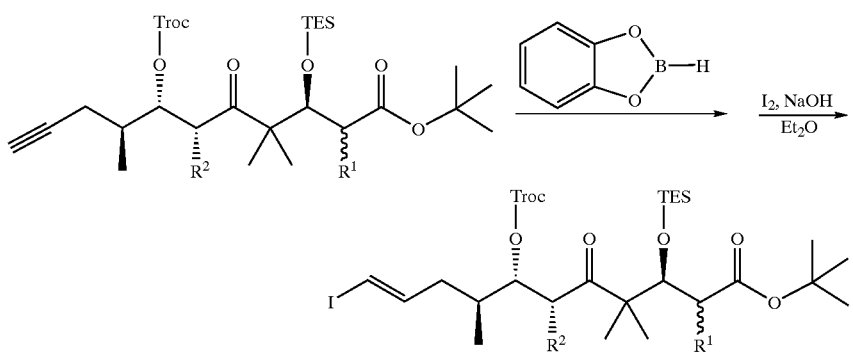

As shown by Scheme 10A, fragment B' is treated with catechol borane in a hydroboration reaction and then iodinated to yield fragment B" where $R^3$ is hydrogen.

Fragment B" where $R^3$ is a non-hydrogen is also made starting from fragment B'

SCHEME 10B

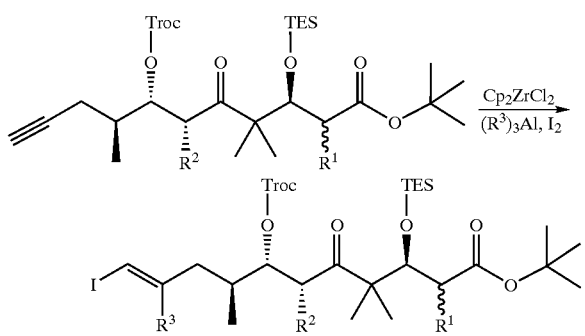

As shown by Scheme 10B, fragment B' is treated wtih zirconocene dichloride and trialkylaluminum in a Schwartz reaction to yield fragment B" where $R^3$ is alkyl.

Biological Methods

In another aspect of the present invention, a subset of the inventive compounds is made using biological methods. In one embodiment, 10,11-dehydroepothilone D is isolated from a strain of *Myxococcus xanthus*, K111-40-1. This strain expresses the epothilone polyketide synthase but not an active epoK gene product so produces primarily epothilone D and lesser amounts of epothilone C and 10,11-dehydroepothilone D. Strain K111-40-1 (PTA-2712) was deposited with the American Type Culture Collection ("ATCC"), 10801 University Blvd., Manassas, VA, 20110-2209 USA on Nov. 21, 2000. In another embodiment, 10,11-dehydroepothilone D may be isolated from *M. xanthus* strain K111-72-4.4 that expresses the epothilone polyketide synthase and contains an epoK gene with an inactivating in frame deletion. Strain K111-72-4.4 (PTA-2713) also was deposited with the ATCC on Nov. 21, 2000. Methods for fermentation of these strains, purification of 10,11-dehydroepothilone D produced by these strains, and recombinant strains that make 10,11-dehydroepothilone D are described in related application U.S. Ser. No. 09/825,876 filed Apr. 3, 2001 by inventors Robert Arslanian, John Carney and Brian Metcalf entitled EPOTHILONE COMPOUNDS AND METHODS FOR MAKING AND USING THE SAME.

Recombinant techniques can be used to make a subset of the compounds of the present invention. These compounds include those with substitutents at the C-2 and/or C-6 and/or C-8 and/or C-10 and/or C-14 positions that differ from the naturally occurring epothilones A-D. Procedures for making these kinds of changes in heterologous hosts such as *Myxococcus xanthus*, *Steptomyces lividians*, and *Pseudomonas fluorescens* are described in U.S. Pat. No. 6,303,342 entitled RECOMBINANT METHODS AND MATERIALS FOR PRODUCING EPOTHILONE AND EPOTHILONE DERIVATIVES, which is incorporated herein by reference. Among other things, the patent provides the nucleotide sequence of the epothilone PKS and modification enzyme genes cloned from *Sorangium cellulosum* SMP44; cosmids containing overlapping fragments of the epothilone PKS and modification enzyme genes; plasmid pairs having the full complement of epoA, epoB, epoC, epoD, epoE, epoF, epoK, and epoL genes; and heterologous host cells for making epothilones and epothilone derivatives. Cosmids, pKOS35-70.1A2 (ATCC 203782), pKOS35-70.4 (ATCC 203781), pKOS35-70.8A3 (ATCC 203783), and pKOS35-79.85 (ATCC 203780); plasmid pair, pKOS039-124R (PTA-926) and pKOS039-126R (PTA-927); and strain K111-32.25 (PTA-1 700) derived from *Myxococcus xanthus* containing all the epothilone genes and their promoters, have been deposited with the ATCC on Apr. 14, 2000. Additional procedures for making epothilones in *Myxococcus xanthus* are described in: PCT Publication WO 01/83800 entitled PRODUCTION OF POLYKETIDES; U.S. Ser. No. 09/560, 367 filed Apr. 28, 2000 entitled PRODUCTION OF POLYKETIDES; U.S. Ser. No. 60/232,696 filed Sep. 14, 2000 entitled PRODUCTION OF POLYKETIDES; U.S. Ser. No. 60/257,517 filed Dec. 21, 2000 entitled PRODUCTION OF POLYKETIDES; and U.S. Ser. No. 60/269,020 filed Feb. 13, 2001 entitled PRODUCTION OF POLYKETIDES, all of which are incorporated herein by reference.

In one embodiment of the invention, substituents such as methyl, ethyl, and methoxy may be introduced at positions 2, 4, 6, 8, 10, 12, and 14 by genetic engineering of the polyketide synthase as described in, e.g., PCT Publication WO 98/49315; PCT Publication WO 00/24907; and PCT Publication WO 00/63361, each of which is incorporated herein by reference. In brief, an acyltransferase domain of the epothilone polyketide synthase is replaced by a heterologous acyltransferase domain having a different substrate specificity. For example, to prepare 14-methyl-10,11-dehydroepothilone D, the acyltransferase of module 3 having specificity for malonyl-CoA is replaced with an acyltransferase domain having specificity for methylmalonyl-CoA. Examples of acyltransferase domains having specificity for methylmalonyl-CoA include but are not limited to domains found in the erythromycin, oleandomycin, or megalomicin polyketide synthases; domains from modules 1, 3, 4, 5, and 6 of the pikromycin polyketide synthase; domains from modules 1, 3, 4, 6, 7, 10, and 13 of the rapamycin polyketide synthase; and modules 1, 2, 4, and 6 of the tylosin or spiramycin polyketide synthases. Examples of acyltransferase domains having specificity for methoxymalonyl extender units include but are not limited to domains found in modules 7 and 8 of the FK506 and FK520 polyketide synthases. Examples of acyltransferase domains having specificity for ethylmalonyl-CoA include but are not limited to domains found in module 5 of the tylosin or spiramycin polyketide synthase, and in module 4 of the FK520 polyketide synthase.

In another embodiment of the invention, substituents such as methyl, ethyl, and methoxy may be introduced at positions 2, 4, 6, 8, 10, 12, and 14 by genetic engineering of the polyketide synthase as described in U.S. Ser. No. 60/310, 730 filed Aug. 7, 2001 entitled ALTERATION OF SUBSTRATE SPECIFICITY OF A AT DOMAIN THROUGHT SITE-SPECIFIC MUTAGENESIS. In brief, the substrate specificity of an acyltransferase domain is altered by mutation of key sequences within the domain. For example, to prepare 14-methyl-10,11-dehydroepothilone D, the acyltransferase of module 3 having specificity for malonyl-CoA is mutagenized so as to create an acyltransferase domain having specificity for methylmalonyl-CoA.

Illustrative examples of compounds that may be made using recombinant techniques include but are not limited to 2-methyl-10,11-dehydroepothilone C or D; 6-desmethyl-10, 11-dehydroepothilone C or D; 8-desmethyl-10,11-dehydroepothilone C or D; 10-methyl-10,11-dehydroepothilone C or D; and 14-methyl-10,11-dehydroepothilone C or D.

In another aspect of the present invention, biologically derived strategies are used to modify certain compounds of the present invention regardless of whether the compounds are made biologically or by de novo chemical synthesis. In one embodiment, a microbially-derived hydroxylase is used to hydroxylate a terminal alkane, particularly an alkyl substituent of the thiazole moiety of the inventive compounds. Protocols for effectuating such a transformation are described for example by PCT Publication No. WO 00/39276 which is incorporated herein in its entirety by reference. Example 26 describes in greater detail the hydroxylation of the C-20 methyl of 10,11-dehydroepothilone D to 21-hydroxy-10,11-dehydroepothilone D. This general method can be readily adapted for making corresponding 21-hydroxy derivatives from other compounds of the invention.

In another embodiment, Epo K, a P450 epoxidase that performs the epoxidation reaction in host cells that naturally produce epothilones or another epoxidase may be used to make 12,13-epoxy versions of the compounds of the present invention. A general method for using EpoK for epoxidation is described by Example 5 of PCT publication WO 00/31247 which is incorporated herein by reference. Example 27 describes in greater detail the epoxidation of 10,11-dehydroepothilone D to 10,11-dehydroepothilone B, the general method which can be readily adapted for making corresponding 12,13-epoxide derivatives from other compounds of the invention.

Alternatively, the epoxidation reaction can occur by contacting an epothilone compound containing a double bond at a position that corresponds to the bond between carbon-12 and carbon 13 to a culture of cells that expresses a functional Epo K. Such cells include the myxobacterium *Sorangium cellulosum*. In particularly preferred embodiments, the *Sorangium cellulosum* expresses Epo K but does not contain a functional epothilone polyketide synthase ("PKS") gene. Such strains may be made by mutagenesis where one or more mutations in the epothilone PKS gene render it inoperative. Such mutants can occur naturally (which may be found by screening) or can be directed using either mutagens such as chemicals or irradation or by genetic manipulation. A particularly effective strategy for making strains with an inoperative epothilone PKS is homologous recombination as described by PCT publication WO 00/31247, entitled PRODUCING EPOTHILONE AND EPOTHILONE DERIVATIVES.

Formulation

A composition of the present invention generally comprises a compound of the present invention and a pharmaceutically acceptable carrier. The inventive compound may be in free form or where appropriate as pharmaceutically acceptable derivatives such as prodrugs, and salts and esters of the inventive compound.

The composition may be in any suitable form such as solid, semisolid, or liquid form. See Pharmaceutical Dosage Forms and Drug Delivery Systems, 5th edition, Lippicott Williams & Wilkins (1991) which is incorporated herein by reference. In general, the pharmaceutical preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used.

In one embodiment, the compositions containing an inventive compound are Cremophor®-free. Cremophor® (BASF Aktiengesellschaft) is a polyethoxylated castor oil which is typically used as a surfactant in formulating low soluble drugs. However, because Cremophor® can case allergic reactions in a subject, compositions that minimize or eliminate Cremophor® are preferred. Formulations of epothilone A or B that eliminate Cremophor® are described for example by PCT Publication WO 99/39694 which is incorporated herein by reference and may be adapted for use with the inventive compounds.

Where applicable, an inventive compound may be formulated as microcapsules and nanoparticles. General protocols are described for example, by Microcapsules and Nanoparticles in Medicine and Pharmacy by Max Donbrow, ed., CRC Press (1992) and by U.S. Pat. Nos. 5,510,118; 5,534,270; and 5,662,883 which are all incorporated herein by reference. By increasing the ratio of surface area to volume, these formulations allow for the oral delivery of compounds that would not otherwise be amenable to oral delivery.

An inventive compound may also be formulated using other methods that have been previously used for low solubility drugs. For example, the compounds may form emulsions with vitamin E or a PEGylated derivative thereof as described by PCT Publications WO 98/30205 and WO 00/71163 which are incorporated herein by reference. Typically, the inventive compound is dissolved in an aqueous solution containing ethanol (preferably less than 1% w/v). Vitamin E or a PEGylated-vitamin E is added. The ethanol is then removed to form a pre-emulsion that can be formulated for intravenous or oral routes of administration. Another strategy involves encapsulating the inventive compounds in liposomes. Methods for forming liposomes as drug delivery vehicles are well known in the art. Suitable protocols include those described by U.S. Pat. Nos. 5,683,715; 5,415,869, and 5,424,073 which are incorporated herein by reference, relating to another relatively low solubility cancer drug taxol and by PCT Publication WO 01/10412, which is incorporated herein by reference, relating to epothilone B. Of the various lipids that may be used, particularly preferred lipids for making epothilone-encapsulated liposomes include phosphatidylcholine and polyethyleneglycol-derivitized distearyl phosphatidylethanolamine. Example 15 provides an illustrative protocol for making liposomes containing 10,11-dehydroepothilone D.

Yet another method involves formulating an inventive compound using polymers such as polymers such as biopolymers or biocompatible (synthetic or naturally occurring) polymers. Biocompatible polymers can be categorized as biodegradable and non-biodegradable. Biodegradable polymers degrade in vivo as a function of chemical composition, method of manufacture, and implant structure. Illustrative examples of synthetic polymers include polyanhydrides, polyhydroxyacids such as polylactic acid, polyglycolic acids and copolymers thereof, polyesters polyamides polyorthoesters and some polyphosphazenes. Illustrative examples of naturally occurring polymers include proteins and polysaccharides such as collagen, hyaluronic acid, albumin, and gelatin.

Another method involves conjugating a compound of the present invention to a polymer that enhances aqueous solubility. Examples of suitable polymers include polyethylene glycol, poly-(d-glutamic acid), poly-(l-glutarnic acid), poly-(l-glutamic acid), poly-(d-aspartic acid), poly-(l-aspartic acid), poly-(l-aspartic acid) and copolymers thereof.

Polyglutamic acids having molecular weights between about 5,000 to about 100,000 are preferred, with molecular weights between about 20,000 and 80,000 being more preferred and with molecular weights between about 30,000 and 60,000 being most preferred. The polymer is conjugated via an ester linkage to one or more hydroxyls of an inventive epothilone using a protocol as essentially described by U.S. Pat. No. 5,977,163 which is incorporated herein by reference, and by Example 16. Preferred conjugation sites include the hydroxyl off carbon-21 in the case of 21-hydroxy-10,11-dehydroepothilone D. Other conjugation sites include, for example, the hydroxyl off carbon 3 and the hydroxyl off carbon 7.

In another method, an inventive compound is conjugated to a monoclonal antibody. This strategy allows the targeting of the inventive compound to specific targets. General protocols for the design and use of conjugated antibodies are described in Monoclonal Antibody-Based Therapy of Cancer by Michael L. Grossbard, ed. (1998), which is incorporated herein by reference.

The amount of active ingredient that may be combined with the carrier materials to produce a single dosage form will vary depending upon the subject treated and the particular mode of administration. For example, a formulation for intravenous use comprises an amount of the inventive compound ranging from about 1 mg/mL to about 25 mg/mL, preferably from about 5 mg/mL to 15 mg/mL, and more preferably about 10 mg/mL. Intravenous formulations are typically diluted between about 2 fold and about 30 fold with normal saline or 5% dextrose solution prior to use.

Methods to Treat Cancer

In one aspect of the present invention, the inventive compounds are used to treat cancer. In one embodiment, the compounds of the present invention are used to treat cancers of the head and neck which include tumors of the head, neck, nasal cavity, paranasal sinuses, nasopharynx, oral cavity, oropharynx, larynx, hypopharynx, salivary glands, and paragangliomas. In another embodiment, the compounds of the present invention are used to treat cancers of the liver and biliary tree, particularly hepatocellular carcinoma. In another embodiment, the compounds of the present invention are used to treat intestinal cancers, particularly colorectal cancer. In another embodiment, the compounds of the present invention are used to treat ovarian cancer. In another embodiment, the compounds of the present invention are used to treat small cell and non-small cell lung cancer. In another embodiment, the compounds of the present invention are used to treat breast cancer. In another embodiment, the compounds of the present invention are used to treat sarcomas which includes fibrosarcoma, malignant fibrous histiocytoma, embryonal rhabdomyosocarcinoma, leiomysosarcoma, neurofibrosarcoma, osteosarcoma, synovial sarcoma, liposarcoma, and alveolar soft part sarcoma. In another embodiment, the compounds of the present invention are used to treat neoplasms of the central nervous systems, particularly brain cancer. In another embodiment, the compounds of the present invention are used to treat lymphomas that include Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma.

The method comprises administering a therapeutically effective amount of an inventive compound to a subject suffering from cancer. The method may be repeated as necessary either to mitigate (i.e. prevent further growth) or to eliminate the cancer. Clinically, practice of the method will result in a reduction in the size or number of the cancerous growth and/or a reduction in associated symptoms (where applicable). Pathologically, practice of the method will produce at least one of the following: inhibition of cancer cell proliferation, reduction in the size of the cancer or tumor, prevention of further metastasis, and inhibition of tumor angiogenesis.

The compounds and compositions of the present invention can be used in combination therapies. In other words, the inventive compounds and compositions can be administered concurrently with, prior to, or subsequent to one or more other desired therapeutic or medical procedures. The particular combination of therapies and procedures in the combination regimen will take into account compatibility of the therapies and/or procedures and the desired therapeutic effect to be achieved.

In one embodiment, the compounds and compositions of the present invention are used in combination with another anti-cancer agent or procedure. Illustrative examples of other anti-cancer agents include but are not limited to: (i) alkylating drugs such as mechlorethamine, chlorambucil, cyclophosphamide, melphalan, ifosfamide; (ii) antimetabolites such as methotrexate; (iii) microtubule stabilizing agents such as vinblastin, paclitaxel, docetaxel, and discodermolide; (iv) angiogenesis inhibitors; (v) and cytotoxic antibiotics such as doxorubicon (adriamycin), bleomycin, and mitomycin. Illustrative examples of other anti-cancer procedures include: (i) surgery; (ii) radiotherapy; and (iii) photodynamic therapy.

In another embodiment, the compounds and compositions of the present invention are used in combination with an agent or procedure to mitigate potential side effects from the inventive compound or composition such as diarrhea, nausea and vomiting. Diarrhea may be treated with antidiarrheal agents such as opioids (e.g. codeine, diphenoxylate, difenoxin, and loeramide), bismuth subsalicylate, and octreotide. Nausea and vomiting may be treated with antiemetic agents such as dexamethasone, metoclopramide, diphenyhydramine, lorazepam, ondansetron, prochlorperazine, thiethylperazine, and dronabinol. For those compositions that includes polyethoxylated castor oil such as Cremophor®, pretreatment with corticosteroids such as dexamethasone and methylprednisolone and/or $H_1$ antagonists such as diphenylhydramine HCl and/or $H_2$ antagonists may be used to mitigate anaphylaxis.

Methods of Treating of Non-cancer, Cellular Hyperproliferative Disorders

In another aspect of the present invention, the inventive compounds are used to treat non-cancer disorders that are characterized by cellular hyperproliferation (e.g., an abnormally increased rate or amount of cellular proliferation). In one embodiment, the compounds of the present invention are used to treat psoriasis, a condition characterized by the cellular hyperproliferation of keratinocytes which builds up on the skin to form elevated, scaly lesions. The method comprises administering a therapeutically effective amount of an inventive compound to a subject suffering from psoriasis. The method may be repeated as necessary either to decrease the number or severity of lesions or to eliminate the lesions. Clinically, practice of the method will result in a reduction in the size or number of skin lesions, diminution of cutaneous symptoms (pain, burning and bleeding of the affected skin) and/or a reduction in associated symptoms (e.g., joint redness, heat, swelling, diarrhea, abdominal pain). Pathologically, practice of the method will result in at least one of the following: inhibition of keratinocyte proliferation, reduction of skin inflammation (for example, by impacting on: attraction and growth factors, antigen presentation, production of reactive oxygen species and matrix metalloproteinases), and inhibition of dermal angiogenesis.

In another embodiment, the compounds of the present invention are used to treat multiple sclerosis, a condition characterized by progressive demyelination in the brain. Although the exact mechanisms involved in the loss of myelin are not understood, there is an increase in astrocyte proliferation and accumulation in the areas of myelin destruction. At these sites, there is macrophage-like activity and increased protease activity which is at least partially responsible for degradation of the myelin sheath. The method comprises administering a therapeutically effective amount of an inventive compound to a subject suffering from multiple sclerosis. The method may be repeated as necessary to inhibit astrocyte proliferation and/or lessen the severity of the loss of motor function and/or prevent or attenuate chronic progression of the disease. Clinically, practice of the method will result in improvement in visual symptoms (visual loss, diplopia), gait disorders (weakness, axial instability, sensory loss, spasticity, hyperreflexia, loss of dexterity), upper extremity dysfunction (weakness, spasticity, sensory loss), bladder dysfunction (urgency, incontinence, hesitancy, incomplete emptying), depression, emotional lability, and cognitive impairment. Pathologically, practice of the method will result in the reduction of one or more of the following, such as myelin loss, breakdown of the blood-brain barrier, perivascular infiltration of mononuclear cells, immunologic abnormalities, gliotic scar formation and astrocyte proliferation, metalloproteinase production, and impaired conduction velocity.

In another embodiment, the compounds of the present invention are used to treat rheumatoid arthritis, a multisystem chronic, relapsing, inflammatory disease that sometimes leads to destruction and ankyiosis of affected joints. Rheumatoid arthritis is characterized by a marked thickening of the synovial membrane which forms villous projections that extend into the joint space, multilayering of the synoviocyte lining (synoviocyte proliferation), infiltration of the synovial membrane with white blood cells (macrophages, lymphocytes, plasma cells, and lymphoid follicles; called an "inflammatory synovitis"), and deposition of fibrin with cellular necrosis within the synovium. The tissue formed as a result of this process is called pannus and, eventually the pannus grows to fill the joint space. The pannus develops an extensive network of new blood vessels through the process of angiogenesis that is essential to the evolution of the synovitis. Release of digestive enzymes (matrix metalloproteinases (e.g., collagenase, stromelysin)) and other mediators of the inflammatory process (e.g., hydrogen peroxide, superoxides, lysosomal enzymes, and products of arachadonic acid metabolism) from the cells of the pannus tissue leads to the progressive destruction of the cartilage tissue. The pannus invades the articular cartilage leading to erosions and fragmentation of the cartilage tissue. Eventually there is erosion of the subchondral bone with fibrous ankylosis and ultimately bony ankylosis, of the involved joint.

The method comprises administering a therapeutically effective amount of an inventive compound to a subject suffering from rheumatoid arthritis. The method may be repeated as necessary to accomplish to inhibit synoviocyte proliferation and/or lessen the severity of the loss of movement of the affected joints and/or prevent or attenuate chronic progression of the disease. Clinically, practice of the present invention will result in one or more of the following: (i) decrease in the severity of symptoms (pain, swelling and tenderness of affected joints; morning stiffniess. weakness, fatigue. anorexia, weight loss); (ii) decrease in the severity of clinical signs of the disease (thickening of the joint capsule. synovial hypertrophy, joint effusion, soft tissue contractures, decreased range of motion, ankylosis and fixed joint deformity); (iii) decrease in the extra-articular manifestations of the disease (rheumatic nodules, vasculitis, pulmonary nodules, interstitial fibrosis, pericarditis, episcleritis, iritis, Felty's syndrome, osteoporosis); (iv) increase in the frequency and duration of disease remission/symptom-free periods; (v) prevention of fixed impairment and disability; and/or (vi) prevention/attenuation of chronic progression of the disease. Pathologically, practice of the present invention will produce at least one of the following: (i) decrease in the inflammatory response; (ii) disruption of the activity of inflammatory cytokines (such as IL-I, TNFa, FGF, VEGF); (iii) inhibition of synoviocyte proliferation; (iv) inhibition of matrix metalloproteinase activity, and/or (v) inhibition of angiogenesis.

In another embodiment, the compounds of the present invention are used to prevent cellular proliferation on a prosthesis implanted in a subject by coating the prosthesis with a composition containing a compound of the present invention. In another embodiment, compounds of the present invention are used to treat atherosclerosis and/or restenosis, particularly in patients whose blockages may be treated with an endovascular stent. Atherosclerosis is a chronic vascular injury in which some of the normal vascular smooth muscle cells ("VSMC") in the artery wall, which ordinarily control vascular tone regulating blood flow, change their nature and develop "cancer-like" behavior. These VSMC become abnormally proliferative, secreting substances (growth factors, tissue-degradation enzymes and other proteins) which enable them to invade and spread into the inner vessel lining, blocking blood flow and making that vessel abnormally susceptible to being completely blocked by local blood clotting. Restenosis, the recurrence of stenosis or artery stricture after corrective procedures, is an accelerated form of atherosclerosis.

The method comprises coating a therapeutically effective amount of an inventive compound on a stent and delivering the stent to the diseased artery in a subject suffering from atherosclerosis. Methods for coating a stent with a compound are described for example by U.S. Pat. Nos. 6,156,373 and 6,120,847. Clinically, practice of the present invention will result in one or more of the following: (i) increased arterial blood flow; (ii) decrease in the severity of clinical signs of the disease; (iii) decrease in the rate of restenosis; or (iv) prevention/attenuation of the chronic progression of atherosclerosis. Pathologically, practice of the present invention will produce at least one of the following at the site of stent implanataion: (i) decrease in the inflammatory response, (ii) inhibition of VSMC secretion of matrix metalloproteinases; (iii) inhibition of smooth muscle cell accumulation; and (iv) inhibition of VSMC phenotypic dedifferentiation.

Dosage Levels

In one embodiment, dosage levels that are administered to a subject suffering from cancer or a non-cancer disorder characterized by cellular proliferation are of the order from about 1 mg/m$^2$ to about 200 mg/m$^2$ which may be administered as a bolus (in any suitable route of administration) or a continuous infusion (e.g. 1 hour, 3 hours, 6 hours, 24 hours, 48 hours or 72 hours) every week, every two weeks, or every three weeks as needed. It will be understood, however, that the specific dose level for any particular patient depends on a variety of factors. These factors include the activity of the specific compound employed; the age, body weight, general health, sex, and diet of the subject; the time and route of administration and the rate of excretion of the drug; whether a drug combination is employed in the treatment; and the severity of the condition being treated.

In another embodiment, the dosage levels are from about 10 mg/m$^2$ to about 150 mg/m$^2$, preferably from about 10 to about 75 mg/m$^2$ and more preferably from about 15 mg/m$^2$ to about 50 mg/m2 once every three weeks as needed and as tolerated. In another embodiment, the dosage level is about 13 mg/m$^2$ once every three weeks as needed and as tolerated. In another embodiment, the dosage levels are from about 1 mg to about 150 mg/m$^2$, preferably from about 10 mg/m$^2$ to about 75 mg/m$^2$ and more preferably from about 25 mg/m$^2$ to about 50 mg/m$^2$ once every two weeks as needed and as tolerated. In another embodiment, the dosage levels are from about 1 mg/m$^2$ to about 100 mg/m$^2$, preferably from about 5 mg/m$^2$ to about 50 mg/m$^2$ and more preferably from about 10 mg/m$^2$ to about 25 mg/m$^2$ once every week as needed and as tolerated. In another embodiment, the dosage levels are from about 0.1 to about 25 mg/m$^2$, preferably from about 0.5 to about 15 mg/m$^2$ and more preferably from about 1 mg/m$^2$ to about 10 mg/m$^2$ once daily as needed and tolerated.

A detailed description of the invention having been provided above, the following examples are given for the purpose of illustrating the present invention and shall not be construed as being a limitation on the scope of the invention or claims.

EXAMPLE 1

This example describes fermentation of *M. xanthus* strain K111-40-1 which produces epothilone D, epothilone C, and 10,11-dehydroepothilone D. The use of an oil-based carbon source such as methyl oleate improves yields of the epothilone compounds produced by the strain. This protocol also may be used to grow other strains of *M. xanthus* such as K111-72.4.

Maintenance of *M. xanthus* on plates

*M. xanthus* strains are maintained on CYE agar plates containing: hydrolyzed casein (pancreatic digest), 10 g/L; yeast extract, 5 g/L; agar, 15 g/L; MgSO4·7H$_2$O, 1 g/L; and 1 M MOPS (((3-N-morpholino)propane sulfonic acid)) buffer solution (pH 7.6). Colonies appear approximately 3 days after streaking out on the plates. Plates are incubated at 32° C. for the desired level of growth and then stored at room temperature for up to 3 weeks (storage at 4° C. can kill the cells).

Cell Banking of Oil adapted *Myxococcus xanthus*

A non-oil adapted colony from a CYE plate or a frozen vial of cells is transferred into a 50 mL glass culture tube containing 3 mL of CYE seed media and 1 drop of methyl oleate from a 100 μL pipet. Cells are allowed to grow for 2–6 days (30° C., 175 rpm) until the culture appears dense under a microscope. When tube culture is sufficiently dense, the entire contents of the tube is transferred into a sterile 250 mL shake flask containing 50 mL of CYE-MOM seed media (hydrolyzed casein (pancreatic digest), 10 g/L; yeast extract 5 g(L; MgSO4·7H$_2$O, 1 g/L; and methyl oleate 2 ml/L). After 48±12 hours of growth (30° C., 175 rpm), 5 mL of this seed culture is transferred into 100 mL of CYE-MOM in a 500 mL shake flask. This culture is allowed to grow for 1 day (30° C., 175 rpm). 80 mL of this seed culture is combined with 24 mL of sterile 90% glycerol in a sterile 250 mL shake flask, mixed and aliquoted into 1 mL portions in cryovials. The cryovials are frozen and stored in a −80° C. freezer.

XAD-16 Resin Preparation for Fermentations

XAD resin is thoroughly with 100% methanol to remove any monomers present on the virgin resin. Approximately two times the amount of methanol in liters as the weight of the resin in kilograms (i.e. 6 liters of methanol for 3 kilograms of XAD-16) is used and the resulting slurry is stirred gently to minimize resin fragmentation. The resin is allowed to settle for at least 15 minutes before the methanol is drained to approximately a 0.5 to 1 inch layer of methanol above the XAD bed. The XAD and methanol is then transferred from the mixing container to an Amicon VA250 column, washed with at least 5 column volumes of methanol at 300±50 cm/hr, and washed with at least 10 column volumes of deionized water at 300±50 cm/hr.

Inocula Scaleup

A frozen cell bank vial of the methyl oleate adapted cells is thawed and transferred into a 50 mL glass culture tube containing 3 mL of the CYE-MOM seed media. The tube is placed in a shaker (30° C., 175 rpm), and grown for 48±24 hours. The entire contents of the culture tube is transferred into a 250 mL shake flask containing 50 mL of CYE-MOM seed media, the flask is placed in a shaker (30° C., 175 rpm) and grown for 48±24 hours. Further seed expansions are performed as necessary for use as the fermentor inoculum. In general, the production fermentation is inoculated at about 5% of the combined initial volume (seed and production medium).

1000L Fermentation

From the frozen cell bank, the cells are successively expanded into a 50 mL glass culture tube, 250 ml shake flask, 2.8 L Fembach flask, 10 L fermentor, and 150 L fermentor. The initial agitation rate of the fermentors is set at 400 rpm, and the sparging rate is maintained at 0.1 v/vim. The pH is controlled at 7.4 by addition of 2.5 N potassium hydroxide and 2.5 N sulfuric acid. The temperature is set at 30° C. and the dissolved oxygen is maintained at or above 50% of saturation by cascading the stir rate between 400–700 rpm. The production media used in the 1000L fermentor is CTS-MOM production media and comprises: hydrolyzed casein (pancreatic digest), 5 g/L; MgSO4·7H$_2$O, 1 g/L; XAD-16, 20 g/L; trace elements solution 4 mL/L; and methyl oleate 2 ml/L. Trace elements solution comprises: concentrated H$_2$SO$_4$, 10 mL/L; FeCl$_3$·6H$_2$O, 14.6 g/L; ZnCl$_2$, 2.0 g/L; MnCl$_2$·4H$_2$O, 1.0 g/L; CuCl$_2$·2H$_2$O, 0.42 g/L; H$_3$BO$_3$, 0.31 g/L; CaCl2·6H$_2$O, 0.24 g/L; and Na$_2$MoO$_4$·2H$_2$O, 0.24 g/L.

The 1000 L fermentor is prepared for epothilone production by sterilizing 555 L of water containing 16.5 kg of XAD-16 in the fermentor for 45 minutes at 121° C. Trace elements solution and MgSO$_4$ are filter sterilized through a presterilized 0.2 micron polyethersulfone membrane capsule filter directly into the fermentation vessel. Approximately 3 kg of casitone (from a 150 g/L feed solution) and 1.2 kg of methyl oleate were added to the vessel from a single presterilized feed tank. Water is filtered into the vessel (through the same capsule filter) to bring final volume to 600 L. Agitation rate is 150–200 rpm. Backpressure is maintained at 100 mbar. Dissolved oxygen is controlled at 50% of saturation by cascading the airflow (23 Lpm–50 Lpm). The pH setpoint is maintained at 7.4 by automated addition of 2.5N KOH and 2.5N H$_2$SO$_4$. The fermentor is inoculated with 32L seed from the 150L fermentor (5% volume/volume). The cells are fed hourly (24 times a day) for a total addition of 1.9 L/day of methyl oleate and 8.6 kg/day of the casitone feed solution (150 g/L), except on the day the fermentor is harvested. The bioreactor is harvested 11 days following inoculation.

EXAMPLE 2

This example describes the purification of epothilone D from Fermentation Run 1117000-1K, which led to the identification of Epo490, a novel epothilone compound of the present invention.

Step 1: XAD Elution (K125–182)

Seventeen liters (17 L) of XAD-16 resin were filtered from the fermentation culture using a Mainstream filtration unit with a thirteen-liter 150 μm capture basket. The captured XAD resin was packed into an Amicon VA250 column and was washed with 58 L (3.4 column volumes) of water at 1.0 L/min. The epothilone D product was then eluted from the resin using 170 L of 80% methanol in water. During the water wash and the first column volume of elution, the column backpressure increased steadily to above 3 bars with a final flow rate of under 300 mL/min. Therefore, the XAD resin was removed from the column and repacked into an alternate Amicon VA250 column. After the exchange, the backpressure decreased below 1 bar and the flow rate was maintained at 1.0 L/min. A single 170-L fraction was collected in a 600-L stainless steel tank. Based on HPLC analysis, the step 1 product pool was found to contain 8.4 g of epothilone D.

Step 2: Solid Phase Extraction (K145–150)

Fifty-seven liters (57 L) of water were added to the step 1 product pool (170 L) to dilute the loading solvent to 60% methanol in water. The resulting suspension (227 L) was stirred with an overhead lightning mixer and loaded onto an Amicon VA180 column packed with 6.5-L of HP20SS resin that had previously been equilibrated with 5 column volumes of 60% methanol. The loading flow rate was 1 L/min. After loading, the column was washed with 16 L of 60% methanol and eluted with 84 L of 75% methanol at a flow rate of 300 mL/min. Seven fractions were collected with volumes of 18 L, 6 L, 6 L, 6 L, 36 L, 6 L, and 6 L, respectively. Fractions 4 and 5, which contained a total of 8.8 g of epothilone D, were pooled together.

Step 3: Chromatography (K145–160)

The step 2 product pool was evaporated to an oil using two 20-L rotovaps. To minimize foaming during the evaporation process, 10 L of ethanol were added to the mixture. The dried material was resuspended in 2.8 L of methanol and diluted with 3.4 L of water to make 6.2 L of a 45% methanol solution. The resulting solution was pumped onto a 1-L C18 chromatography column (55×4.8 cm) that had previously been equilibrated with 5 column volumes of 45% methanol. The loading flow rate averaged at 100 mL/min. The loaded column was washed with one liter of 60% methanol, and the epothilone D product was eluted from the resin using a step gradient at a flow rate of 100 mL/min. The column was eluted with 5 L of 55% methanol, 11.5 L of 60% methanol, and 13.5 L of 65% methanol. During the 55% methanol elution, a total of ten 500-mL fractions were collected. After switching to 60% methanol, a total of twenty-three 500-mL fractions were collected. During the final 65% methanol elution, eleven 500-mL fractions were collected, followed by eight 1-L fractions. The best epothilone D pool (K145–160-D), consisting of Fractions 28–50, contained 8.3 g of the desired product. Fractions 26–27 (K145–160-C) contained 0.4 g of the epothilone C and 0.2 g of epothilone D. All of these 25 fractions were combined.

To dilute product pool to 40% methanol in water, 9.5 L of water was added to 15.8 L of the loading solution. The resulting solution (25.3 L) was then pumped onto a 700-mL C18 chromatography column (9×10 cm) that had previously been equilibrated with 4 column volumes of 40% methanol. The loading flow rate averaged at 360 mL/min. The loaded column was washed with one liter of 40% methanol, and the epothilone D product was eluted from the resin with 3.75 L of 100% ethanol. The eluant was evaporated to dryness using a rotovap. The solids were resuspended in 100 mL of acetone, and the undissolved material was filtered from the solution using Whatman #2 filter paper. The filtered particles were washed with an additional 115 mL of acetone and filtered once more. Following the acetone extraction, 2 g of decolorizing charcoal were added to the combined filtrate. The mixture was stirred on a medium setting for 1 hour and was filtered using Whatman #50 filter paper. The charcoal was washed with 180 mL of ethanol and was filtered again. The filtrates were pooled together and rotovaped to dryness.

Step 4: Chromatography (K119–174)

The dried material from step 3 was resuspended in 5.0 L of 50% methanol in water and was loaded onto a 1-L C18 chromatography column (55×4.8 cm) that had previously been equilibrated with 3 column volumes of 50% methanol. The loading flow rate averaged 80 mL/min. The column was subsequently washed with one liter of 50% methanol, and the epothilone D product was eluted isocratically from the resin using 70% methanol at the same flow rate. A total of 48 fractions were collected, with the first 47 fractions containing 240 mL and the last fraction containing 1 L. Fractions 25–48 were taken as the best pool (K119–174-D), containing 7.4 g of epothilone D. Fractions 21–24 (K119–174-C) contained 1.1 g of epothilone D. Because this pool also contained high concentrations of epothilone C, it was set aside for re-work.

Step 5: Crystallization (K119–177)

To perform a solvent exchange prior to the crystallization step, 3.9 L of water was added to 6.4 L of the best epothilone D pool (K119–174-D) from step 5 to dilute the loading solution to 40% methanol in water. The resulting solution was then loaded onto a 200- mL C18 chromatography column (2.5×10 cm) that had previously been equilibrated with 3 column volumes of 40% methanol. The loaded column was washed with 200 mL of 40% methanol, and the epothilone D product was eluted from the resin with 1 L of 100% ethanol. The eluant was evaporated to dryness using a rotovap, and the solids were re-suspended with 150 mL of 100% ethanol. The clear solution was transferred to a beaker and with good stirring; 175 mL of water were slowly added. A small (1 mg) seed crystal of epothilone D was also added to the solution to promote crystal formation. However, seed crystals are not required for crystallization to occur. When the formation of small white crystals was observed, the solution was stirred for 15 more minutes until the solution became thick with white solids. The beaker was then removed from the stir plate, covered with aluminum foil, and placed in a refrigerator (2° C.) for 12 hours. The white solids were filtered using Whatman #50 filter paper, and no additional wash was performed on this first crop. The solids were placed in a crystallization dish and dried in a vacuum oven (40° C. at 15 mbar) for 6 hours. This crystallization process yielded 6.2 g of white solids, which contained >95% epothilone D. The recovery for this first crop was 74%.

Overview

The epothilone D recovery for run 1117001 K was 6.2 g of crystalline material at a purity of about 97.7%. Table 1 details the impurity profile for this fermentation. A novel epothilone compound was identified during the purification of epothilone D from strain K111-40-1 and was designated as "Epo490". This compound was subsequently identified as 10,11-dehydroepothilone D.

Impurity Profile for Purification Intermediates for 1117001K

| Step | Product | Epo C | Epo490 | Epo D |
|------|---------------|-------|--------|-------|
| 2 | SPE | 18 | 2 | 60 |
| 3 | C18 Chrom | 5.2 | 1.6 | 81.4 |
| 4 | C18 Chrom | 1.6 | 1.8 | 96.6 |
| 5 | Crystallization | 0.8 | 1.4 | 97.7 |

Epothilone D is stable at.room temperature in 80% methanol for at least one day. Based on HPLC analysis, degradation of the product under these conditions is not detectable. This finding allowed storage of the 170-L product pool from the XAD elution step in a 600-L stainless steel tank overnight without refrigeration. For optimal chromatography performance, the concentration of epothilone D in the loading solution should be kept below 2 g/L. At higher concentrations, the starting material has a tendency to oil out on the column. Crystallization was not achieved when feed material contained more than 3% of either epothilone C or epo490.

EXAMPLE 3

This example describes the isolation of 10,11-dehydroepothilone D from an enriched crystallization side stream (mother liquor) from the epothilone D production run 010501–1K and its subsequent structure determination.
Purification Early attempts at isolating 10,11-dehydroepothilone D focused solely on the use of C18 chromatography. The starting material was repeatedly chromatographed to remove the large amounts of epothilones C and D. This approach only gave partially purified material. Although C18 chromatography worked well at removing epothilones C and D, it was ineffective at separating 10,11-dehydroepothilone D from another co-eluting analog designated as Epo422 (which is also a novel compound of the present invention). A different approach was taken that took advantage of the observation that Epo422 was not detected in the crystallized epothilone D product although it was present in the production mother liquor. Briefly, the approach centers on the removal of Epo422 during the co-crystallization of 10,11-dehydroepothilone D with the more abundant epothilone D. Following crystallization, 10,11-dehydroepothilone D may then be separated from epothilone D using chromatography. Epothilone C is removed prior to the co-crystallization step. An HPLC chromatogram of the crystallized product showed it to contain 9% 10,11-dehydroepothilone D and 90% epothilone D. Three successive C18 chromatography columns gave 24 mg of material which contained approximately 85% 10,11-dehydroepothilone D.

A more detailed protocol is as follows. Rotary evaporation (Buchi rotovap, 30 mbar at 40° C.) of the mother liquor gave 3.0 g of solids. HPLC data showed 10,11-dehydroepothilone D present at 5% with respect to epothilones C and D. A 4.8×25 cm, 500 ml C18 (EM 40 um) chromatography column was washed with three column volumes (1500 ml) of 100% methanol (EM ACS grade) and equilibrated with five column volumes (2.5 L) of 50:50 methanol: water. The starting material was dissolved in 1 L of 100% methanol and to this solution was added 1 L of water. The mixture formed a turbid suspension that was pumped onto the C18 column using an FMI chromatography pump. The flow rate during loading was 240 cm hour (80 ml/minute). This generated a maximum pressure drop of 50 psi. An additional column volume (500 ml) of 50:50 methanol:water was pumped throughthe column to insure that the solvent lines and column headspace were clear of loading solution. Column elution was carried out in an isocratic fashion using 65:35 methanol:water. A total of 33 fractions containing 0.5 column volumes (250 ml) each were collected. Fractions 20–33 were combined and evaporated using a 2 L Buchi rotovap. The solids were dried in a vacuum oven at 40° C. and 20 mbar for 12 hours. The dried solids were dissolved in 500 ml of ethanol and to this solution was added 1 g of decolorizing charcoal. The mixture was stirred gently on a magnetic stirrer for 20 minutes and then vacuum filtered through Whatman #50 filter paper. The colorless filtrate was concentrated down to 100 ml on a rotary evaporator.

The concentrate was placed in a 250 ml media bottle containing a 0.5 inch magnetic spin bar. The bottle was fitted with a cap through which a hole had been drilled to accommodate a 1/8 inch feed tube, which was used for the slow delivery of the crystallization forcing solvent. The bottle in turn was placed in a 25° C. temperature controlled alcohol/water bath. With gentle mixing, 100 ml of water was added using a positive displacement pump at a flow rate of 2.5 mL/minute. At this point, 3 mg of epothilone D seed crystals were added to the already turbid mixture. After 5 minutes of vigorous stirring, the stirring speed was reduced, and many additional solids were observed. Water addition was resumed until a total of 150 ml of water had been added. The temperature of the solution was decreased to 0° C. over a thirty minute period and held there for an additional 12 hours with slow mixing. The crystals were filtered using Whatman #2 filter paper then redissolved in 2 L of 100% methanol.

To this solution was added 2 L of water, and the mixture was pumped onto a 4.8×25 cm C18 (EM 40 um) chromatography column that had been washed with 1.5 L of 100% methanol and equilibrated with 2.5 L of 50:50 methanol:water. An additional 500 mL of 50:50 methanol:water was pumped through the column following the column load. Elution was again carried out with 65:35 methanol:water. A total of 36 fractions each containing 250 ml were collected. All of the fractions containing 10,11-dehydroepothilone D were pooled (F20–F24) and rechromatographed on the same C18 column following a column wash with 1.5 L of 100% methanol and column equilibration with 50:50 methanol:water. Following the column load the column was eluted with 10 column (5 L) volumes of 65:35 methanol:water, which was collected as a single fraction. An additional 33 fractions were collected with each fraction containing 250 ml of eluant.

All of the 10,11-dehydroepothilone D containing fractions were pooled together and rechromatographed on a 2.5×30 cm C18 (Bakerbond 40 μm) column that had been equilibrated with 5 column volumes (130 mL) of 50:50 methanol:water. The loading solution was pumped onto the column at a flow rate of 20 mL/minute. This was followed by 130 mL of 50:50 methanol:water. The column was eluted with 1.8 L of 65:35 methanol:water followed by 1.8 L of 70:30 methanol:water. A total of 36 fractions each containing 100 ml of column eluant were collected. Fractions 29–31 were combined. Water was added (70 mL) to a concentration of 40:60 methanol:water. The turbid solution was loaded onto 20 ml of C18 contained in a 30 ml sintered glass funnel. The C18 resin was eluted with 100 ml of 100% ethanol, which was rotovaped to an oil then dried in a vacuum oven for 12 hours. This gave 24 mg of a colorless oil which when analyzed by HPLC gave a chromatographic purity (relative % area) of 94%

Structure Determination

The molecular formula of $C_{27}H_{39}O_5NS$ for Epo490, established from HRESIMS and $^{13}C$ NMR data, differed from epothilone D by an additional double bond equivalent. The $^1H$ and $^{13}C$ NMR data revealed that Epo490 did possess an additional carbon-carbon double bond, which was determined to be of E-configuration based on a coupling constant of $^3J_{H-H}$ of 16.0 Hz for two protons resonating at δ6.52 and 5.76. The $^1H$ NMR spectrum displayed five methyl singlets (δ2.69, 2.09, 1.79, 1.29, 1.03) and two methyl doublets (δ1.11, J=7.0; 1.03, J=7.0 Hz), analagous to that of epothilone D. Multiplicity-edited HSQC data was used to determine $^1J_{C-H}$ connectivities and indicated that three methylene groups were present. TOCSY, COSY-60, and HMBC data established the spin system $H_3$-27, H-13, $H_2$-14, H-15. HMBC correlations from $H_3$-26 to three olefinic carbon signals at δ129.1 (C-11), 135.7 (C-12), and 123.1 (C-13), as well as from δ5.76 (H-10) to C-12 and δ6.52 (H-11) to C-12 and C-13 placed the additional double bond at the 10-11 position. Additional 2D NMR was entirely consistent with C-1 through C-9 being the same as found in epothilone D. The configuration of the 12,13 double bond was determined to be Z based on calculations and comparison of the carbon shift for C-26 of epothilone D.

H NMR (400 MHz) and $^3C$ NMR (100 MHz) were recorded in $CDCl_3$ solution at 300 K with a Bruker DRX 400 spectrometer equipped with a QNP z-axis gradient probehead. Chemical shifts were referred to δ7.26 and 77.0 for $^1H$ and $^{13}C$ spectra, respectively. HRMS spectra were obtained by FIA with manual peak-matching on an Applied Biosystems Mariner TOF spectrometer with a turbo-ionspray source in positive ion mode (spray tip potential, 5400 V; spray chamber temp., 400° C.; nozzle potential, 110 V). Resolution of measured mass was 6600.

Epo490: HRESIMS m/z 490.2632; calcd for $C_{27}H_{40}NO_5S$ [M+H]$^+$, 490.2622. $^1H$ NMR ($CDCl_3$, 400 MHz) δ6.96 (1H, s, H-19), 6.57 (1H, s, H-17), 6.52 (1H, d, J=16.0 Hz, H-11), 5.76 (1H, ddd, J=16.0, 9.0, 5.5 Hz, H-10), 5.29 (1H, ovrlp, H-15), 5.28 (1H, ovrlp, H-13), 4.21 (1H, dd, J=10.0 Hz, 3.5, H-3), 3.71 (1H, dd, J=6.5 Hz, 2.0, H-7), 3.25 (1H, qd, J=7.0, 2.0 Hz, H-6), 2.81 (1H, dt, J=14.0, 10.5 Hz, H-14$_a$), 2.69 (3H, s, C-21), 2.52 (1H, dt, J=14.5, 5.5 Hz, H-9$_a$), 2.42 (1H, dd, J=14.5, 10.0 Hz, H-2$_a$), 2.35 (1H, dd, J=14.5, 3.5 Hz, H-2$_b$), 2.28 (1H, dd, J=14.0, 6.0 Hz, H-14$_b$), 2.09 (3H, s, H-27), 2.07 (1H, m, H-9$_b$), 1.98 (1H, m, H-8), 1.79 (3H, s, H-26), 1.29 (3H, s, H-22), 1.11 (3H, d, J=7.0 Hz, H-24), 1.06 (3H, d, J=7.0 Hz, H-25), 1.03 (3H, s, H-23). $^{13}C$ NMR ($CDCl_3$, 100 MHz) δ220.2 (C-5), 170.2 (C-1), 164.9 (C-20), 152.1 (C-18), 138.1 (C-16), 135.7 (C-12), 129.5 (C-10), 129.1 (C-11), 123.1 (C-13), 119.5 (C-17), 116.1 (C-19), 78.4 (C-15), 71.9 (C-3), 71.6 (C-7), 53.3 (C-4), 41.2 (C-6), 39.4 (C-2), 36.9 (C-8), 36.0 (C-9), 32.1 (C-14), 21.14 (C-22), 21.05 (C-26), 19.2 (C-23), 19.1 (C-21), 16.8 (C-25), 15.6 (C-27), 11.5 (C-24).

EXAMPLE 4

This example describes the protocol for purifying 10,11-dehydroepothilone D starting from the fermentation of strain K111-40-1.

Step 1: XAD Elution

XAD resin is filtered from the fermentation culture using a Mainstream filtration unit with a thirteen-liter 150 um capture basket. The captured XAD resin is packed into an Amicon VA250 column and washed with 65 L (3.8 column volumes) of water at 1.0 L/min. The epothilone products are eluted from the resin using 230 L of 80% methanol in water.

Step 2: Solid Phase Extraction

Seventy-seven liters (77 L) of water are added to the step 1 product pool (230 L) to dilute the loading solvent to 60% methanol in water. The resulting suspension (307 L) is hand-mixed and loaded onto an Amicon VA180 column packed with 5 L of HP20SS resin that has previously been equilibrated with 5 column volumes of 60% methanol. The loading flow rate is 1 L/min. After loading, the column is washed with 13 L of 60% methanol and eluted with 77L of 75% methanol at a flow rate of 325 mL/min. Fractions are collected and those fractions containing epothilone C, epothilone D, and 10,11-dehydroepothilone D (as determined by UV detection) are pooled together.

Step 3: Chromatography

The step 2 product pool is evaporated to an oil using two 20-L rotovaps. During evaporation, it is often necessary to add ethanol to minimize foaming. The dried material is re-suspended in 1.0 L of methanol and diluted with 0.67 L of water to make 1.67 L of a 60% methanol solution. The resulting solution is pumped onto a 1 L C-18 chromatography column (55×4.8cm) that has previously been equilibrated with 3 column volumes of 60% methanol. The loading flow rate averages at approximately 64 mL/min. The loaded column is washed with one liter of 60% methanol, and the epothilone products are eluted out isocratically using 70% methanol at a flow rate of 33 mL/min. Fractions are collected and those containing epothilone C, epothilone D, and 10,11-dehydroepothilone D are pooled together.

Step 4: Chromatography

The fractions are rotovaped (Buchi rotovap, 30 mbar at 40° C.) to give dried solutions containing the epothilones. HPLC analysis was carried out on a Hitachi L6200 series chromatograph fitted with an L-6100 gradient pump, an A-2000 auto sampler, and an L-4500 diode array detector. Detection was carried out at 250 nm. A Metachem Inertsil ODS-3 5 um column was used for analyzing both product pools and individual fractions.

A 4.8×25 cm, 500 ml C18 (EM 40 um) chromatography column is washed with three column volumes (1500 ml) of 100% methanol (EM ACS grade) and equilibrated with five column volumes (2.5 L) of 50:50 methanol:water. The dried solids are dissolved in 1 L of 100% methanol. 1 L of water is added to this solution forming a turbid suspension that is pumped onto the C18 column using an FMI chromatography pump. The flow rate during loading is 240 cm hour (80 ml/minute). This generates a maximum pressure drop of 50 psi. An additional column volume (500 ml) of 50:50 methanol:water is pumped through the column in order to insure that the solvent lines and column headspace are clear of loading solution. Column elution is carried out in an isocratic fashion using 65:35 methanol:water. Fractions are collected and those containing epothilone D and 10,11-dehydroepothilone D are pooled together, combined and evaporated using a 2 L Buchi rotovap. This chromatography step substantially removes epothilone C from epothilone D and 10,11-dehydroepothilone D. Subsequent crystallization of epothilone D and 10,11-dehydroepothilone D is problematic if the levels of epothilone C is greater than 3%.

Step 5: Filtration

The solids from step 4 are dried in a vacuum oven at 40° C. and 20 mbar for 12 hours and then dissolved in 500 mL of ethanol. 1 g of decolorizing charcoal is added to the solution. The mixture is stirred gently on a magnetic stirrer for 20 minutes then vacuum filtered through Whatman #50 filter paper. The colorless filtrate is concentrated down to 100 ml on a rotary evaporator.

Step 6: Crystallization

The concentrate from step 5 is placed into a 250 ml media bottle containing a 0.5 inch magnetic spin bar. The bottle is fitted with a cap through which a hole had been drilled in order to accommodate 1/8 inch feed tube, which is used for the slow delivery of the crystallization forcing solvent. The bottle in turn is placed in a 25° C. temperature controlled alcohol/water bath. With gentle mixing 100 mL of water is added using a positive displacement pump at a flow rate of 2.5 mL/minute. At this point, the solution may be optionally seeded, preferably with crystal of any epothilone compound, more preferably about 3 mg of epothilone D or epothilone D/10,11-dehydroepothilone D co-crystals as seed crystals. If epothilone crystals are not available, any material (i.e., other crystals) or method that initiates or promotes crystallization may be used. After 5 minutes of vigorous stirring, the stirring speed is reduced and many additional solids are observed. Water addition is resumed until a total of 150 mL of water has been added. The temperature of the solution is decreased to 0° C. over a thirty minute period and held there for an additional 12 hours with slow mixing. The crystals are filtered using Whatman #2 filter paper then redisolved in 2 L of 100% methanol. The crystals contain epothilone D and 10,11-dehydroepothilone D.

Step 7: Chromatography 2 L of water are added to the solution resulting from step 6 and the mixture is pumped onto a 4.8×25 cm C18 (EM 40 um) chromatography column that has been washed with 1.5 L of 100% methanol and equilibrated with 2.5 L of 50:50 methanol:water. An additional 500 mL of 50:50 methanol:water are pumped through the column following the column load. Elution is again carried out with 65:35 methanol:water. A total of 36 fractions each containing 250 mL are collected. All of the fractions containing 10,11-dehydroepothilone D are pooled (F20–F24). The chromatography step may be repeated as necessary to obtain the desired purity of 10,11-dehydroepothilone D. The major contaminant is epothilone D. Optionally, the crystallization step may also be repeated.

The final chromagraphy steps separate 10,11-dehydroepothilone D from epothilone D. The chromatography step is typically repeated twice where the pooled fractions are rechromatographed on the same C18 column following a column wash with 1.5 L of 100% methanol and column equilibration with 50:50 methanol:water. Following the column load, the column is eluted with 10 column (5 L) volumes of 65:35 methanol:water, which is collected as a single fraction. An additional 33 fractions are collected with each fraction containing 250 mL of eluant. All of the 10,11-dehydroepothilone D containing fractions are pooled together and rechromatographed on a 2.5×30 cm C18 (Bakerbond 40 μm) column that has been equilibrated with 5 column volumes (130 ml) of 50:50 methanol:water. The loading solution is pumped onto the column at a flow rate of 20 mL/minute. This is followed by 130 mL of 50:50 methanol:water. The column is eluted with 1.8 L of 65:35 methanol:water followed by 1.8 L of 70:30 methanol:water. A total of 36 fractions each containing 100 mL of column eluant are collected. Fractions 29–31 are combined. Water is added (70 mL) to a concentration of 40:60 methanol:water. The turbid solution is loaded onto 20 mL of C18 contained in a 30 ml sintered glass funnel. The C18 resin is eluted with 100 mL of 100% ethanol, which was rotovaped to an oil and dried in a vacuum oven for 12 hours. 10,11-dehydroepothilone D is obtained as a colorless oil.

EXAMPLE 5

This example describes the biological assays that were performed to determine the activity of 10,11-dehydroepothilone D.

10,11-dehydroepothilone D was screened for anticancer activity in four different human tumor cell lines using sulforhodamine B (SRB) assay. 10,11-dehydroepothilone D shows growth inhibitory effect on all four cell lines with $IC_{50}$s ranging from 28 nM to 40 nM. The mechanism of action was determined by a cell-based tubulin polymerization assay which revealed that the compound promotes tubulin polymerization. Human cancer cell lines MCF-7 (breast), NCI/ADR-Res (breast, MDR), SF-268 (glioma), NCI-H460 (lung) were obtained from National Cancer Institute. The cells were maintained in a 5% CO2-humidified atmosphere at 37 degree in RPMI 1640 medium (Life Technology) supplemented with 10% fetal bovine serum (Hyclone) and 2mM L-glutamine.

Cytotoxicity of 10,11-dehydroepothilone D was determined by SRB assay (Skehan et al., *J. Natl. Cancer Inst.* 82: 1107–1112 (1990) which is incorporated herein by reference). Cultured cells were trypsinized, counted and diluted to the following concentrations per 100 ul with growth medium: MCF-7, 5000; NCI/ADR-Res, 7500; NCI-H460, 5000; and, SF-268, 7500. The cells were seeded at 100 ul/well in 96-well microtiter plates. Twenty hours later, 100 ul of 10,11-dehydroepothilone D (ranging from 1000 nM to 0.001 nM diluted in growth medium) were added to each well. After incubation with the compound for 3 days, the cells were fixed with 100 ul of 10% trichloric acid ("TCA") at 4 degree for 1 hour, and stained with 0.2% SRB/1% acetic acid at room temperature for 20 minutes. The unbound dye was rinsed away with 1% acetic acid, and the bound SRB was then extracted by 200 ul of 10 mM Tris base. The amount of bound dye was determined by OD 515 nm, which correlates with the total cellular protein contents. The data were then analyzed using Kaleida Graph program and the $IC_{50}$'s calculated. Epothione D that was chemically synthesized was tested in parallel for comparison.

For tubulin polymerization assay, MCF-7 cells were grown to confluency in 35 mm-culture dishes and treated with 1 uM of either 10,11-dehydroepothilone D or epothilone D for 0, 1 or 2 hours at 37 degree (Giannakakou et al., *J. Biol. Chem.* 271:17118–17125 (1997); *Int. J. Cancer* 75: 57–63 (1998) which are incorporated herein by reference). After washing the cells twice with 2 ml of PBS without calcium or magnesium, the cells were lysed at room temperature for 5–10 minutes with 300 ul of lysis buffer (20 mM Tris, PH 6.8, 1 mM $MgCl_2$, 2 mM EGTA, 1% Triton X-100, plus protease inhibitors). The cells were scraped and the lysates transferred to 1.5-ml Eppendof tubes. The lysates were then centrifuged at 18000 g for 12 minutes at room temperature. The supernatant containing soluble or unpolymerized (cytosolic) tubulin were separated from pellets containing insoluble or polymerized (cytoskeletal) tubulin and transferred to new tubes. The pellets were then resuspended in 300 ul of lysis buffer. Changes in tubulin polymerization in the cell were determined by analyzing same volume of aliquots of each sample with SDS-PAGE, followed by immunoblotting using an anti-tubulin antibody (Sigma).

The results of several experiments showed that 10,11-dehydroepothilone D has an $IC_{50}$ in the range of 28 nM to 40 nM against four different human tumor cells lines.

TABLE 1

| Cell lines | EpoD (nM) N = 3 | Epo490 (nM) N = 2 |
|---|---|---|
| MCF-7 | 21 ± 10 | 28 ± 8 |
| NCI/ADR | 40 ± 12 | 35 ± 9 |

| Cell lines | EpoD (nM) N = 3 | Epo490 (nM) N = 2 |
|---|---|---|
| SF-268 | 34 ± 8 | 40 ± 5 |
| NCI-H460 | 30 ± 2 | 34 ± 1 |

Tubulin polymerization assays reveal that 10,11-dehydroepothilone D has the same mechanism of action as epothilone D. In MCF-7 cells, 10,11-dehydroepothilone D strongly promoted tubulin polymerization at the conditions tested, with similar kinetics and effect as epothilone D.

EXAMPLE 6

This example describes the construction of a Myxococcus strain that produces 10,11-dehydroepothilone D. A strain that produces 10,11-dehydroepothilone D was constructed by inactivating the enoyl reductase (ER) domain of extender module 5. The ER inactivation was accomplished by changing the two glycines (-Gly-Gly-) in the NADPH binding region to an alanine and serine (-Ala-Ser-). The 2.5 kb BbvCl-HindIII fragment from plasmid pKOS39–118B (a subclone of the epoD gene from cosmid pKOS35–70.4) was cloned into pLitmus28 as pTL7, which was used as a template for site directed mutagenesis. The oligonucleotide primers for introducing the -Gly-Gly- to -Ala-Ser- mutations into the NADPH binding domain were:

TLII-22,5'-TGATCCATGCTGCGGC-CGCTAGCGTGGGCATGGCCGC; and

TLII-23,5'-GCGGCCATGCCCACGCTAGCGGCCGCAG-CATGGATCA.

The PCR clones containing the substitutions were confirmed by sequencing and were digested with the restriction enzyme DraI and treated with shrimp alkaline phosphatase. Then, the large fragment of each clone was ligated with the kanamycin resistance and galK gene (KG or kan-gal) cassette to provide the delivery plasmids. The delivery plasmids were transformed into the epothilone D producer M. xanthus K111-72-4.4 and K111-40-1 by electroporation. The transformants were screened and kanamycin-sensitive, galactose-resistant survivors were selected to identify clones from which the KG genes had been eliminated. Confirmation of the KG elimination and the desired gene replacement for the recombinant strains was performed by PCR. The recombinant strains were fermented in flasks with 50 mL of CTS medium (casitone, 5 g/L; $MgSO_4 \cdot 7H_2O$, 2 g/L; and HEPES buffer, 50 mM pH 7.6) and 2% XAD-16 for 7 days, and the XAD resin was collected and washed with water. The crude 10,11-dehydroepothilone D was eluted from the XAD resin with 10 mL of methanol.

EXAMPLE 7

This example describes the synthesis of (5S)-2-iodo-6-methyl-7-(2-methylthiazol-4-yl)-5-(triethylsilyloxy)-2,6-heptadiene (fragment A) whose structure is shown below

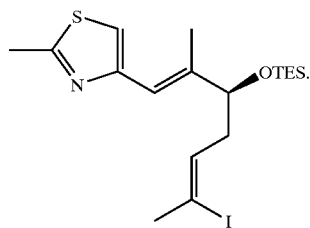

Fragment A is a common intermediate in the Heck coupling and the Suzuki coupling routes to 10,11-dehydroepothilone D. The synthesis of Fragment B1, the Heck coupling partner, is described in Example 8 and the synthesis of Fragment B2, the Suzuki coupling partner, is described in Example 9. The synthesis of 10,11-dehydroepothilone D is described in Example 10.

(a) (4R)-4-hydroxy-3,5-dimethyl-6-(2-methylthiazol-4-yl))-1,5-hexadiene

A solution of 2-methyl-3-(2-methylthiazol-4-yl))propenal (4.3 g) in 50 mL of anhydrous ether is cooled to −100° C. A pentane solution of (−)-diisopinocampheylallylborane (1.5 equiv) is added dropwise to the vigorously stirred aldehyde solution. After the addition is complete, the reaction mixture is stirred for 1.5 hours and warmed to −50° C. A solution of 30% aq $H_2O_2$ (20 mL) and 10% aq $NaHCO_3$ (50 mL) is added, and the resulting turbid mixture is stirred at 25° C. for 8 hours. The organic layer is separated, and the aqueous layer is extracted with ether. The combined organic layers are washed with satd aq $Na_2S_2O_3$ and brine, dried ($MgSO_4$), filtered, and concentrated. Purification by flash column chromatography on $SiO_2$ (hexanes/ethyl acetate, 10:1) affords the alcohol as a clear oil.

(b) (4R)-4-(triethylsilyloxy)-5-methyl-6-(2-methylthiazol-4-yl))-1,5-hexadiene

Triethylsilyl trifluromethanesulfonate (15 mL) is added dropwise to a −78° C. solution of (4R)-4-hydroxy-5-methyl-6-(2-methylthiazol-4-yl))-1,5-hexadiene (4.3 g) and 2,6-lutidine (10 mL) in 50 mL of $CH_2Cl_2$. After the addition, the reaction mixture is allowed to warm to ambient temperature and is stirred for 5 hours. The reaction mixture is poured into 2 N HCl and extracted with ether. The combined organic layers were washed with 10% aq $NaHCO_3$ and brine, dried ($Na_2SO_4$), filtered, and concentrated. Flash chromatography on $SiO_2$ (hexanes/ethyl acetate, 20:1) provids the product as a colorless oil.

(c) (3R)-3-(triethylsilyloxy)-4-methyl-5-(2-methylthiazol-4-yl)-pent-4-enal

Osmium tetraoxide (1 wt % in THF, 20.3 mL) is added to a mixture of (4R)-4-(triethylsilyloxy)-5-methyl-6-(2-methylthiazol-4-yl)-1,5-hexadiene (13.5 g), $H_2O$ (21 mL), and N-methylmorpholine N-oxide (50% in THF, 10 mL, 0.048 mol) in tert-butanol (155 mL) at 0° C. After the resulting mixture is stirred for 12 hours, $Na_2SO_3$ (10 g) and water (5 mL) are added. The resulting solution is stirred at 25° C. for 30 minutes and then extracted with ether. The combined extracts are washed with brine, dried ($Na_2SO_4$), filtered, and concentrated. Purification by flash chromatography on $SiO_2$ provides a 1:1 diastereomeric mixture of the diol as a colorless, viscous oil. Lead tetraacetate (19.1 g) is added portionwise over 5 minutes to a suspension of the diol (18.0 g) and $Na_2CO_3$ (8.67 g) in 500 mL of benzene at 0° C. After stirring for 15 minutes, the mixture is filtered through a $SiO_2$ pad to afford the aldehyde product. The product is directly subjected to the next reaction.

(d) (5R)-2-iodo-6-methyl-7-(2-methylthiazol-4-yl)-5-(triethylsilyloxy)-2,6-heptadiene To a suspension of ethyltriphenylphosphonium iodide (7.90 g) in THF (150 mL) is added n-butyllithium (7.17 mL, 2.5 M in hexane) at ambient temperature. After disappearance of the solid material, the red solution is cannulated into a vigorously stirred solution of iodine (4.54 g) in THF (150 mL) at −78° C. The resulting dark brown suspension is stirred for 5 minutes and allowed to warm gradually to −30° C. A solution of sodium hexamethyldisilazide (17.3 mL, 1.0 M in THF) is added dropwise to afford a dark red solution. A solution of (3R)-3-(triethylsilyloxy)-4-methyl-5-(2-methylthiazol-4-yl)-pent-4-enal (2.0 g) in THF (10 mL) is slowly added, and stirring is continued at −30° C. for 30 minutes. The reaction mixture is diluted with pentane (100 mL), filtered through a pad of Celite, and concentrated. Purification by flash column chromatography on SiO₂ (hexane/ethyl acetate, 15:1) affords the vinyl iodide.

EXAMPLE 8

This example describes the synthesis of tert-butyl (3S,6R,7S,8S)-5-oxo-3-(triethylsilyloxy)-4,4,6,8-tetramethyl-7-(2,2,2-trichloroethoxycarbonyloxy)-10-undecenoate (Fragment B1) whose structure is shown below

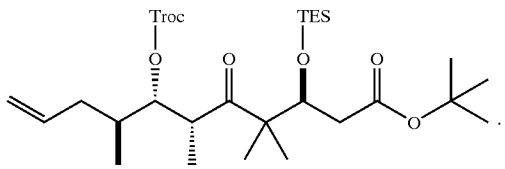

Fragment B1 is the Heck coupling partner to Fragment A whose synthesis was described in Example 7. Fragments A and B1 are joined together in a Heck coupling reaction which is described in Example 10 to make 10,11-dehydroepothilone D.

(a) (4R,5S,6S)-1,1-diisopropoxy-5-hydroxy-2,2,4,6-tetramethyl-8-nonen-3-one

A solution of 1,1-diisopropoxy-2,2,-dimethyl-3-pentanone (3.29 g) in 15 mL of THF is added slowly to a solution of lithium diisopropylamide (15.7 mmol) in 20 mL of THF cooled to −78° C., the mixture is stirred for 30 minutes, warmed to −40° C. and stirred for 30 minutes, then recooled to −78° C. A solution of (2S)-2-methyl-4-pentenal (16.36 mmol) in 2 mL of CH₂Cl₂ is added and the mixture is stirred for 1 hour at −78° C. Saturated aq. NH4Cl is added and the mixture is warmed to ambient temperature and extracted with ethyl acetate. The extract is dried over Na₂SO₄, filtered, and evaporated. The residue is purified by silica gel chromatography (2% ethyl acetate/hexanes) to separate the two diastereomeric products.

(b) (4R,5S,6S)-1,1-diisopropoxy-5-(2,2,2-trichloroethoxycarbonyloxy)-2,2,4,6-tetramethyl-8-nonen-3-one Trichloroethyl chloroformate (2.5 mL) and pyridine (2.95 mL) are added to a solution of (4R,5S,6S)-1,1-diisopropoxy-5-hydroxy-2,2,4,6-tetramethyl-8-nonen-3-one (3.0 g) in 40 mL of CH₂Cl₂ at 0° C., and the mixture is stirred for 5 hours before pouring into sat. aq. NaCl and extracting with CH₂Cl₂. The extract is dried over Na₂SO₄, filtered, and evaporated. The product is purified by chromatography on SiO₂ (2% ethyl acetate/hexanes).

(c) (4R,5S,6S)-3-oxo-5-(2,2,2-trichloroethoxycarbonyloxy)-2,2,4,6-tetramethyl-8-nonenal A mixture of (4R,5S,6S)-1,1-diisopropoxy-5-(2,2,2-trichloroethoxycarbonyloxy)-2,2,4,6-tetramethyl-8-nonen-3-one (4.58 g) and p-toluenesulfonic acid monohydrate (0.45 g) in 100 mL of 3:1 THF/water is heated at reflux for 7 hours. The mixture is cooled and poured into sat. aq. NaHCO₃, then extracted with ethyl acetate. The extract is dried over Na₂SO₄, filtered, and evaporated. The product is purified by chromatography on SiO₂ (3% ethyl acetate/hexanes).

(d) tert-butyl (3S,6R,7S,8S)-5-oxo-3-hydroxy-4,4,6,8-tetramethyl-7-(2,2,2-trichloroethoxycarbonyloxy)-10-undecenoate Tert-butyl acetate (0.865 mL) is added to a solution of lithium diisopropylamide (7.52 mmol) in 30 mL of ether at −78° C., and the mixture is stirred for 1 hour. A solution of bis(1,2:5,6-di-O-isopropylidene-α-L-glucofuranos-3-O-yl) cyclopentadienyltitanium chloride (8.34 mmol) in 90 mL of ether is added dropwise over 40 minutes, and the reaction is stirred for an additional 30 minutes at −78° C., warmed to −30° C. and kept for 45 minutes, then recooled to −78° C. A solution of (4R,5S,6S)-3-oxo-5-(2,2,2-trichloroethoxycarbonyloxy)-2,2,4,6-tetramethyl-8-nonenal (2.57 g) in 15 mL of ether is added over 10 minutes and the reaction is continued for 2 hours before addition of 14 mL of 5 M water in THF. The mix is stirred for 1 hour then filtered through Celite. The filtrate is washed with sat. aq. NaCl, and the brine layer is back extracted with ether. The organic phases are combined, dried with Na₂SO₄, filtered, and evaporated. The product is purified by chromatography on SiO₂ (7% ethyl acetate/hexanes).

(e) Tert-butyl (3S,6R,7S,8S)-5-oxo-3-(triethylsilyloxy)-4,4,6,8-tetramethyl-7-(2,2,2-trichloroethoxycarbonyloxy)-10-undecenoate A solution of tert-butyl (3S,6R,7S,8S)-5-oxo-3-hydroxy-4,4,6,8-tetramethyl-7-(2,2,2-trichloroethoxycarbonyloxy)-10-undecenoate (1.8 g), imidazole (0.48 g), and triethylsilyl chloride (0.68 g) in 5 mL of dimethylformamide is stirred for 2 hours at ambient temperature, then poured into water and extracted with ether. The extract is washed with sat. aq. NaCl, dried over MgSO₄, filtered, and evaporated. The product is purified by chromatography on SiO₂ (20:1 toluene/ethyl acetate).

EXAMPLE 9

This example describes the synthesis of tert-butyl (3S,6R,7S,8S)-5-oxo-3-(triethylsilyloxy)-4,4,6,8-tetramethyl-7-(2,2,2-trichloroethoxycarbonyloxy)-10-undecynoate (Fragment B2) whose structure is shown below

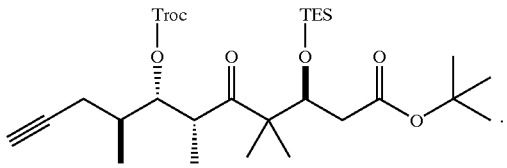

Fragment B2 is the Suzuki coupling partner to Fragment A whose synthesis was described in Example 7. Fragments A and B2 are joined together in a Suzuki coupling reaction which is described in Example 10 to make 10,11-dehydroepothilone D. Fragment B2 is prepared according to the method of Example 8, substituting (2S)-2-methyl-4-propynal for (2S)-2-methyl-4-propenal.

EXAMPLE 10

This example describes the synthesis of 10,11-dehydroepothilone D from the Heck coupling of Fragments A and B1 or from the Suzuki coupling of Fragments A and B2. The product of both couping reactions is tert-butyl (3S,6R,7S,8S,10E,12Z,15S,16E)-5-oxo-3,15-bis (triethylsilyloxy)-17-(2-methylthiazol-4-yl)-4,4,6,8,12,16-hexamethyl-7-(2,2,2-trichloroethoxycarbonyloxy)-heptadeca-10,12,16-trienoate which is made in subpart (a) of this example where method A is the Heck coupling route and method B is the Suzuki coupling route.

(a) tert-butyl (3S,6R,7S,8S,10E,12Z,15S,16E)-5-oxo-3,15-bis(triethylsilyloxy)-17-(2-methylthiazol-4-yl)-4,4,6,8,12,16-hexamethyl-7-(2,2,2-trichloroethoxycarbonyloxy)-heptadeca-10,12,16-trienoate Method A: A solution of tert-butyl (3S,6R,7S,8S)-5-oxo-3-(triethylsilyloxy)-4,4,6,8-tetramethyl-7-(2,2,2-trichloroethoxycarbonyloxy)-10-undecenoate (2.12 g) in 4 mL of THF is added to a vigorously stirred mixture of (5S)-2-iodo-6-methyl-7-(2-methylthiazol-4-yl)-5-(triethylsilyloxy)-2,6-heptadiene (1.4 g), cesium carbonate (1.49 g), triphenylarsine (0.188 g), and (dppf)PdCl2·CH$_2$Cl$_2$ (0.25 g) in 2 mL of degassed dimethylformamide cooled to 0° C. The reaction is stirred for 15 hours, then poured into 10% NaHSO$_4$ and extracted with ethyl acetate. The organic phase is separated, washed sequentially with 10% NaHCO$_3$ and brine, dried over MgSO$_4$, filtered, and evaporated. The product is purified by flash chromatography on SiO$_2$ (10:1 hexanes/ethyl acetate).

Method B: A solution of tert-butyl (3S,6R,7S,8S)-5-oxo-3-(triethylsilyloxy)-4,4,6,8-tetramethyl-7-(2,2,2-trichloroethoxycarbonyloxy)-10-undecynoate (2.1 g) in 4 mL of THF is added to a 1.0 M solution of catecholborane in THF (3.3 mL), the mixture is stirred for 2 hour at 60° C. The resulting solution is added to a vigorously stirred mixture of (5S)-2-iodo-6-methyl-7-(2-(2,2,2-trichloroethoxycarbonyl-oxymethyl)thiazol-4-yl)-5-(triethylsilyloxy)-2,6-heptadiene (2.0 g), cesium carbonate (1.49 g), triphenylarsine (0.188 g), and (dppf)PdCl2·CH$_2$Cl$_2$ (0.25 g) in 2 mL of degassed dimethylformamide cooled to 0° C. The reaction is stirred for 15 hours, then poured into 10% NaHSO$_4$ and extracted with ethyl acetate. The organic phase is separated, washed sequentially with 10% NaHCO$_3$ and brine, dried over MgSO$_4$, filtered, and evaporated. The product is purified by flash chromatography on SiO2 (10:1 hexanes/ethyl acetate).

(b)(3S,6R,7S,8S,10E,12Z,15S,16E)-5-oxo-3-(triethylsilyloxy)-15-hydroxy-17-(2-methylthiazol-4-yl)-4,4,6,8,12,16-hexamethyl-7-(2,2,2-trichloroethoxycarbonyloxy)-heptadeca-10,12,16-trienoic acid A solution of tert-butyl (3S,6R,7S,8,10E,12Z,15S,16E)-5-oxo-3,15-bis(triethylsilyloxy)-17-(2-methylthiazol-4-yl)-4,4,6,8,12,16-hexamethyl-7-(2,2,2-trichloroethoxycarbonyloxy)-heptadeca-10,12,16-trienoate (2.38 g) in 12 mL of CH$_2$Cl$_2$ is treated with 2,6-lutidine (0.86 mL) and triethylsilyl trifluoromethanesulfonate (0.98 g) at 0° C. for 30 minutes, then at ambient temperature for 10 hours. The mixture is diluted with 50 mL of ethyl acetate and poured into 20 mL of 1 N HCl. The organic phase is separated, washed with pH 7 phosphate buffer, dried with Na$_2$SO$_4$, filtered, and concentrated. The residue is dissolved in 5 mL of THF and treated with 0.5 mL of 0.1 N HCl in methanol. The reaction is monitored by thin-layer chromatography, with additional aliquots of methanolic HCl being added to achieve complete reaction. When complete, the reaction is poured into 15 mL of pH 7 phosphate buffer and extracted with ethyl acetate. The extract is washed with brine, dried with Na$_2$SO$_4$, filtered, and evaporated. The product is purified by flash chromatography on SiO$_2$ (1:1 hexanes/ethyl acetate).

(c) 7-O-(2,2,2-trichloroethoxycarbonyl)-3-O-(triethylsilyl)-10,11-dehydroepothilone D A solution of (3S,6R,7S,8S,10E,12Z,15S,16E)-5-oxo-3-(triethylsilyloxy)-15-hydroxy-17-(2-methylthiazol-4-yl)-4,4,6,8,12,16-hexamethyl-7-(2,2,2-trichloroethoxycarbonyloxy)-heptadeca-10,12,16-trienoic acid (0.4 g) in 9 mL of THF is treated with triethylamine (0.36 mL) and 2,4,6-trichlorobenzoyl chloride (0.528 g). After 15 minutes, 40 mL of toluene is added, and the resulting solution is added via syringe pump over 3 hours to a solution of 4-dimethylaminopyridine (0.525 g) in 400 mL of toluene. After an additional 1 hour, the mixture is filtered through Celite and concentrated. The product is purified by flash chromatography on SiO$_2$ (2:1 hexanes/ethyl acetate).

(d) 3-O-(triethylsilyl)-10,11-dehydroepothilone D

A solution of 7-O-(2,2,2-trichloroethoxycarbonyl)-3-O-(triethylsilyl)-10,11-dehydroepothilone D (0.18 g) in 1 mL of THF is added to a stirred suspension of activated zinc dust (0.261 g) in 2 mL of acetic acid. After stirring for 1.5 hours, the mixture is diluted with ethyl acetate and filtered. The filtrate is washed sequentially with 10% NaHCO$_3$ and brine, dried over MgSO$_4$, filtered, and evaporated. The product is purified by flash chromatography on SiO$_2$ (2:1 hexanes/ethyl acetate).

(e) 10,11-dehydroepothilone D

A solution of 3-O-(triethylsilyl)-10,11-dehydroepothilone D (80 mg) in 2 mL of THF in a polyethylene vessel and treated with 1.5 mL of HF·pyridine for 1 hour at 0° C. and 30 minutes at ambient temperature, then diluted with 30 mL of ethyl acetate and poured into 20 mL of sat. aq. NaHCO$_3$. The organic phase is separated and washed sequentially with 1 N HCl, 10% NaHCO$_3$, and brine, then dried over MgSO$_4$, filtered, and evaporated. The product is purified by flash chromatography on SiO$_2$ (1:2 hexanes/ethyl acetate).

EXAMPLE 11

This example describes the microbial transformation of C-20 methyl to C-20 hydroxymethyl of 10,11-dehydroepothilone D regardless of whether it was obtained from fermentation as described by Example 2 or 6, or from chemical synthesis as described by Examples 7–10. A frozen vial (approximately 2 ml) of *Amycolata autotrophica* ATCC 35203 or Actinomyces sp. strain PTA-XXX as described by PCT Publication No. WO 00/39276 is used to inoculate 1 500 ml flask containing 100 mL of medium. The vegetative medium consists of 10 g of dextrose, 10 g of malt extract, 10 g of yeast extract, and 1 g of peptone in liter of deionized water. The vegetative culture is incubated for three days at 28° C. on a rotary shaker operating at 250 rpm. One mL of the resulting culture is added to each of sixty-two 500 mL flasks containing the transformation medium which as the same composition as the vegetative medium. The cultures are incubated at 28° C. and 250 rpm for 24 hours. 10,11-dehydroepothilone D is dissolved in 155 ml of ethanol and the solution is distributed to the sixty-two flasks. The flasks are then returned to the shaker and incubated for an additional 43 hours at 28° C. and 250 rpm. The reaction culture is then processed to recover 21-hydroxy-10,11-dehydroepothilone D (which also may be referred to as 10,11-dehydro-12,13-desoxy epothilone F).

EXAMPLE 12

This example describes the synthesis of a version of Fragment A, designated as Fragment A2, to make 21-hydroxy-10,11-dehydroepothilone D. Fragment A2 is (5S)-2-iodo-6-methyl-7-(2-(2,2,2-trichloroethoxycarbonyloxy)methylthiazol-4-yl)-5-(triethylsilyloxy)-2,6-heptadiene whose structure is shown below.

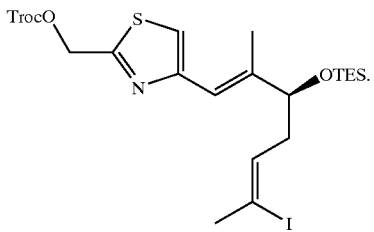

Fragment A2 is a common intermediate in the Heck coupling and the Suzuki coupling routes to 21-hydroxy-10,11-dehydroepothilone D. Fragment A2 can be joined with Fragment B1 whose synthesis was described in Example 8 in a Heck coupling reaction. Alternatively, Fragment A2 can be joined with Fragment B2 whose synthesis was described in Example 9 in a Suzuki coupling reaction. The synthesis of 21-hydroxy-10,11-dehydroepothilone D from Fragments A2 and B1 and from Fragments A2 and B2 is described in Example 13.

(a) ethyl 2-(2,2,2-trichloroethoxycarbonyloxymethyl)thiazole-4-carboxylate

To a solution of ethyl 2-(hydroxymethyl)-thiazole-4-carboxylate 33 (38.4 g) and pyridine (41 mL) in 100 mL of $CH_2Cl_2$ is slowly added 2,2,2-trichloroethyl chloroformate (32 mL, 0.23 mol) at 0° C. After the resulting mixture is stirred for 30 minutes, the reaction is quenched by the addition of 10% aq NaHCO3. The organic layer is separated, and the aqueous layer is extracted with $CH_2Cl_2$. The combined organic extracts are washed with 2 N HCl, 10% aq $NaHCO_3$, and brine, dried ($Na_2SO_4$), and concentrated. The residue is then recrystallized in ethanol (50 mL) to yield a light yellow solid (35 g). The mother liquor is concentrated and chromatographed to afford an additional amount (35 g) of product.

(b) 2-(2,2,2-trichloroethoxycarbonyloxymethyl)thiazole-4-carboxaldehyde

To a solution of ethyl 2-(2,2,2-trichloroethoxycarbonyloxymethyl)thiazole-4-carboxylate (23 g) in $CH_2Cl_2$ (200 mL) is added a solution of diisobutylaluminum hydride (1.0 M in $CH_2Cl_2$, 120 mL) at −78° C. over 30 minutes. The resulting mixture is kept at −78° C. for 10 hours. The excess hydride is quenched with acetic acid (5 mL) and the reaction is warmed to ambient temperature, and the mixture is stirred with sat. aq. Rochelle's salt (150 mL) until the suspension clears. The organic layer is washed with 10% aq $NaHCO_3$ and brine, dried ($Na_2SO_4$), filtered, and concentrated. Purification by column chromatography on $SiO_2$ (toluene/ethyl acetate, 6:1) affords the product as a light yellow syrup (16 g).

(c) 2-methyl-3-(2-(2,2,2-trichloroethoxycarbonyloxymethyl)thiazol-4-yl)propenal

A mixture of 2-(2,2,2-trichloroethoxycarbonyloxymethyl)thiazole-4-carboxaldehyde (21.0 g) and 2-(triphenylphosphoranylidene)propionaldehyde (20.6 g) in 300 mL of benzene is heated at reflux for 3 hours, then cooled to ambient temperature and concentrated. Purification by flash column chromatography on SiO2 (hexanes/ethyl acetate, 4:1) yields the product as a clear oil (21.0 g).

(d) (4S)-4-hydroxy-5-methyl-6-(2-(2,2,2-trichloroethoxycarbonyloxymethyl)-thiazol-4-yl)-1,5-hexadiene A solution of 2-methyl-3-(2-((2,2,2-trichloroethoxycarbonyloxymethyl)thiazol-4-yl)propenal (9.20 g) in 50 mL of anhydrous ether is cooled to −100° C. A pentane solution of (+)-diisopinocampheylallylborane (1.5 equiv) is added dropwise to the vigorously stirred aldehyde solution. After the addition is complete, the reaction mixture is stirred for 1.5 hours and warmed to −50° C. A solution of 30% aq H2O2 (20 mL) and 10% aq NaHCO3 (50 mL) is added, and the resulting turbid mixture is stirred at 25° C. for 8 hours. The organic layer is separated, and the aqueous layer is extracted with ether. The combined organic layers are washed with satd aq $Na_2S_2O_3$ and brine, dried ($MgSO_4$), filtered, and concentrated. Purification by flash column chromatography on $SiO_2$ (hexanes/ethyl acetate, 10:1) affords the alcohol as a clear oil (7.65 g).

(e) (4S)-4-(triethylsilyloxy)-5-methyl-6-(2-(2,2,2-trichloroethoxycarbonyloxymethyl)-thiazol-4-yl)-1,5-hexadiene Triethylsilyl trifluromethanesulfonate (15 mL) is added dropwise to a −78° C. solution of (4S)-4-hydroxy-5-methyl-6-(2-(2,2,2-trichloroethoxycarbonyloxymethyl)-thiazol-4-yl)-1,5-hexadiene (7.65 g) and 2,6-lutidine (10 mL) in 50 mL of $CH_2Cl_2$. After the addition, the reaction mixture is allowed to warm to ambient temperature and is stirred for 5 hours. The reaction mixture is poured into 2 N HCl and extracted with ether. The combined organic layers were washed with 10% aq $NaHCO_3$ and brine, dried ($Na_2SO_4$), filtered, and concentrated. Flash chromatography on $SiO_2$ (hexanes/ethyl acetate, 20:1) provides the product as a colorless oil (9.39 g).

(f) (3S)-3-(triethylsilyloxy)-4-methyl-5-(2-(2,2,2-trichloroethoxycarbonyloxy-methyl)-thiazol-4-yl)-pent-4-enal Osmium tetraoxide (1 wt % in THF, 20.3 mL) is added to a mixture of (4S)-4-(triethylsilyloxy)-5-methyl-6-(2-(2,2,2-trichloroethoxycarbonyloxymethyl)-thiazol-4-yl)-1,5-hexadiene (20.6 g), $H_2O$ (21 mL), and N-methylmorpholine N-oxide (50% in THF, 10 mL, 0.048 mol) in tert-butanol (155 mL) at 0° C. After the resulting mixture is stirred for 12 hours, $Na_2SO_3$ (10 g) and water (5 mL) are added. The resulting solution is stirred at 25° C. for 30 minutes and then extracted with ether. The combined extracts are washed with brine, dried ($Na_2SO_4$), filtered, and concentrated. Purification by flash chromatography on $SiO_2$ provides a 1:1 diastereomeric mixture of the diol as a colorless, viscous oil (18.8 g, 85%). Lead tetraacetate (19.1 g) is added portionwise over 5 minutes to a suspension of the diol (18.0 g) and $Na_2CO_3$ (8.67 g) in 500 mL of benzene at 0° C. After stirring for 15 minutes, the mixture is filtered through a $SiO_2$ pad to afford the aldehyde product (14.0 g, 82%). The product is directly subjected to the next reaction.

(g) (5S)-2-iodo-6-methyl-7-(2-(2,2,2-trichloroethoxycarbonyloxy)methylthiazol-4-yl)-5-(triethylsilyloxy)-2,6-heptadiene To a suspension of ethyltriphenylphosphonium iodide (7.90 g) in THF (150 mL) is added n-butyllithium (7.17 mL, 2.5 M in hexane) at ambient temperature. After disappearance of the solid material, the red solution is cannulated into a vigorously stirred solution of iodine (4.54 g) in THF (150 mL) at −78° C. The resulting dark brown suspension is stirred for 5 minutes and allowed to warm gradually to −30° C. A solution of sodium hexamethyldisilazide (17.3 mL, 1.0 M in THF) is added dropwise to afford a dark red solution. A solution of (3S)-3-(triethylsilyloxy)-4-methyl-5-(2-(2,2,2- trichloroethoxy-carbonyloxy-methyl)-thiazol-4-yl))-pent-4-enal (3.10 g) in THF (10 mL) is slowly added, and stirring is continued at −30° C. for 30 minutes. The reaction mixture is diluted with pentane (100 mL), filtered through a pad of Celite, and concentrated. Purification by flash column chromatography on $SiO_2$ (hexane/ethyl acetate, 15:1) affords the vinyl iodide as a yellow syrup (1.50 g).

EXAMPLE 13

This example describes the synthesis of 21-hydroxy-10,11-dehydro-epothilone D from the Heck coupling of Fragments A2 and B1 or from the Suzuki coupling of Fragments A2 and B2. The product of both couping reactions tert-butyl (3S,6R,7S,8S,10E,12Z,15S,16E)-5-oxo-3,15-bis(triethylsilyloxy)-17-(2-(2,2,2-trichloroethoxycarbonyloxymethyl)thiazol-4-yl)-4,4,6,8,12,16-hexamethyl-7-(2,2,2-trichloroethoxycarbonyloxy)-heptadeca-10,12,16-trienoate which is made in subpart (a) of this example where method A is the Heck coupling route and method B is the Suzuki coupling route.

(a) tert-butyl (3S,6R,7S,8S,10E,12Z,15S,16E)-5-oxo-3,15-bis(triethylsilyloxy)-17-(2-(2,2,2-trichloroethoxycarbonyloxymethyl)thiazol-4-yl)-4,4,6,8,12,16-hexamethyl-7-(2,2,2-trichloroethdxycarbonyloxy)-heptadeca-10,12,16-trienoate Method A: A solution of tert-butyl (3S,6R,7S,8S)-5-oxo-3-(triethylsilyloxy)-4,4,6,8-tetramethyl-7-(2,2,2-trichloroethoxycarbonyloxy)-10-undecenoate (2.12 g) in 4 mL of THF is added to a vigorously stirred mixture of (5S)-2-iodo-6-methyl-7-(2-(2,2,2-trichloroethoxycarbonyloxymethyl)thiazol-4-yl)-5-(triethylsilyloxy)-2,6-heptadiene (2.0 g), cesium carbonate (1.49 g), triphenylarsine (0.188 g), and (dppf)PdCl2·$CH_2Cl_2$ (0.25 g) in 2 mL of degassed dimethylformamide cooled to 0° C. The reaction is stirred for 15 hours, then poured into 10% $NaHSO_4$ and extracted with ethyl acetate. The organic phase is separated, washed sequentially with 10% $NaHCO_3$ and brine, dried over $MgSO_4$, filtered, and evaporated. The product is purified by flash chromatography on $SiO_2$ (10:1 hexanes/ethyl acetate).

Method B: A solution of tert-butyl (3S,6R,7S,8S)-5-oxo-3-(triethylsilyloxy)-4,4,6,8-tetramethyl-7-(2,2,2-trichloroethoxycarbonyloxy)-10-undecynoate (2.1 g) in 4 mL of THF is added to a 1.0 M solution of catecholborane in THF (3.3 mL), the mixture is stirred for 2 hour at 60° C. The resulting solution is added to a vigorously stirred mixture of (5S)-2-iodo-6-methyl-7-(2-(2,2,2-trichloroethoxycarbonyl-oxymethyl)thiazol-4-yl)-5-(triethylsilyloxy)-2,6-heptadiene (2.0 g), triphenylarsine (0.188 g), and (dppf)$PdCl_2$·$CH_2Cl_2$ (0.25 g) in 2 mL of degassed dimethylformamide cooled to 0° C. The reaction is stirred for 15 hours, then poured into 10% $NaHSO_4$ and extracted with ethyl acetate. The organic phase is separated, washed sequentially with 10% $NaHCO_3$ and brine, dried over $MgSO_4$, filtered, and evaporated. The product is purified by flash chromatography on $SiO_2$ (10:1 hexanes/ethyl acetate).

(b) (3S,6R,7S,8S,10E,12Z,15S,16E)-5-oxo-3-(triethylsilyloxy)-15-hydroxy-17-(2-(2,2,2-trichloroethoxycarbonyloxymethyl)thiazol-4-yl)-4,4,6,8,12,16-hexamethyl-7-(2,2,2-trichloroethoxycarbonyloxy)-heptadeca-10,12,16-trienoic acid A solution of tert-butyl (3S,6R,7S,8S,10E,12Z,15S,16E)-5-oxo-3,15-bis(triethylsilyloxy)-17-(2-(2,2,2-trichloroethoxycarbonyloxymethyl)thiazol-4-yl)-4,4,6,8,12,16-hexamethyl-7-(2,2,2-trichloroethoxycarbonyloxy)-heptadeca-10,12,16-trienoate (2.8 g) in 12 mL of $CH_2Cl_2$ is treated with 2,6-lutidine (0.86 mL) and triethylsilyl trifluoromethanesulfonate (0.98 g) at 0° C. for 30 minutes, then at ambient temperature for 10 hours. The mixture is diluted with 50 mL of ethyl acetate and poured into 20 mL of 1 N HCl. The organic phase is separated, washed with pH 7 phosphate buffer, dried with $Na_2SO_4$, filtered, and concentrated. The residue is dissolved in 5 mL of THF and treated with 0.5 mL of 0.1 N HCl in methanol. The reaction is monitored by thin-layer chromatography, with additional aliquots of methanolic HCl being added to achieve complete reaction. When complete, the reaction is poured into 15 mL of pH 7 phosphate buffer and extracted with ethyl acetate. The extract is washed with brine, dried with $Na_2SO_4$, filtered, and evaporated. The product is purified by flash chromatography on $SiO_2$ (1:1 hexanes/ethyl acetate).

(c) 7,21-bis-O-(2,2,2-trichloroethoxycarbonyl)-3-O-(triethylsilyl)-10,11-dehydro-epothilone D A solution of (3S,6R,7S,8S,10E,12Z,15S,16E)-5-oxo-3-(triethylsilyloxy)-15-hydroxy-17-(2-(2,2,2-trichloroethoxycarbonyloxymethyl)thiazol-4-yl)-4,4,6,8,12,16-hexamethyl-7-(2,2,2-trichloroethoxycarbonyloxy)-heptadeca-10,12,16-trienoic acid (0.42 g) in 9 mL of THF is treated with triethylamine (0.36 mL) and 2,4,6-trichlorobenzoyl chloride (0.528 g). After 15 minutes, 40 mL of toluene is added, and the resulting solution is added via syringe pump over 3 hours to a solution of 4-dimethylaminopyridine (0.525 g) in 400 mL of toluene. After an additional 1 hour, the mixture is filtered through Celite and concentrated. The product is purified by flash chromatography on $SiO_2$ (2:1 hexanes/ethyl acetate).

(d) 21-hydroxy-3-O-(triethylsilyl)-10,11-dehydro-12,13-epothilone D

A solution of 7,21-bis-O-(2,2,2-trichloroethoxycarbonyl)-3-O-(triethylsilyl)-10,11-dehydro-12,13-desoxyepothilone F (0.19 g) in 1 mL of THF is added to a stirred suspension of activated zinc dust (0.261 g) in 2 mL of acetic acid. After stirring for 1.5 hours, the mixture is diluted with ethyl acetate and filtered. The filtrate is washed sequentially with 10% $NaHCO_3$ and brine, dried over $MgSO_4$, filtered, and evaporated. The product is purified by flash chromatography on $SiO_2$ (2:1 hexanes/ethyl acetate).

(e) 21-hydroxy-10,11-dehydro-epothilone D

A solution of 3-O-(triethylsilyl)-10,11-dehydro-12,13-desoxyepothilone F (80 mg) in 2 mL of THF in a polyethylene vessel and treated with 1.5 mL of HF-pyridine for 1 hour at 0° C. and 30 minutes at ambient temperature, then diluted with 30 mL of ethyl acetate and poured into 20 mL of sat. aq. $NaHCO_3$. The organic phase is separated and washed sequentially with 1 N HCl, 10% $NaHCO_3$, and brine, then dried over $MgSO_4$, filtered, and evaporated. The product is purified by flash chromatography on $SiO_2$ (1:2 hexanes/ethyl acetate).

EXAMPLE 14

(5S)-2-iodo-5-(6-quinolyl)-5-(triethylsilyloxy)-2-pentene

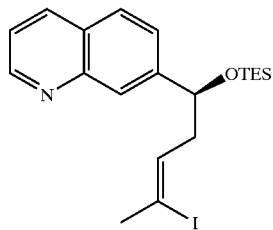

(a) (2R)-N-[(3S)-3-hydroxy-3-(6-quinolyl)propionyl]-2,10-camphorsultam

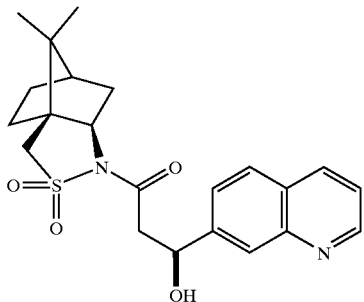

A 1.0 M solution of diethylboron triflate in CH$_2$Cl$_2$ (110 mL) is added slowly to a 0° C. solution of 25.7 g of (2R)-N-acetyl-2,10-camphorsultam (Oppolzer et al. 1992, *Tetrahedron Letters* 33, 2439) in 250 mL of CH$_2$Cl$_2$. A solution of diisopropylethylamine (15 mL) in 75 mL of CH$_2$Cl$_2$ is then added dropwise over 20 minutes at 0° C., and the mixture is then cooled to −78° C. A solution of quinoline-6-carboxaldehyde (15.7 g) in 100 mL of CH$_2$Cl$_2$ is then added at such a rate as to keep the reaction temperature below −70° C. After an additional 2 hours, the mixture is warmed to ambient temperature and quenched by addition of 100 mL of 3:1 tetrahydrofuran/water and 750 mL of sat. aq. NH$_4$Cl. The mixture is concentrated to a slurry, then diluted with water, adjusted to pH 8, and extracted with ethyl acetate. The extract is washed sequentially with water and brine, then dried over MgSO$_4$, filtered, and evaporated to yield the crude adduct. Purification by silica gel chromatography yields pure (2R)-N-[3-hydroxy-3-(6-quinolyl)propionyl]bornane-2,10-camphorsultam.

(b) (2R)-N-[(3S)-3-(triethylsilyloxy)-3-(6-quinolyl)propionyl]-2,10-camphorsultam

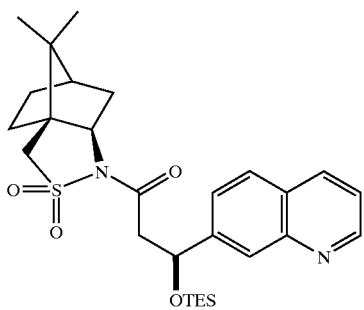

A solution of (2R)-N-[3-hydroxy-3-(6-quinolyl)propionyl]-2,10-camphorsultam (41.4 gm) in 250 mL of CH$_2$Cl$_2$ is cooled on ice and treated with 2,6-lutidine (13 gm) and triethylsilyl trifluoromethanesulfonate (29 gm). After stirring for 12 hours, the mixture is washed with water and dried over MgSO$_4$, filtered, and evaporated to yield the crude product. Purification by silica gel chromatography yields pure (2R)-N-[3-(triethylsilyloxy)-3-(6-quinolyl)-propionyl]-2,10-camphorsultam.

(c) (3S)-3-(triethylsilyloxy)-3-(6-quinolyl)propanal

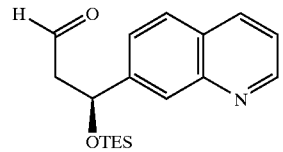

A solution of (2R)-N-[3-(triethylsilyloxy)-3-(6-quinolyl)-propionyl]bomane-10,2-sultam (52.8 gm) in 1000 mL of CH$_2$Cl$_2$ is cooled to −78° C., and a 1.0 M solution of diisobutylaluminum hydride in hexane is added dropwise so as to keep the reaction temperature below −65° C. The mixture is stirred for an additional 6 hours at −78° C., then is quenched by addition of sat. aq. NH4Cl and allowed to warm to ambient temperature. The mixture is washed with brine, and the organic phase is dried over MgSO$_4$, filtered, and evaporated. The product is purified by silica gel chromatography.

(d) (5S)-2-iodo-5-(6-quinolyl)-5-(triethylsilyloxy)-2-pentene

A suspension of ethyltriphenylphosphonium iodide (7.9 gm) in 150 mL of tetrahydrofuran is treated with a 2.5 M solution of n-butyllithium (7.17 mL) at ambient temperature. The resulting red solution is transferred via cannula into a vigorously stirred solution of iodine (4.54 gm) in 150 mL of tetrahydrofuran cooled to −78° C. The resulting suspension is stirred for 5 minutes, then gradually warmed to −30° C. A 1.0 M solution of sodium hexamethyldisilazide (17.3 mL) is then added dropwise to form a red solution. A solution of (3S)-3-(triethylsilyloxy)-3-(6-quinolyl)propanal (1.9 gm) in 10 mL of tetrahydrofuran is then added dropwise, and stirring is continued at −30° C. for 30 minutes. The mixture is diluted with ether, filtered through a pad of Celite, and concentrated. The product is purified by flash chromatography on silica gel.

EXAMPLE 15

(5S)-2-iodo-5-(2-methylbenzothiazol-5-yl)-5-(triethylsilyloxy)-2-pentene

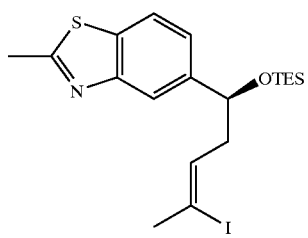

Is prepared according to the method of Example 14, replacing quinoline-6-carboxaldehyde with 2-methylbenzothiazole-5-carboxaldehyde.

EXAMPLE 16
(6S)-3-iodo-6-(6-guinolyl)-6-(triethylsilyloxy)-3-hexene

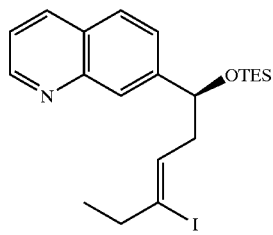

A suspension of propyltriphenylphosphonium iodide (8.2 gm) in 150 mL of tetrahydrofuran is treated with a 2.5 M solution of n-butyllithium (7.17 mL) at ambient temperature. The resulting red solution is transferred via cannula into a vigorously stirred solution of iodine (4.54 gm) in 150 mL of tetrahydrofuran cooled to −78° C. The resulting suspension is stirred for 5 minutes, then gradually warmed to −30° C. A 1.0 M solution of sodium hexamethyldisilazide (17.3 mL) is then added dropwise to form a red solution. A solution of (3S)-3-(triethylsilyloxy)-3-(6-quinolyl)propanal (1.9 gm) in 10 mL of tetrahydrofuran is then added dropwise, and stirring is continued at −30° C. for 30 minutes. The mixture is diluted with ether, filtered through a pad of Celite, and concentrated. The product is purified by flash chromatography on silica gel.

EXAMPLE 17
(4S,5S)-2-iodo-4,6-dimethyl-7-(2-methylthiazol-4-yl)-5-(triethylsilyloxy)-2,6-heptadiene

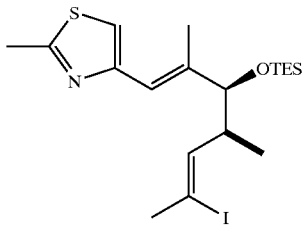

(a) (3S,4S)-4-hydroxy-3,5-dimethyl-6-(2-methylthiazol-4-yl))-1,5-hexadiene

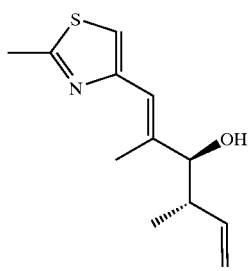

A solution of 2-methyl-3-(2-methylthiazol-4-yl))propenal (4.3 g) in 50 mL of anhydrous ether is cooled to −100° C. A pentane solution of (+)-diisopinocampheyl-trans-crotylborane (1.5 equiv) is added dropwise to the vigorously stirred aldehyde solution. After the addition is complete, the reaction mixture is stirred for 1.5 hours and warmed to −50° C. A solution of 30% aq H2O2 (20 mL) and 10% aq NaHCO3 (50 mL) is added, and the resulting turbid mixture is stirred at 25° C. for 8 hours. The organic layer is separated, and the aqueous layer is extracted with ether. The combined organic layers are washed with satd aq Na$_2$S$_2$O$_3$ and brine, dried (MgSO4), filtered, and concentrated. Purification by flash column chromatography on SiO$_2$ (hexanes/ethyl acetate, 10:1) affords the alcohol as a clear oil.

(b) (3S,4S)-4-(triethylsilyloxy)-3,5-dimethyl-6-(2-methylthiazol-4-yl))-1,5-hexadiene

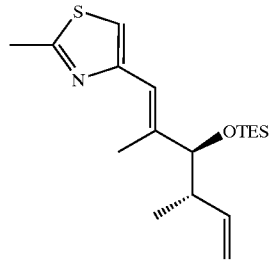

Triethylsilyl trifluromethanesulfonate (15 mL) is added dropwise to a −78° C. solution of (3S,4S)-4-hydroxy-3,5-dimethyl-6-(2-methylthiazol-4-yl)-1,5-hexadiene (4.3 g) and 2,6-lutidine (10 mL) in 50 mL of CH$_2$Cl$_2$. After the addition, the reaction mixture is allowed to warm to ambient temperature and is stirred for 5 hours. The reaction mixture is poured into 2 N HCl and extracted with ether. The combined organic layers were washed with 10% aq NaHCO$_3$ and brine, dried (Na$_2$SO$_4$), filtered, and concentrated. Flash chromatography on SiO$_2$ (hexanes/ethyl acetate, 20:1) provids the product as a colorless oil.

(c) (2R,3S)-3-(triethylsilyloxy)-2,4-dimethyl-5-(2-methylthiazol-4-yl))-pent-4-enal

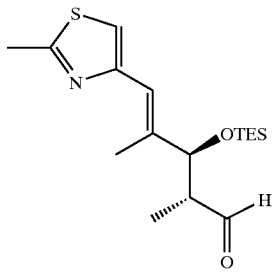

Osmium tetraoxide (1 wt % in THF, 20.3 mL) is added to a mixture of (3S,4S)-4-(triethylsilyloxy)-3,5-dimethyl-6-(2-methylthiazol-4-yl)-1,5-hexadiene (13.5 g), H$_2$O (21 mL), and N-methylmorpholine N-oxide (50% in THF, 10 mL, 0.048 mol) in tert-butanol (155 mL) at 0° C. After the resulting mixture is stirred for 12 hours, Na$_2$SO$_3$ (10 g) and water (5 mL) are added. The resulting solution is stirred at 25° C. for 30 minutes and then extracted with ether. The combined extracts are washed with brine, dried (Na$_2$SO$_4$), filtered, and concentrated. Purification by flash chromatography on SiO$_2$ provides a 1:1 diastereomeric mixture of the diol as a colorless, viscous oil. Lead tetraacetate (19.1 g) is added portionwise over 5 minutes to a suspension of the diol (18.0 g) and Na$_2$CO$_3$ (8.67 g) in 500 mL of benzene at 0° C. After stirring for 15 minutes, the mixture is filtered through a SiO$_2$ pad to afford the aldehyde product. The product is directly subjected to the next reaction.

(d) (5S)-2-iodo-6-methyl-7-(2-(2,2,2-trichloroethoxycarbonyloxy)methylthiazol-4-yl)-5-(triethylsilyloxy)-2,6-heptadiene To a suspension of ethyltriphenylphosphonium iodide (7.90 g) in THF (150 mL) is added n-butyllithium (7.17 mL, 2.5 M in hexane) at ambient temperature. After disappearance of the solid material, the red solution is cannulated into a vigorously stirred solution of iodine (4.54 g) in THF (150 mL) at −78° C. The resulting dark brown suspension is stirred for 5 minutes and allowed to warm gradually to −30° C. A solution of sodium hexamethyldisilazide (17.3 mL, 1.0 M in THF) is added dropwise to afford a dark red solution. A solution of (2R,3S)-3-(triethylsilyloxy)-4-methyl-5-(2-methylthiazol-4-yl)-pent-4-enal (2.0 g) in THF (10 mL) is slowly added, and stirring is continued at −30° C. for 30 minutes. The reaction mixture is diluted with pentane (100 mL), filtered through a pad of Celite, and concentrated. Purification by flash column chromatography on $SiO_2$ (hexane/ethyl acetate, 15:1) affords the vinyl iodide as a yellow syrup.

EXAMPLE 18

(5S)-5-azido-2-iodo-6-methyl-7-(2-methylthiazol-4-yl)-2,6-heptadiene

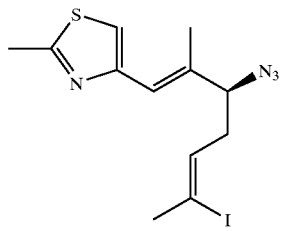

(a) (4R)-4-hydroxy-3,5-dimethyl-6-(2-methylthiazol-4-yl))-1,5-hexadiene

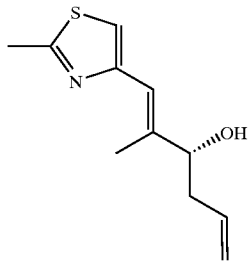

A solution of 2-methyl-3-(2-methylthiazol-4-yl))propenal (4.3 g) in 50 mL of anhydrous ether is cooled to −100° C. A pentane solution of (−)-diisopinocamnpheylallylborane (1.5 equiv) is added dropwise to the vigorously stirred aldehyde solution. After the addition is complete, the reaction mixture is stirred for 1.5 hours and warmed to −50° C. A solution of 30% aq $H_2O_2$ (20 mL) and 10% aq $NaHCO_3$ (50 mL) is added, and the resulting turbid mixture is stirred at 25° C. for 8 hours. The organic layer is separated, and the aqueous layer is extracted with ether. The combined organic layers are washed with satd aq $Na_2S_2O_3$ and brine, dried ($MgSO_4$), filtered, and concentrated. Purification by flash column chromatography on $SiO_2$ (hexanes/ethyl acetate, 10:1) affords the alcohol as a clear oil.

(b) (4R)-4-(triethylsilyloxy)-5-methyl-6-(2-methylthiazol-4-yl))-1,5-hexadiene

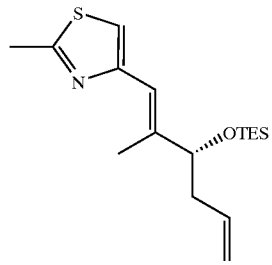

Triethylsilyl trifluromethanesulfonate (15 mL) is added dropwise to a −78° C. solution of (4R)-4-hydroxy-5-methyl-6-(2-methylthiazol-4-yl))-1,5-hexadiene (4.3 g) and 2,6-lutidine (10 mL) in 50 mL of $CH_2Cl_2$. After the addition, the reaction mixture is allowed to warm to ambient temperature and is stirred for 5 hours. The reaction mixture is poured into 2 N HCl and extracted with ether. The combined organic layers were washed with 10% aq $NaHCO_3$ and brine, dried ($Na_2SO_4$), filtered, and concentrated. Flash chromatography on $SiO_2$ (hexanes/ethyl acetate, 20:1) provids the product as a colorless oil.

(c) (3R)-3-(triethylsilyloxy)-4-methyl-5-(2-methylthiazol-4-yl)-pent-4-enal

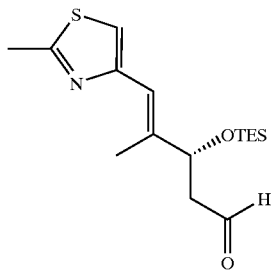

Osmium tetraoxide (1 wt % in THF, 20.3 mL) is added to a mixture of (4R)-4-(triethylsilyloxy)-5-methyl-6-(2-methylthiazol-4-yl)-1,5-hexadiene (13.5 g), $H_2O$ (21 mL), and N-methylmorpholine N-oxide (50% in THF, 10 mL, 0.048 mol) in tert-butanol (155 mL) at 0° C. After the resulting mixture is stirred for 12 hours, $Na_2SO_3$ (10 g) and water (5 mL) are added. The resulting solution is stirred at 25° C. for 30 minutes and then extracted with ether. The combined extracts are washed with brine, dried ($Na_2SO_4$), filtered, and concentrated. Purification by flash chromatography on $SiO_2$ provides a 1:1 diastereomeric mixture of the diol as a colorless, viscous oil. Lead tetraacetate (19.1 g) is added portionwise over 5 minutes to a suspension of the diol (18.0 g) and $Na_2CO_3$ (8.67 g) in 500 mL of benzene at 0° C. After stirring for 15 minutes, the mixture is filtered through a $SiO_2$ pad to afford the aldehyde product. The product is directly subjected to the next reaction.

(d) (5R)-2-iodo-6-methyl-7-(2-methylthiazol-4-yl)-5-(triethylsilyloxy)-2,6-heptadiene

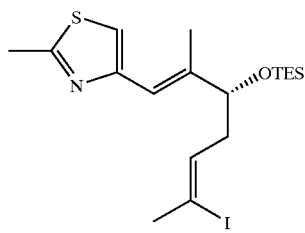

To a suspension of ethyltriphenylphosphonium iodide (7.90 g) in THF (150 mL) is added n-butyllithium (7.17 mL, 2.5 M in hexane) at ambient temperature. After disappearance of the solid material, the red solution is cannulated into a vigorously stirred solution of iodine (4.54 g) in THF (150 mL) at −78° C. The resulting dark brown suspension is stirred for 5 minutes and allowed to warm gradually to −30° C. A solution of sodium hexamethyldisilazide (17.3 mL, 1.0 M in THF) is added dropwise to afford a dark red solution. A solution of (3R)-3-(triethylsilyloxy)-4-methyl-5-(2-methylthiazol-4-yl)-pent-4-enal (2.0 g) in THF (10 mL) is slowly added, and stirring is continued at −30° C. for 30 minutes. The reaction mixture is diluted with pentane (100 mL), filtered through a pad of Celite, and concentrated. Purification by flash column chromatography on SiO$_2$ (hexane/ethyl acetate, 15:1) affords the vinyl iodide.

(e) (5R)-5-hydroxy-2-iodo-6-methyl-7-(2-methylthiazol-4-yl)-2,6-heptadiene

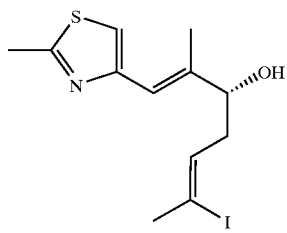

A solution of (5R)-2-iodo-6-methyl-7-(2-methylthiazol-4-yl)-5-(triethylsilyloxy)-2,6-heptadiene (2.28 g) in 50 mL of 3:1:1 acetic acid/THF/water is stirred at ambient temperature for 8 hoursours, then concentrated. The residue is dissolved in ethyl acetate, washed sequentially with sat. NaHCO$_3$ and brine, then dried over MgSO$_4$, filtered, and evaporated. The product is purified by SiO$_2$ chromatography (30% ethyl acetate/hexanes).

(f) (5S)-5-azido-2-iodo-6-methyl-7-(2-methylthiazol-4-yl)-2,6-heptadiene

A solution of (5R)-5-hydroxy-2-iodo-6-methyl-7-(2-methylthiazol-4-yl)-2,6-heptadiene (1.74 g) in 30 mL of toluene is cooled to 0° C. and treated with diphenylphosphoryl azide (1.65 g) and 1,8-diazabicyclo[5.4.0]undec-7-ene (0.91 g) for 2 hours. The mix is warmed to ambient temperature and diluted with ethyl acetate. The solution is washed sequentially with water, sat. NaHCO$_3$, and brine, then dried over MgSO$_4$, filtered, and evaporated. The product is purified by SiO$_2$ chromatography (7.5% ethyl acetate/hexanes).

EXAMPLE 19

(5S)-5-azido-2-iodo-5-(6-quinolyl)-2-pentene

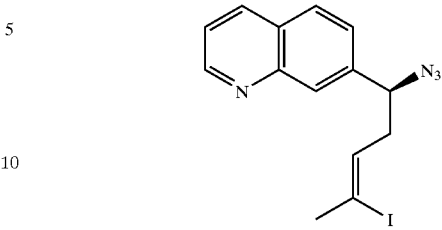

(a) (2S)-N-[(3R)-3-hydroxy-3-(6-quinolyl)propionyl]-2,10-camphorsultam

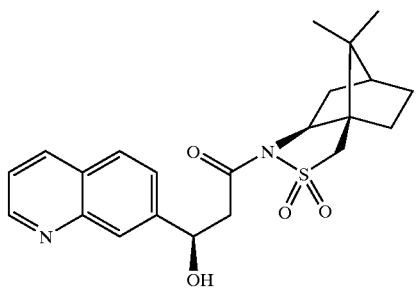

A 1.0 M solution of diethylboron triflate in CH$_2$Cl$_2$ (110 mL) is added slowly to a 0° C. solution of 25.7 gm of (2S)-N-acetyl-2,10-camphorsultam in 250 mL of CH$_2$Cl$_2$. A solution of diisopropylethylamine (15 mL) in 75 mL of CH$_2$Cl$_2$ is then added dropwise over 20 minutes at 0° C., and the mixture is then cooled to −78° C. A solution of quinoline-6-carboxaldehyde (15.7 g) in 100 mL of CH$_2$Cl$_2$ is then added at such a rate as to keep the reaction temperature below −70° C. After an additional 2 hours, the mixture is warmed to ambient temperature and quenched by addition of 100 mL of 3:1 tetrahydrofuran/water and 750 mL of sat. aq. NH$_4$Cl. The mixture is concentrated to a slurry, then diluted with water, adjusted to pH 8, and extracted with ethyl acetate. The extract is washed sequentially with water and brine, then dried over MgSO$_4$, filtered, and evaporated to yield the crude adduct. Purification by silica gel chromatography yields pure product.

(b) (2S)-N-[(3R)-3-(triethylsilyloxy)-3-(6-quinolyl)propionyl]-2,10-camphorsultam

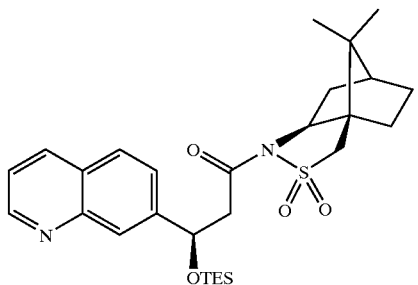

A solution of (2S)-N-[(3R)-3-hydroxy-3-(6-quinolyl)propionyl]-2,10-camphorsultam (41.4 gm) in 250 mL of CH$_2$Cl$_2$ is cooled on ice and treated with 2,6-lutidine (13 gm) and triethylsilyl trifluoromethanesulfonate (29 gm). After stirring for 12 hours, the mixture is washed with water and dried over MgSO$_4$, filtered, and evaporated to yield the crude product. Purification by silica gel chromatography yields pure product.

(c) (3R)-3-(triethylsilyloxy)-3-(6-quinolyl)propanal

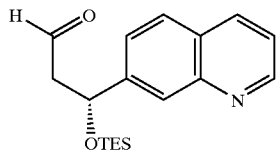

A solution of (2S)-N-[(3R)-3-(triethylsilyloxy)-3-(6-quinolyl)-propionyl]-2,10-camphorsultam (52.8 gm) in 1000 mL of CH$_2$Cl$_2$ is cooled to −78° C., and a 1.0 M solution of diisobutylaluminum hydride in hexane is added dropwise so as to keep the reaction temperature below −65° C. The mixture is stirred for an additional 6 hours at −78° C., then is quenched by addition of sat. aq. NH$_4$Cl and allowed to warm to ambient temperature. The mixture is washed with brine, and the organic phase is dried over MgSO$_4$, filtered, and evaporated. The product is purified by silica gel chromatography.

(d) (5R)-2-iodo-5-(6-quinolyl)-5-(triethylsilyloxy)-2-pentene

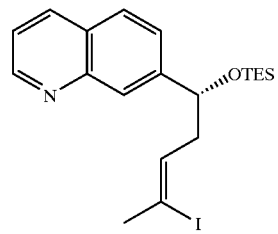

A suspension of ethyltriphenylphosphonium iodide (7.9 gm) in 150 mL of tetrahydrofuran is treated with a 2.5 M solution of n-butyllithium (7.17 mL) at ambient temperature. The resulting red solution is transferred via cannula into a vigorously stirred solution of iodine (4.54 gm) in 150 mL of tetrahydrofuran cooled to −78° C. The resulting suspension is stirred for 5 minutes, then gradually warmed to −30° C. A 1.0 M solution of sodium hexamethyldisilazide (17.3 mL) is then added dropwise to form a red solution. A solution of(3R)-3-(triethylsilyloxy)-3-(6-quinolyl)propanal (1.9 gm) in 10 mL of tetrahydrofuran is then added dropwise, and stirring is continued at −30° C. for 30 minutes. The mixture is diluted with ether, filtered through a pad of Celite, and concentrated. The product is purified by flash chromatography on silica gel.

(e) (5R)-2-iodo-5-(6-quinolyl)-5-hydroxy-2-pentene

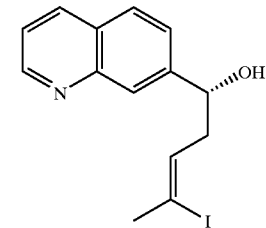

A solution of (5R)-2-iodo-5-(6-quinolyl)-5-(triethylsilyloxy)-2-pentene (2.26 g) in 50 mL of 3:1:1 acetic acid/THF/water is stirred at ambient temperature for 8 hours, then concentrated. The residue is dissolved in ethyl acetate, washed sequentially with sat. NaHCO$_3$ and brine, then dried over MgSO$_4$, filtered, and evaporated. The product is purified by SiO$_2$ chromatography.

(e) (5S)-5-azido-2-iodo-5-(6-quinolyl)-2-pentene

A solution of (5R)-2-iodo-5-(6-quinolyl)-5-hydroxy-2-pentene (1.74 g) in 30 mL of toluene is cooled to 0° C. and treated with diphenylphosphoryl azide (1.65 g) and 1,8-diazabicyclo[5.4.0]undec-7-ene (0.91 g) for 2 hours. The mix is warmed to ambient temperature and diluted with ethyl acetate. The solution is washed sequentially with water, sat. NaHCO$_3$, and brine, then dried over MgSO$_4$, filtered, and evaporated. The product is purified by SiO$_2$ chromatography.

EXAMPLE 20

Tert-butyl (3S,6R,7S,8S)-5-oxo-3-(triethylsilyloxy)-4,4,6,8,10-pentamethyl-7-(2,2,2-trichloroethoxycarbonyloxy)-10-undecenoate

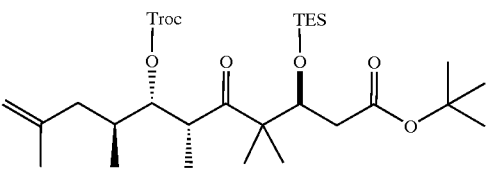

Prepared according to the method of Example 8, substituting (2S)-2,4-dimethyl-4-pentenal in place of (2S)-2-methyl-4-pentenal.

EXAMPLE 21

Tert-butyl (2S,3S,6R,7S,8S)-5-oxo-3-(triethylsilyloxv)-2,4,4,6,8-pentamethyl-7-(2,2,2-trichloroethoxycarbonyloxy)-10-undecenoate

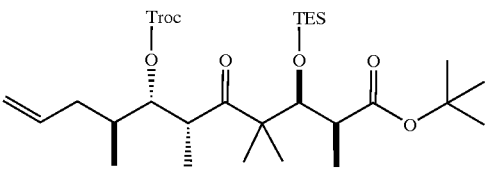

(a) (4S)-3-[(2S,3S,6R,7S,8S)-5-oxo-3-hydroxy-2,4,4,6,8-pentainethyl-7-(2,2,2-trichloroethoxycarbonyloxy)-10-undecenoyl]-4-benzyloxazolidinone

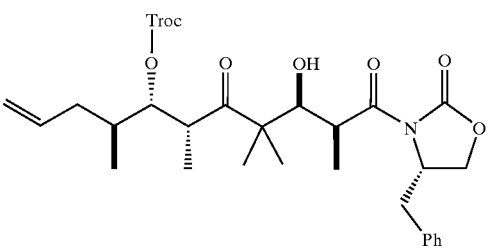

A solution of (4S)-3-propionyl-4-benzyloxazolidinone (91 mmol) in 200 mL of CH$_2$Cl$_2$ at 0° C. is treated sequentially with dibutylboron triflate (27 mL) and triethylamine (16.7 mL) at such a rate so as to keep the reaction temperature below 3° C. After stirring for 30 minutes, the mixture is cooled to −78° C. and treated with a solution of (4R,5S,6S)-3-oxo-5-(2,2,2-trichloroethoxycarbonyloxy)-2,2,4,6-tetramethyl-8-nonenal (90 mmol) in 10 mL of CH$_2$Cl$_2$. After 1 hour, the mixture is allowed to warm slowly to 0° C. and stirred an additional 1 hour. The reaction is quenched by addition of 100 mL of pH 7 phosphate buffer and 300 mL of methanol. A mixture of 2:1 methanol/30% aq. $H_2O_2$ (300 mL) is then added while maintaining the temperature below 10° C. After stirring for 1 hour, the mixture is concentrated under vacuum to a slurry, which is extracted with ether. The extract is washed sequentially with 5% $NaHCO_3$ and brine, dried over $MgSO_4$, filtered, and evaporated. The product is isolated by silica gel chromatography.

(b) (4S)-3-[(2S,3S,6R,7S,8S)-5-oxo-3-(triethylsilyloxy)-2,4,4,6,8-pentamethyl-7-(2,2,2-trichloroethoxycarbonyloxy)-10-undecenoyl]-4-benzyloxazolidinone

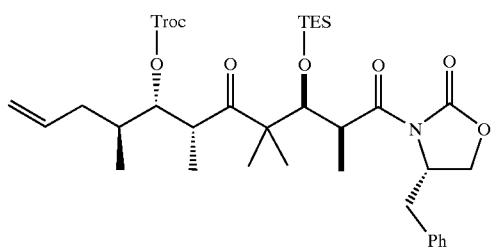

A solution of (4S)-3-[(2S,3S,6R,7S,8S)-5-oxo-3-hydroxy-2,4,4,6,8-pentamethyl-7-(2,2,2-trichloroethoxycarbonyloxy)-10-undecenoyl]-4-benzyloxazolidinone (2.6 g), imidazole (0.48 g), and triethylsilyl chloride (0.68 g) in 5 mL of dimethylformamide is stirred for 2 hours at ambient temperature, then poured into water and extracted with ether. The extract is washed with sat. aq. NaCl, dried over $MgSO_4$, filtered, and evaporated. The product is purified by chromatography on $SiO_2$.

(c) (2S,3S,6R,7S,8S)-5-oxo-3-(triethylsilyloxy)-2,4,4,6,8-pentamethyl-7-(2,2,2-trichloroethoxycarbonyloxy)-10-undecenoic acid

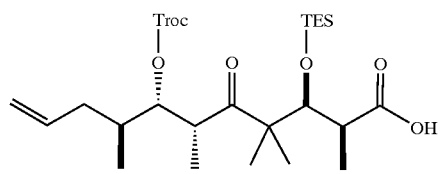

A solution of (4S)-3-[(2S,3S,6R,7S,8S)-5-oxo-3-(triethylsilyloxy)-2,4,4,6,8-pentamethyl-7-(2,2,2-trichloroethoxycarbonyloxy)-10-undecenoyl]-4-benzyloxazolidinone (21.5 g) in 125 mL of 4:1 THF/water is cooled on ice and treated with 10.2 mL of 30% $H_2O_2$ followed by a solution of lithium hydroxide (0.96 g) in 50 mL of water. After 1 hour, a solution of sodium sulfite (12.6 g) in 75 mL of water is added, and the mixture is adjusted to pH 3 and concentrated under vacuum. The resulting slurry is extracted with ethyl acetate. The extract is washed with brine, dried over $MgSO_4$, filtered, and evaporated. The product is purified by chromatography on $SiO_2$.

(d) tert-butyl (2S,3S,6R,7S,8S)-5-oxo-3-(triethylsilyloxy)-2,4,4,6,8-pentamethyl-7-(2,2,2-trichloroethoxycarbonyloxy)-10-undecenoate A solution of (2S,3S,6R,7S,8S)-5-oxo-3-(triethylsilyloxy)-2,4,4,6,8-pentamethyl-7-(2,2,2-trichloroethoxycarbonyloxy)-10-undecenoic acid (11.8 g), tert-butanol (4.5 g), and 4-dimethylaminopyridine (0.2 g) in 20 mL of $CH_2Cl_2$ is cooled on ice and treated with dicyclohexylcarbodiimide (4.6 g) over a 5-minute period. The mixture is allowed to warm to ambient temperature and is stirred for 3 hours. The slurry is diluted with $CH_2Cl_2$ and filtered, and the filtrate is washed sequentially with sat. aq. citric acid, 5% $NaHCO_3$, and brine. The solution is dried over $Na_2SO_4$, filtered, and evaporated. The product is purified by chromatography on $SiO_2$.

EXAMPLE 22

Tert-butyl (3S,7R,8S)-5-oxo-3-(triethylsilyloxy)-4,4,8-trimethyl-7-(2,2,2-trichloroethoxycarbonyloxy)-10-undecenoate

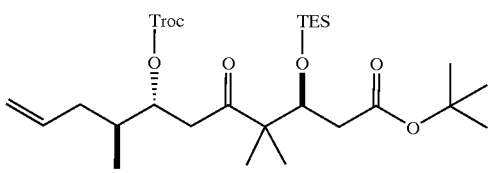

(a) (5R,6S)-1,1-diisopropoxy-5-hydroxy-2,2,6-trimethyl-8-nonen-3-one

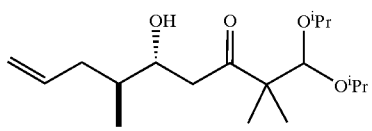

A solution of 1,1-diisopropoxy-2,2,-dimethyl-3-butanone (3.08 g) in 15 mL of ether is added slowly to a solution of lithium diisopropylamide (15.7 mmol) in 20 mL of ether cooled to −78° C., the mixture is stirred for 30 minutes, warmed to −40° C. and stirred for 30 minutes, then recooled to −78° C. A solution of bis(1,2:5,6-di-O-isopropylidene-α-D-glucofuranos-3-O-yl)cyclopentadienyltitanium chloride (17.4 mmol) in 180 mL of ether is added dropwise over 40 minutes, and the reaction is stirred for an additional 30 minutes at −78° C., warmed to −30° C. and kept for 45 minutes, then recooled to −78° C. A solution of (2S)-2-methyl-4-pentenal (16.36 mmol) in 30 mL of ether is added over 10 minutes and the mixture is stirred for 2 hours at −78° C. A 5 M solution of water in THF (28 mL) is added, the mixture is stirred for 1 hour and then filtered through Celite. The filtrate is washed with sat. aq. NaCl, and the brine layer is back extracted with ether. The organic phases are combined, dried with $Na_2SO_4$, filtered, and evaporated. The product is purified by chromatography on $SiO_2$.

(b) (5R,6S)-1,1-diisopropoxy-5-(2,2,2-trichloroethoxycarbonyloxy)-2,2,6-trimethyl-8-nonen-3-one

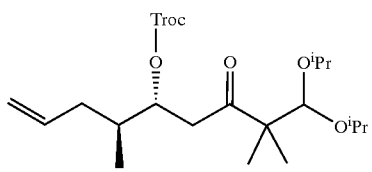

Trichloroethyl chloroformate (2.5 mL) and pyridine (2.95 mL) are added to a solution of (5R,6S)-1,1-diisopropoxy-5-hydroxy-2,2,6-trimethyl-8-nonen-3-one (2.9 g) in 40 mL of $CH_2Cl_2$ at 0° C., and the mixture is stirred for 5 hours before pouring into sat. aq. NaCl and extracting with $CH_2Cl_2$. The extract is dried over $Na_2SO_4$, filtered, and evaporated. The product is purified by chromatography on $SiO_2$.

(c) (5R,6S)-3-oxo-5-(2,2,2-trichloroethoxycarbonyloxy)-2,2,6-trimethyl-8-nonenal

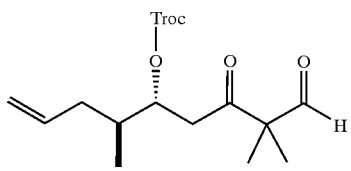

A mixture of (5R,6S)-1,1-diisopropoxy-5-(2,2,2-trichloroethoxycarbonyloxy)-2,2,6-trimethyl-8-nonen-3-one (4.3 g) and p-toluenesulfonic acid monohydrate (0.45 g) in 100 mL of 3:1 THF/water is heated at reflux for 7 hours. The mixture is cooled and poured into sat. aq. NaHCO$_3$, then extracted with ethyl acetate. The extract is dried over Na$_2$SO$_4$, filtered, and evaporated. The product is purified by chromatography on SiO$_2$.

(d) tert-butyl (3S,7R,8S)-5-oxo-3-hydroxy-4,4,8-trimethyl-7-(2,2,2-trichloroethoxy-carbonyloxy)-10-undecenoate

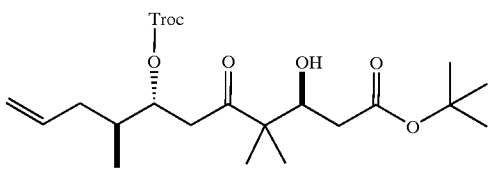

Tert-butyl acetate (0.865 mL) is added to a solution of lithium diisopropylamide (7.52 mmol) in 30 mL of ether at −78° C., and the mixture is stirred for 1 hour. A solution of bis(1,2:5,6-di-O-isopropylidene-α-L-glucofuranos-3-O-yl)cyclopentadienyltitanium chloride (8.34 mmol) in 90 mL of ether is added dropwise over 40 minutes, and the reaction is stirred for an additional 30 minutes at −78° C., warmed to −30° C. and kept for 45 minutes, then recooled to −78° C. A solution of (5R,6S)-3-oxo-5-(2,2,2-trichloroethoxycarbonyl-oxy)-2,2,6-trimethyl-8-nonenal (2.4 g) in 15 mL of ether is added over 10 minutes and the reaction is continued for 2 hours before addition of 14 mL of 5 M water in THF. The mix is stirred for 1 hour, then filtered through Celite. The filtrate is washed with sat. aq. NaCl, and the brine layer is back extracted with ether. The organic phases are combined, dried with Na$_2$SO$_4$, filtered, and evaporated. The product is purified by chromatography on SiO$_2$.

(e) tert-butyl (3S,7R,8S)-5-oxo-3-(triethylsilyloxy)-4,4,8-trimethyl-7-(2,2,2-trichloroethoxy-carbonyloxy)-10-undecenoate A solution of tert-butyl (3S,7R,8S)-5-oxo-3-hydroxy-4,4,8-trimethyl-7-(2,2,2-trichloroethoxycarbonyloxy)-10-undecenoate (1.7 g), imidazole (0.48 g), and triethylsilyl chloride (0.68 g) in 5 mL of dimethylformamide is stirred for 2 hours at ambient temperature, then poured into water and extracted with ether. The extract is washed with sat. aq. NaCl, dried over MgSO$_4$, filtered, and evaporated. The product is purified by chromatography on SiO$_2$.

EXAMPLE 23
Tert-butyl (2S,3S,6R,7S,8S)-5-oxo-3-(triethylsilyloxy)-2,4,4,6,8-pentamethyl-7-(2,2,2-trichloroethoxycarbonyloxy)-10-undecynoate

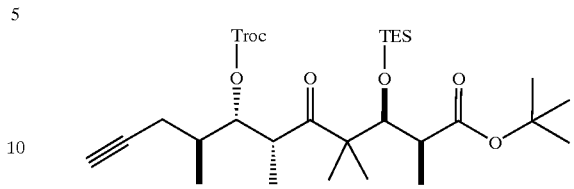

Prepared according to the method of Example 21, substituting (2S)-2-methyl-4-propynal for (2S)-2-methyl-4-propenal.

EXAMPLE 24
Tert-butyl (3S,7S,8S)-5-oxo-3-(triethylsilyloxy)-4,4,8-trimethyl-7-(2,2,2-trichloroethoxycarbonyloxy)-10-undecynoate

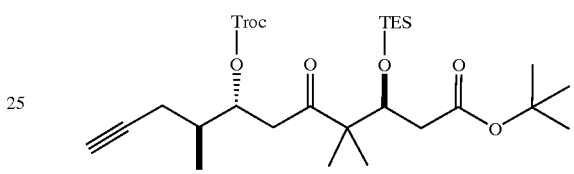

Prepared according to the method of Example 22, substituting (2S)-2-methyl-4-propynal for (2S)-2-methyl-4-propenal.

EXAMPLE 25
21-fluoro-10,11-dehydroepothilone D

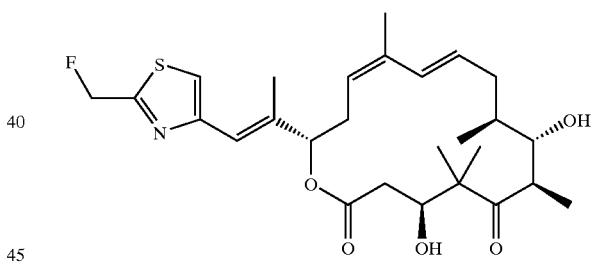

(a) 21-(p-toluenesulfonyloxy)-10,11-dehydroepothilone D

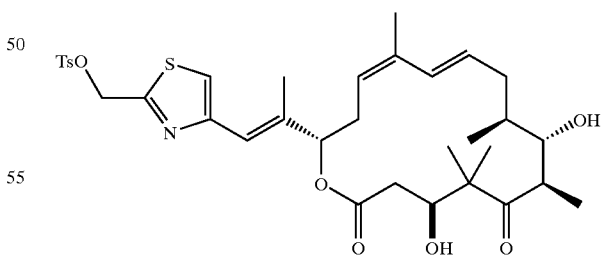

A solution of 21-hydroxy-10,11-dehydroepothilone D (40 mg) in 2 mL of CH$_2$Cl$_2$ is treated with pyridine (1 mL), 4-dimethylaminopyridine (1 mg), and p-toluenesulfonyl chloride (24 mg) at 0° C. for 30 minutes. The reaction is diluted with ethyl acetate and washed sequentially with 1 N HCl, sat. NaHCO$_3$, and brine, then dried over MgSO$_4$, filtered, and evaporated. The product is purified by SiO$_2$ chromatography (40% ethyl acetate/hexanes).

(b) 21-fluoro-10,11-dehydroepothilone D

A solution of 21-(p-toluenesulfonyloxy)-10,11-dehydroepothilone D (66 mg) in 5 mL of acetonitrile is treated with tetrabutylammonium (triphenylsilyl) difluorosilicate (216 mg) at reflux for 10 hours. The mixture is cooled and evaporated, and the residue is chromatographed on SiO$_2$ (40% ethyl acetate/hexanes) to provide the product.

EXAMPLE 26

(4S,7R,8S,9S,11E,12Z,15S)-4,8-dihydroxy-2,6-dioxo-5,5,7,9,13-pentamethyl-15-(6-quinolyl)-1-oxacyclodeca-11,13-diene

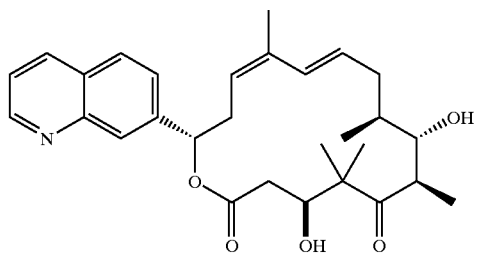

Is prepared according to the method of Example 10 replacing (6S)-2-iodo-5-(6-quinolyl)-5-(triethylsilyloxy)-2-pentene (Example 14) for (5S)-2-iodo-6-methyl-7-(2-methylthiazol-4-yl)-5-(triethylsilyloxy)-2,6-heptadiene.

EXAMPLE 27

12,13-methylene-10,11-dehydroepothilone D

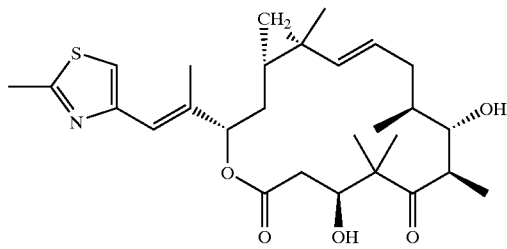

(a) 3,7-bis-O-(tert-butyldimethylsilyl)-10,11-anhydroepothilone D

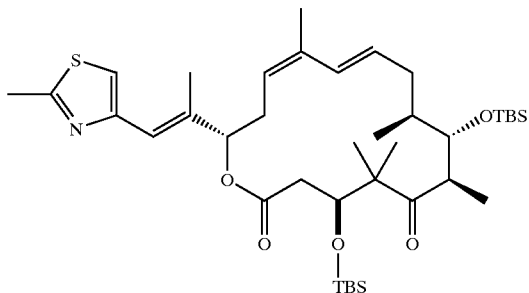

A solution of 10,11-dehydroepothilone D (530 mg) and 2,6-lutidine (0.61 mL) in 30 mL of CH$_2$Cl$_2$ at 0° C. is treated with tert-butyldimethylsilyl triflate (0.9 mL) for 1 hour, then queched by pouring into sat. NaHCO$_3$ and extracted with CH$_2$Cl$_2$. The extract is dried over Na$_2$SO$_4$, filtered, and concentrated. The product is purified by SiO$_2$ chromatography (10% ethyl acetate/hexanes).

(b) 12,13-(dibromomethylene)-3,7-bis-O-(tert-butyldimethylsilyl)-10,11-dehydroepothilone D

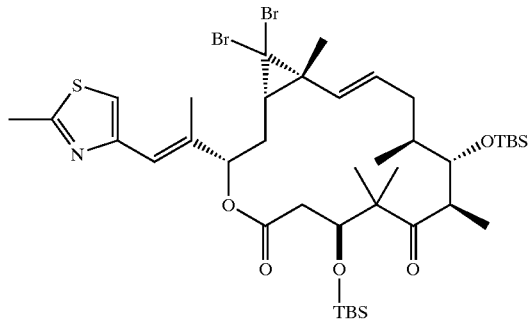

Benzyltriethylammonium chloride (7 mg), ethanol (20 uL), and 50% aq. NaOH are added sequentially to a solution of 3,7-bis-O-(tert-butyldimethylsilyl)-10,11-dehydroepothilone D (230 mg) in 2.7 mL of CHBr$_3$, and the mixture is stirred vigorously at 45° C. for 18 hours. The reaction is cooled to ambient temperature, poured into sat. NH4Cl, and extracted with CH$_2$Cl$_2$. The extract is dried over Na$_2$SO$_4$, filtered, and concentrated. The product is purified by SiO$_2$ chromatography (5% ethyl acetate/hexanes).

(c) 12,13-methylene-3,7-bis-O-(tert-butyldimethylsilyl)-10,11-dehydroepothilone D

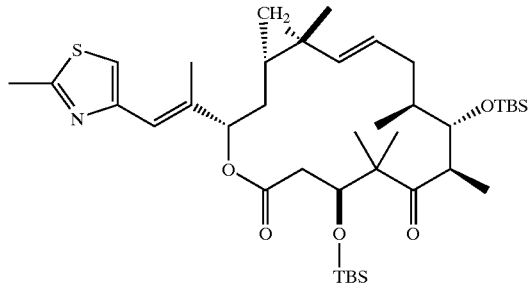

A solution of 12,13-(dibromomethylene)-3,7-bis-O-(tert-butyldimethylsilyl)-10,11-dehydroepothilone D (30 mg) in 0.5 mL of hexane is treated with tributyltin hydride (80 uL) and azobisisobutyronitrile (1 mg) at reflux for 9 hours. The mixture is cooled, concentrated, and chromatographed on SiO$_2$ to yield the product.

(d) 12,13-methylene-10,11-dehydroepothilone D. A solution of 12,13-methylene-3,7-bis-O-(tert-butyldimethylsilyl)-10,11-dehydroepothilone D (73 mg) in 1 mL of THF is treated with 0.5 mL of a 1 M solution of tetrabutylammonium fluoride in THIF for 1 hour. The mixture is diluted with ethyl acetate, washed sequentially with water and brine, then dried over Na$_2$SO$_4$, filtered, and evaporated. The product is purified by SiO$_2$ chromatography.

EXAMPLE 28

(4S,7R,8S,9S,11E,12Z,15S)-4,8-dihydroxy-2,6-dioxo-5,5,7,9,13-pentamethyl-15-(1-(2-methylthiazol-4-yl)propen-2-yl)-1-azacyclohexadeca-11,13-diene

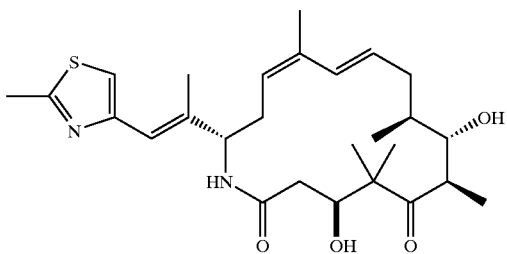

(a) tert-butyl (3S,6R,7S,8S,10E,12Z,15S,16E)-15-azido-5-oxo-3-(triethylsilyloxy)-17-(2-methylthiazol-4-yl)-4,4,6,8,12,16-hexamethyl-7-(2,2,2-trichloroethoxycarbonyloxy)-heptadeca-10,12,16-trienoate (Method A)

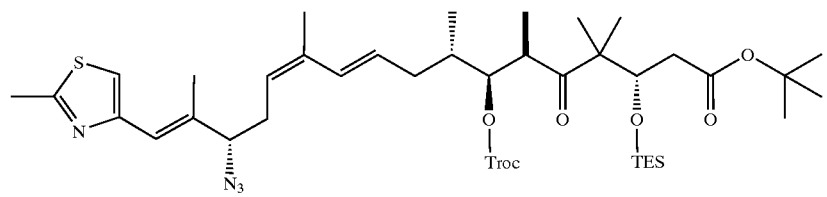

Method A: A solution of tert-butyl (3S,6R,7S,8S)-5-oxo-3-(triethylsilyloxy)-4,4,6,8-tetramethyl-7-(2,2,2-trichloroethoxycarbonyloxy)-10-undecenoate (2.12 g) in 4 mL of THF is added to a vigorously stirred mixture of (5S)-5-azido-2-iodo-6-methyl-7-(2-methylthiazol-4-yl)-2,6-heptadiene (1.1 g), cesium carbonate (1.49 g), triphenylarsine (0.188 g), and (dppf)PdCl$_2$·CH$_2$Cl$_2$ (0.25 g) in 2 mL of degassed dimethylformamide cooled to 0° C. The reaction is stirred for 15 hours, then poured into 10% NaHSO$_4$ and extracted with ethyl acetate. The organic phase is separated, washed sequentially with 10% NaHCO$_3$ and brine, dried over MgSO$_4$, filtered, and evaporated. The product is purified by flash chromatography on SiO$_2$ (10:1 hexanes/ethyl acetate).

Method B: A solution of tert-butyl (3S,6R,7S,8S)-5-oxo-3-(triethylsilyloxy)-4,4,6,8-tetramethyl-7-(2,2,2-trichloroethoxycarbonyloxy)-10-undecynoate (2.1 g) in 4 mL of THF is added to a 1.0 M solution of catecholborane in THF (3.3 mL), the mixture is stirred for 2 hour at 60° C. The resulting solution is added to a vigorously stirred mixture of (5S)-5-azido-2-iodo-6-methyl-7-(2-methylthiazol-4-yl)-2,6-heptadiene (1.1 g), cesium carbonate (1.49 g), triphenylarsine (0.188 g), and (dppf) PdCl$_2$·CH$_2$Cl$_2$ (0.25 g) in 2 mL poured into 10% NaHSO$_4$ and extracted with ethyl acetate. The organic phase is separated, washed sequentially with 10% NaHCO$_3$ and brine, dried over MgSO$_4$, filtered, and evaporated. The product is purified by flash chromatography on SiO$_2$.

(b) tert-butyl (3S,6R,7S,8S,11E,12Z,15S,16E)-15-(tert-butoxycarbonylamino)-5-oxo-3-(triethylsilyloxy)-17-(2-methylthiazol-4-yl)-4,4,6,8,12,16-hexamethyl-7-(2,2,2-trichloroethoxycarbonyloxy)-heptadeca-10,12,16-trienoate

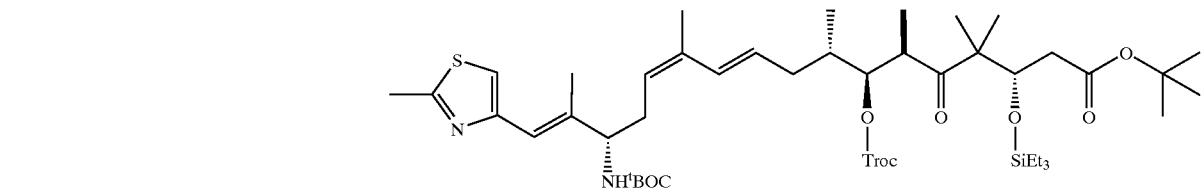

A solution of tert-butyl (3S,6R,7S,8S,11E,12Z,15S,16E)-15-azido-5-oxo-3-(triethylsilyloxy)-17-(2-methylthiazol-4-yl)-4,4,6,8,12,16-hexamethyl-7-(2,2,2-trichloroethoxycarbonyloxy)-heptadeca-10,12,16-trienoate (4.1 g) in 100 mL of THF is treated with triphenylphosphine (2.81 g) at 40° C. for 19 hours, then treated with 2 mL of water and heated at 65° C. for 4 hours. Silica gel (70 g) is added and the mixture is concentrated under vacuum. Silica gel chromatography (1.5% methanol in CHCl$_3$+0.5% Et$_3$N) yields the intermediate amine. The amine (3.3 g) is dissolved in 100 mL of acetonitrile and treated with tert-butyl pyrocarbonate (1.37 g) and triethylamine (0.91 g) for 16 hours at ambient temperature. The solution is diluted with ethyl acetate and washed sequentially with 1 N HCl, sat. NaHCO$_3$, and brine, then dried over MgSO$_4$, filtered, and evaporated. SiO2 chromatography provides the product.

(c) (3S,6R,7S,8S,11E,12Z,15S,16E)-15-amino-3-hydroxy-5-oxo-3-17-(2-methylthiazol-4-yl)-4,4,6,8,8,12,16-hexamethyl-7-(2,2,2-trichloroethoxycarbonyloxy)-heptadeca-10,12,16-trienoic acid

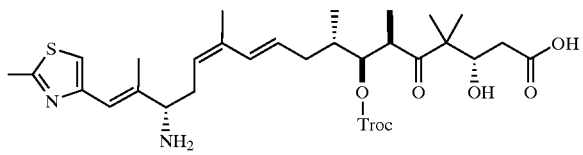

A solution of tert-butyl (3S,6R,7S,8S,11E,12Z,15S,16E)-15-(tert-butoxycarbonylamino)-5-oxo-3-(triethylsilyloxy)-17-(2-methylthiazol-4-yl)-4,4,6,8,12,16-hexamethyl-7-(2,2,2-trichloroethoxycarbonyloxy)-heptadeca-10,12,16-trienoate (0.8 g) in 20 mL of $CH_2Cl_2$ is treated with trifluoroacetic acid (10 mL) at ambient temperature for 2 hours, then is concentrated. The crude product is used without purification.

(d) (4S,7R,8S,9S,11E,12Z,15S)-4-hydroxy-2,6-dioxo-5,5,7,9,13-pentamethyl-15-(1-(2-methylthiazol-4-yl)propen-2-yl)-8-(2,2,2-trichloroethoxycarbonyloxy)-1-azacyclohexadeca-11,13-diene

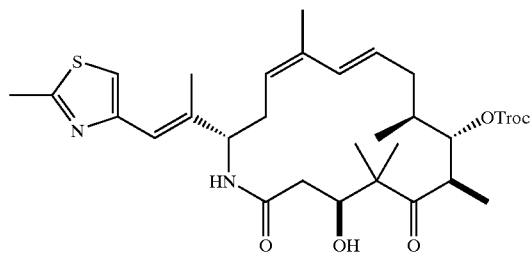

The crude product from step (c) above is dissolved in 10 mL of dimethylformamide and then diluted with 500 mL of $CH_2Cl_2$. This is treated with 1-hydroxy-7-azabenzotriazole (0.36 g), diisopropylethylamine (1.02 g), and O-(7-azabenzotriazol-1-yl)-N,N,N',N'-tetramethyluronium hexafluorophosphate (1.03 g) for 16 hours at ambient temperature. The mixture is washed with water, then dried over $MgSO_4$, filtered, and evaporated. The residue is dissolved in 30 mL of acetic acid/THF/water (3:1:1) for 30 minutes, then evaporated, neutralized with $NaHCO_3$, and extracted with ethyl acetate. The extract is dried over $MgSO_4$, filtered, and evaporated. The product is isolated by $SiO_2$ chromatography.

(e) (4S,7R,8S,9S,11E,12Z,15S)-4,8-dihydroxy-2,6-dioxo-5,5,7,9,13-pentamethyl-15-(1-(2-methylthiazol-4-yl)propen-2-yl)-1-azacyclohexadeca-11,13-diene.

A solution of (4S,7R,8S,9S,11E,12Z,15S)-4-hydroxy-2,6-dioxo-5,5,7,9,13-pentamethyl-15-(1-(2-methylthiazol-4-yl) propen-2-yl)-8-(2,2,2-trichloroethoxycarbonyloxy)-1-azacyclohexadeca-11,13-diene (0.18 g) in 1 mL of THF is added to a stirred suspension of activated zinc dust (0.261 g) in 2 mL of acetic acid. After stirring for 1.5 h, the mixture is diluted with ethyl acetate and filtered. The filtrate is washed sequentially with 10% $NaHCO_3$ and brine, dried over $MgSO_4$, filtered, and evaporated. The product is purified by flash chromatography on $SiO_2$.

EXAMPLE 29

(4S,7R,8S,9S,11E,12Z,15S)-4,8-dihydroxy-2,6-dioxo-5,5,7,9,13-pentamethyl-15-(1-(2-methylthiazol-4-yl)propen-2-yl)-1-azacyclohexadeca-11,13-diene

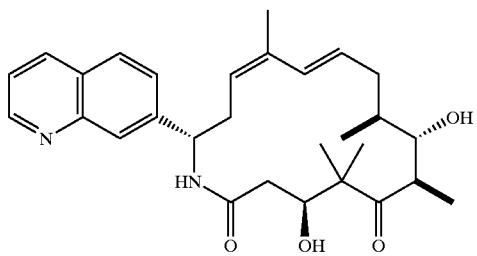

This is prepared according to the method of Example 28, substituting (5S)-5-azido-2-iodo-5-(6-quinolyl)-2-pentene (Example 19) in place of (5S)-5-azido-2-iodo-6-methyl-7-(2-methylthiazol-4-yl)-2,6-heptadiene.

EXAMPLE 30

(4S,7R,8S,9S,11E,12Z,15S)-4,8-dihydroxy-2,6-dioxo-1,5,5,7,9,13-hexamethyl-15-(1-(2-methylthiazol-4-yl)propen-2-yl)-1-azacyclohexadeca-11,13-diene

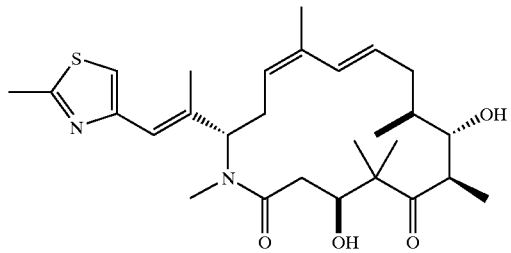

(a) (3S,6R,7S,8S,10E,12Z,15S,16E)-15-(methylamino)-3-hydroxy-5-oxo-3-17-(2-methylthiazol-4-yl)-4,4,6,8,12,16-hexamethyl-7-(2,2,2-trichloroethoxycarbonyloxy)-heptadeca-10,12,16-trienoic acid

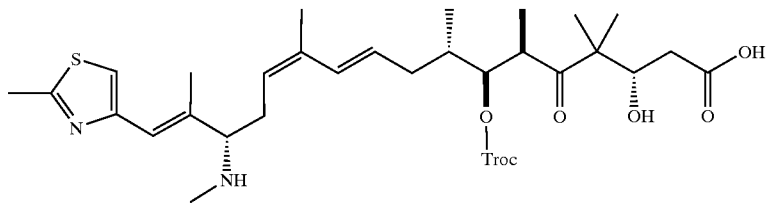

A solution of tert-butyl (3S,6R,7S,8S,10E, 12Z,15S,16E)-15-amino-5-oxo-3-(triethylsilyloxy)-17-(2-methylthiazol-4-yl)-4,4,6,8,12,16-hexamethyl-7-(2,2,2-trichloroethoxycarbonyloxy)-heptadeca-10,12,16-trienoate (0.68 g) in 5 mL of methanol is treated with acetaldehyde (50 mg), acetic acid (60 mg), and sodium cyanoborohydride (200 mg) for 12 hours at ambient temperature. The mixture is evaporated to dryness. The crude product is used without purification.

(b) (4S,7R,8S,9S,11E,12Z,15S)-4-hydroxy-2,6-dioxo-1,5,5,7,9,13-hexamethyl-15-(1-(2-methylthiazol-4-yl)propen-2-yl)-8-(2,2,2-trichloroethoxycarb6nyloxy)-1-azacyclohexadeca-11,13-diene

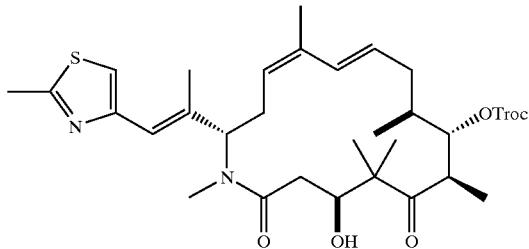

The crude product from step (a) above is dissolved in 10 mL of dimethylformamide and then diluted with 500 mL of CH$_2$Cl$_2$. This is treated with 1-hydroxy-7-azabenzotriazole (0.36 g), diisopropylethylamine (1.02 g), and O-(7-azabenzotriazol-1-yl)-N,N,N',N'-tetramethyluronium hexafluorophosphate (1.03 g) for 16 hours at ambient temperature. The mixture is washed with water, then dried over MgSO$_4$, filtered, and evaporated. The residue is dissolved in 30 mL of acetic acid/THF/water (3:1:1) for 30 minutes, then evaporated, neutralized with NaHCO$_3$, and extracted with ethyl acetate. The extract is dried over MgSO$_4$, filtered, and evaporated. The product is isolated by SiO$_2$ chromatography.

(c) (4S,7R,8S,9S,11E,12Z,15S)-4,8-dihydroxy-2,6-dioxo-1,5,5,7,9,13-hexamethyl-15-(1-(2-methylthiazol-4-yl)propen-2-yl)-1-azacyclohexadeca-11,13-diene.

A solution of (4S,7R,8S,9S,11E,12Z,15S)-4-hydroxy-2,6-dioxo-1,5,5,7,9,13-hexamethyl-15-(1-(2-methylthiazol-4-yl)propen-2-yl)-8-(2,2,2-trichloroethoxycarbonyloxy)-1-azacyclohexadeca-11,13-diene (0.18 g) in 1 mL of THF is added to a stirred suspension of activated zinc dust (0.261 g) in 2 mL of acetic acid. After stirring for 1.5 hours, the mixture is diluted with ethyl acetate and filtered. The filtrate is washed sequentially with 10% NaHCO$_3$ and brine, dried over MgSO$_4$, filtered, and evaporated. The product is purified by flash chromatography on SiO$_2$.

EXAMPLE 31
Epoxidation using EpoK

This example describes the enzymatic epoxidation of 10,11-dehydroepothilone D using EpoK to convert 10,11-dehydroepothilone D into 10,11-dehydroepothilone B. Briefly, the epoK gene product was expressed in E. coli as a fusion protein with a polyhistidine tag (his tag) and purified as described by PCT publication, WO 00/31247, incorporated herein by reference. The reaction consists of 50 mM Tris (pH7.5), 21 μM spinach ferredoxin, 0.132 units of spinach ferredoxin: NADP$^+$ oxidoreductase, 0.8 units of glucose-6-phosphate dehydrogenase, 1.4 mM NADP, and 7.1 mM glucose-6-phosphate, 100 μM or 200 μM 10,11-dehydroepothilone D, and 1.7 μM amino terminal histidine tagged EpoK or 1.6 μM carboxy terminal histidine tagged EpoK in a 100 μL volume. The reactions are incubated at 30° C. for 67 minutes and stopped by heating at 90° C. for 2 minutes. The insoluble material is removed by centrifugation, and 50 μL of the supernatant containing the desired product is analyzed by LC/MS.

EXAMPLE 32

This example describes liposomal compositions containing 10,11-dehydroepothilone D or other inventive compound. A mixture of lipids and 10,11-dehydroepothilone D are dissolved in ethanol and the solution is dried as a thin film by rotation under reduced pressure. The resultant lipid film is hydrated by addition of the aqueous phase and the particle size of the epothilone-derivative containing liposomes is adjusted to the desired range. Preferably, the mean particle diameter is less than 10 microns, preferably from about 0.5 to about 4 microns. The particle size may be reduced to the desired level, for example, by using mills (e.g., air-jet mill, ball mill, or vibrator mill), microprecipitation, spray-drying, lyophillization, high-pressure homogenization, recrystallization from supercritical media, or by extruding an aqueous suspension of the liposomes through a series of membranes (e.g., polycarbonate membranes) having a selected uniform pore size. In one embodiment, the liposomal composition comprises: an inventive compound (1.00 mg); phosphatidylcholine (16.25 mg); cholesterol (3.75 mg); polyethyleneglycol derivatized distearyl phosphatidylethanolamine (5.00 mg); lactose (80.00 mg); citric acid (4.20 mg); tartaric acid (6.00 mg); NaOH (5.44 mg); water (up to 1 mL). In another embodiment, the liposomal composition comprises: an inventive compound (1.00 mg); phosphatidylcholine (19.80 mg); cholesterol (3.75 mg); distearyl phosphatidylcholine (1.45 mg); lactose (80.00 mg); citric acid (4.20 mg); tartaric acid (6.00 mg); NaOH (5.44 mg); water (up to 1 mL). In yet another embodiment, the liposomal composition comprises: an inventive compound (1.00 mg); 1-palmitoyl-2-oleyl-sn-glycero-3-phosphocholine (17.50 mg); 1-palmitoyl-2-oleyl-sn-glycero-3-phosphoglycerol, NaCl (7.50 mg); lactose (80.mg); citric acid (4.20 mg); tartaric acid (6.00 mg); NaOH (5.44 mg); water (up to 1 mL). Liposomal compositions containing other compounds of the present invention are prepared using conditions similar to those described above.

EXAMPLE 33

This example describes the preparation of a poly-glutamic acid-21-hydroxy-10,11-dehydroepothilone D conjugate. Poly(1-glutamic acid) ("PG") sodium salt (MW 34 K, Sigma, 0.35 g) is dissolved in water. The pH of the aqueous solution is adjusted to 2 using 0.2 M HCl. The precipitate is collected, dialyzed against distilled water, and lyophilized to yield 0.29 g of PG. To a solution of PG (75 mg, repeating unit FW 170, 0.44 mmol) in dry DMF (1.5 mL) is added 20 mg of 21-hydroxy-10,11-dehydroepothilone D, 15 mg of dicyclohexylcarbodiimide ("DCC") and a trace amount of dimethylaminopyridine. The reaction is allowed to proceed at room temperature for four hours or until completed as indicated by thin layer chromatography. The reaction mixture is poured into chloroform and the resulting precipitate is collected and dried in a vacuum to yield approximately 65 mg of PG-21-hydroxy-10,11-dehydroepothilone D conjugate. Changing the weight ratio of inventive compound to PG in the starting materials results in polymeric conjugates of various concentrations of 21-hydroxyl-10,11-dehydroepothilone D. Conjugates of other compounds of the present invention are prepared using conditions similar to those described above.

EXAMPLE 34

This example describes an intravenous formulation of 10,11-dehydroepothilone D. The formulation contains 10 mg/mL of 10,11-dehydroepothilone D in a vehicle containing 30% propylene glycol, 20% Cremophor EL, and 50% ethanol. The vehicle is prepared by measuring ethanol (591.8 g) to a beaker containing a stir bar; adding Cremophor EL (315.0 g) to the solution and mixing for ten minutes; and then adding propylene glycol (466.2 g) to the solution and mixing for another ten minutes. 10,11-dehydroepothilone D (1 g) is added to a 1 L volumetric flask containing 400–600 mL of the vehicle and mixed for five minutes. After 10,11-dehydroepothilone D is in solution, the volume is brought to 1 L; allowed to mix for another ten minutes; and filtered through a 0.22 um Millipore Millipak filter. The resulting solution is used to aseptically fill sterile 5 mL vials using a metered peristaltic pump to a targeted fill volume of 5.15 mL/vial. The filled vials are immediately stoppered and crimped.

The vial containing 10 mg/mL of 10,11-dehydroepothilone D is diluted in normal saline or 5% dextrose solution for administration to patients and administered in non-PVC, non-DEHP bags and administration sets. The product is infused over a one to six hour period to deliver the desired dose.

In one embodiment, the formulation is diluted twenty fold in sterile saline prior to intravenous infusion. The final infusion concentration is 0.5 mg/mL of the inventive compound, 1.5% propylene glycol, 1% Cremophor EL, and 2.5% ethanol which is infused over a one to six hour period to deliver the desired dose.

Intravenous formulations containing other compounds of the present invention may be prepared and used in a similar manner.

EXAMPLE 35

This example describes a pretreatement regiment for for Cremophor® toxicity. Formulations of 10,11-dehydroepothilone D or another compound of the invention that includes Cremophor® may cause toxicity in patients. Pretreatment with steroids can be used to prevent anaphylaxis. Any suitable corticosterioid or combination of corticosteroid with $H_1$ antagonists and/or $H_2$ antagonists may be used. In one embodiment, a subject is premedicated with an oral dose of 50 mg of diphenylhydramine and 300 mg of cimetidine one hour prior to treatment with the inventive compound in a Cremophor® containing formulation. In another embodiment, the subject is premedicated with an intravenous administration of 20 mg of dexamethasone at least one half hour prior to treatment with the inventive compound in a Cremophor® containing formulation. In another embodiment, the subject is premedicated with an intravenous administration of 50 mg of diphenylhydrainine, 300 mg of cimetidine and 20 mg of dexamethasone at least one half hour prior to treatment with the inventive compound in a Cremophor® containing formulation. In yet another embodiment, the weight of the subject is taken into account and the subject is pretreated with an administration of diphenylhydramine (5 mg/kg, i.v.); cimetidine (5 mg/kg, i.v).; and dexamethasone (1 mg/kg, i.m.) at least one half hour prior to the treatment with the inventive compound in a Cremophor® containing formulation.

All scientific and patent publications referenced herein are hereby incorporated by reference. The invention having now been described by way of written description and example, those of skill in the art will recognize that the invention can be practiced in a variety of embodiments, that the foregoing description and example is for purposes of illustration and not limitation of the following claims.

What is claimed is:

1. A purified compound of the formula:

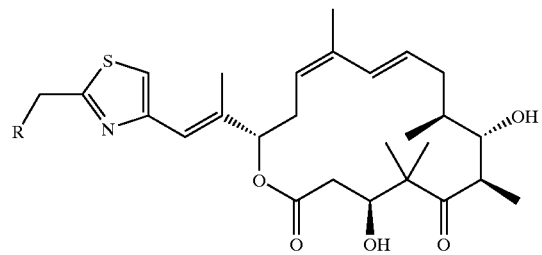

and all steroisomers thereof wherein R is hydrogen or hydroxyl.

2. The compound as in claim 1 wherein R is hydrogen.

3. The compound as in claim 1 wherein R is hydroxyl.

4. A purified compound having the structure

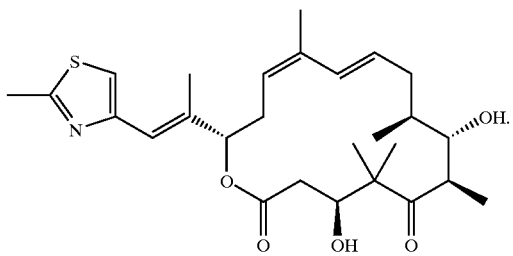

5. A compound having the structure

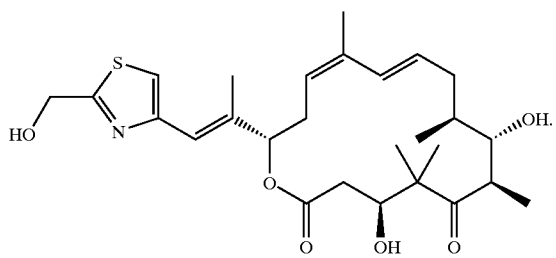

6. A composition comprising:
(i) a compound having the formula
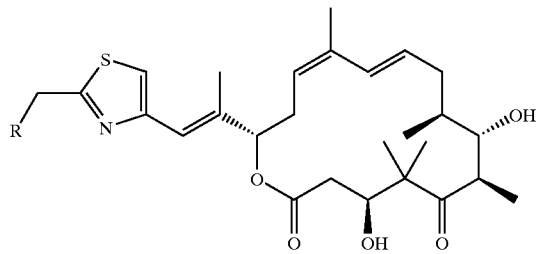
or a pharmaceutically acceptable salt or ester thereof; and
(ii) a pharmaceutically acceptable carrier.
7. The composition as in claim 6 where the compound is
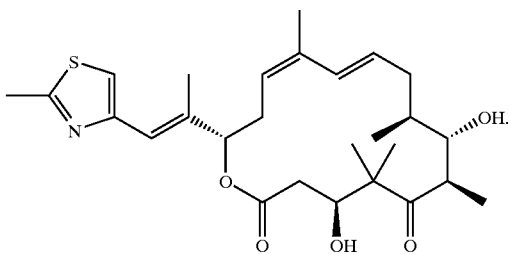
8. The composition as in claim 6 where the compound is
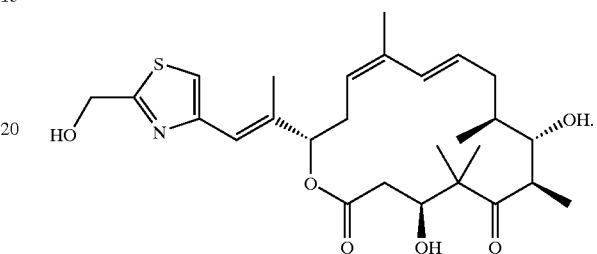
* * * * *